US012653560B2

(12) United States Patent
Nguyen et al.

(10) Patent No.: US 12,653,560 B2
(45) Date of Patent: Jun. 16, 2026

(54) ELECTRODE DESIGN FOR DIRECTIONAL LITHOTRIPSY CATHETERS

(71) Applicant: Shockwave Medical, Inc., Santa Clara, CA (US)

(72) Inventors: Hoa D. Nguyen, Santa Clara, CA (US); Anna-Elodie Kerlo, Felton, CA (US); Chi Long, San Jose, CA (US); Hester Chan, Santa Clara, CA (US); Huy Phan, Santa Clara, CA (US); Leela Goel, Santa Clara, CA (US); Tommy Nguyen, Santa Clara, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 566 days.

(21) Appl. No.: 18/071,240

(22) Filed: Nov. 29, 2022

(65) Prior Publication Data

US 2023/0165598 A1 Jun. 1, 2023

Related U.S. Application Data

(60) Provisional application No. 63/349,994, filed on Jun. 7, 2022, provisional application No. 63/284,582, filed on Nov. 30, 2021.

(51) Int. Cl.
*A61B 17/22* (2006.01)
(52) U.S. Cl.
CPC .. *A61B 17/22022* (2013.01); *A61B 2217/005* (2013.01); *A61B 2217/007* (2013.01)
(58) Field of Classification Search
CPC ....... A61B 17/22–22029; A61B 17/221–2258;
(Continued)

(56) References Cited

U.S. PATENT DOCUMENTS 2,916,647 A 12/1959 George
3,412,288 A 11/1968 Ostrander
(Continued)

FOREIGN PATENT DOCUMENTS

AU 2009313507 B2 11/2014
AU 2013284490 B2 5/2018
(Continued)

OTHER PUBLICATIONS

International Search Report and Written Opinion received for International Patent Application No. PCT/US2022/080596 mailed on Apr. 11, 2023, 10 pages.
(Continued)

*Primary Examiner* — Elizabeth Houston
*Assistant Examiner* — Jonathan A Hollm
(74) *Attorney, Agent, or Firm* — Morrison & Foerster LLP

(57) ABSTRACT

The present disclosure provides a catheter for treating lesions in a body lumen, such as calcified lesions and occlusions in vasculature. The catheter can include a dual-layer electrode assembly having a first conductive sheath and a second conductive sheath arranged circumferentially therearound. In some implementations, a first conductive sheath can be a flat coil. When a voltage is applied across the conductive sheaths, current flows across an arcing region, for example, from the distal side edge of the first sheath to the distal side edge of the second sheath to produce shock waves and/or cavitation bubbles. As a treatment continues, the sheaths slowly erode at the arcing region where current flows between the sheaths. To increase the lifespan of the electrode assembly, the distal side edges of the sheaths may be shaped to promote erosion of the sheaths in a predetermined or semi-controlled pattern.

20 Claims, 35 Drawing Sheets

(58) Field of Classification Search
CPC .................... A61B 2017/22001–22028; A61B
2017/2212–2253; A61B 18/26; A61B
2018/263–266; A61B 2018/147; G10K
15/04–06
See application file for complete search history.

(56) References Cited

U.S. PATENT DOCUMENTS

| | | |
|---|---|---|
| 3,413,976 A | 12/1968 | Roze |
| 3,524,101 A | 8/1970 | Barbini |
| 3,583,766 A | 6/1971 | Padberg |
| 3,785,382 A | 1/1974 | Schmidt-Kloiber et al. |
| 3,902,499 A | 9/1975 | Shene |
| 3,942,531 A | 3/1976 | Hoff et al. |
| 4,027,674 A | 6/1977 | Tessler et al. |
| 4,030,505 A | 6/1977 | Tessler |
| 4,445,509 A | 5/1984 | Auth |
| 4,662,126 A | 5/1987 | Malcolm |
| 4,662,375 A | 5/1987 | Hepp et al. |
| 4,671,254 A | 6/1987 | Fair |
| 4,685,458 A | 8/1987 | Leckrone |
| 4,741,405 A | 5/1988 | Moeny et al. |
| 4,774,947 A * | 10/1988 | Falk ................. A61B 17/22022 |
| | | 601/4 |
| 4,809,682 A | 3/1989 | Forssmann et al. |
| 4,813,934 A | 3/1989 | Engelson et al. |
| 4,878,495 A | 11/1989 | Grayzei |
| 4,890,603 A | 1/1990 | Filler |
| 4,900,303 A | 2/1990 | Lemelson |
| 4,990,134 A | 2/1991 | Auth |
| 4,994,032 A | 2/1991 | Sugiyama et al. |
| 5,006,119 A | 4/1991 | Acker et al. |
| 5,009,232 A | 4/1991 | Hassler et al. |
| 5,046,503 A | 9/1991 | Schneiderman |
| 5,057,103 A | 10/1991 | Davis |
| 5,057,106 A | 10/1991 | Kasevich et al. |
| 5,061,240 A | 10/1991 | Cherian |
| 5,078,717 A | 1/1992 | Parins et al. |
| 5,102,402 A | 4/1992 | Dror et al. |
| 5,103,804 A | 4/1992 | Abele et al. |
| 5,116,227 A | 5/1992 | Levy |
| 5,152,767 A | 10/1992 | Sypal et al. |
| 5,152,768 A | 10/1992 | Bhatta |
| 5,154,722 A | 10/1992 | Filip et al. |
| 5,176,675 A | 1/1993 | Watson et al. |
| 5,195,508 A | 3/1993 | Muller et al. |
| 5,245,988 A | 9/1993 | Einars et al. |
| 5,246,447 A | 9/1993 | Rosen et al. |
| 5,254,121 A | 10/1993 | Manevitz et al. |
| 5,281,231 A | 1/1994 | Rosen et al. |
| 5,295,958 A | 3/1994 | Shturman |
| 5,304,134 A | 4/1994 | Kraus et al. |
| 5,321,715 A | 6/1994 | Trost |
| 5,324,255 A | 6/1994 | Passafaro et al. |
| 5,336,234 A | 8/1994 | Vigil et al. |
| 5,362,309 A | 11/1994 | Carter |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,454,809 A | 10/1995 | Janssen |
| 5,472,406 A | 12/1995 | de la Torre et al. |
| 5,582,578 A | 12/1996 | Zhong et al. |
| 5,584,843 A | 12/1996 | Wulfman et al. |
| 5,603,731 A | 2/1997 | Whitney |
| 5,609,606 A | 3/1997 | O'Boyle |
| 5,662,590 A | 9/1997 | de la Torre et al. |
| 5,709,676 A | 1/1998 | Alt |
| 5,846,218 A | 12/1998 | Brisken et al. |
| 5,891,089 A | 4/1999 | Katz et al. |
| 5,893,840 A | 4/1999 | Hull et al. |
| 5,931,805 A | 8/1999 | Brisken |
| 6,007,530 A | 12/1999 | Dornhofer et al. |
| 6,033,371 A | 3/2000 | Torre et al. |
| 6,056,722 A | 5/2000 | Jayaraman |
| 6,080,119 A | 6/2000 | Schwarze et al. |
| 6,083,232 A | 7/2000 | Cox |
| 6,090,104 A | 7/2000 | Webster et al. |
| 6,113,560 A | 9/2000 | Simnacher |
| 6,132,444 A | 10/2000 | Shturman et al. |
| 6,146,358 A | 11/2000 | Rowe |
| 6,186,963 B1 | 2/2001 | Schwarze et al. |
| 6,210,408 B1 | 4/2001 | Chandrasekaran et al. |
| 6,215,734 B1 | 4/2001 | Moeny et al. |
| 6,217,531 B1 | 4/2001 | Reitmajer |
| 6,267,747 B1 | 7/2001 | Samson et al. |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,364,894 B1 | 4/2002 | Healy et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | de la Torre et al. |
| 6,440,124 B1 | 8/2002 | Esch et al. |
| 6,494,890 B1 | 12/2002 | Shturman et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,666,834 B2 | 12/2003 | Restle et al. |
| 6,689,089 B1 | 2/2004 | Tiedtke et al. |
| 6,736,784 B1 | 5/2004 | Menne et al. |
| 6,740,081 B2 | 5/2004 | Hilal |
| 6,755,821 B1 | 6/2004 | Fry |
| 6,939,320 B2 | 9/2005 | Lennox |
| 6,989,009 B2 | 1/2006 | Lafontaine |
| 7,066,904 B2 | 6/2006 | Rosenthal et al. |
| 7,087,061 B2 | 8/2006 | Chernenko et al. |
| 7,241,295 B2 | 7/2007 | Maguire |
| 7,309,324 B2 | 12/2007 | Hayes et al. |
| 7,389,148 B1 | 6/2008 | Morgan |
| 7,505,812 B1 * | 3/2009 | Eggers ................. A61B 18/149 |
| | | 604/20 |
| 7,569,032 B2 | 8/2009 | Naimark et al. |
| 7,850,685 B2 | 12/2010 | Kunis et al. |
| 7,853,332 B2 | 12/2010 | Olsen et al. |
| 7,873,404 B1 | 1/2011 | Patton |
| 7,951,111 B2 | 5/2011 | Drasler et al. |
| 8,162,859 B2 | 4/2012 | Schultheiss et al. |
| 8,177,801 B2 | 5/2012 | Kallok et al. |
| 8,353,923 B2 | 1/2013 | Shturman |
| 8,556,813 B2 | 10/2013 | Cioanta et al. |
| 8,574,247 B2 | 11/2013 | Adams et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 8,956,371 B2 | 2/2015 | Hawkins et al. |
| 8,956,374 B2 | 2/2015 | Hawkins et al. |
| 9,005,216 B2 | 4/2015 | Hakala et al. |
| 9,011,462 B2 | 4/2015 | Adams et al. |
| 9,011,463 B2 | 4/2015 | Adams et al. |
| 9,044,618 B2 | 6/2015 | Hawkins et al. |
| 9,044,619 B2 | 6/2015 | Hawkins et al. |
| 9,060,785 B2 | 6/2015 | Howat et al. |
| 9,072,534 B2 | 7/2015 | Hawkins et al. |
| 9,138,249 B2 | 9/2015 | Adams et al. |
| 9,198,825 B2 | 12/2015 | Katragadda et al. |
| 9,333,000 B2 | 5/2016 | Hakala et al. |
| 9,421,025 B2 | 8/2016 | Hawkins et al. |
| 9,433,428 B2 | 9/2016 | Hakala et al. |
| 9,522,012 B2 | 12/2016 | Adams |
| 9,642,673 B2 | 5/2017 | Adams et al. |
| 9,993,292 B2 | 6/2018 | Adams et al. |
| 10,039,561 B2 | 8/2018 | Adams et al. |
| 10,118,015 B2 | 11/2018 | De La Rama et al. |
| 10,149,690 B2 | 12/2018 | Hawkins et al. |
| 10,154,799 B2 | 12/2018 | Van Der Weide et al. |
| 10,159,505 B2 | 12/2018 | Hakala et al. |
| 10,206,698 B2 | 2/2019 | Hakala et al. |
| 10,226,265 B2 | 3/2019 | Ku et al. |

(56) References Cited

U.S. PATENT DOCUMENTS

| | | |
|---|---|---|
| 10,517,620 B2 | 12/2019 | Adams |
| 10,517,621 B1 | 12/2019 | Adams |
| 10,555,744 B2 | 2/2020 | Nguyen et al. |
| 10,682,178 B2 | 6/2020 | Adams et al. |
| 10,702,293 B2 | 7/2020 | Hawkins et al. |
| 10,709,462 B2 | 7/2020 | Nguyen et al. |
| 10,959,743 B2 | 3/2021 | Adams et al. |
| 10,966,737 B2 | 4/2021 | Nguyen |
| 10,973,538 B2 | 4/2021 | Hakala et al. |
| 11,000,299 B2 | 5/2021 | Hawkins et al. |
| 11,076,874 B2 | 8/2021 | Hakala et al. |
| 11,337,713 B2 | 5/2022 | Nguyen et al. |
| 11,432,834 B2 | 9/2022 | Adams |
| 11,534,187 B2 | 12/2022 | Bonutti |
| 11,596,424 B2 | 3/2023 | Hakala et al. |
| 11,622,780 B2 | 4/2023 | Nguyen et al. |
| 11,696,799 B2 | 7/2023 | Adams et al. |
| 11,771,449 B2 | 10/2023 | Adams et al. |
| 2001/0044596 A1 | 11/2001 | Jaafar |
| 2002/0045890 A1 | 4/2002 | Celliers et al. |
| 2002/0082553 A1 | 6/2002 | Duchamp |
| 2002/0177889 A1 | 11/2002 | Brisken et al. |
| 2003/0004434 A1 | 1/2003 | Greco et al. |
| 2003/0176873 A1 | 9/2003 | Chernenko et al. |
| 2003/0229370 A1 | 12/2003 | Miller |
| 2004/0006333 A1 | 1/2004 | Arnold et al. |
| 2004/0010249 A1 | 1/2004 | Truckai et al. |
| 2004/0044308 A1 | 3/2004 | Naimark et al. |
| 2004/0097963 A1 | 5/2004 | Seddon |
| 2004/0097996 A1 | 5/2004 | Rabiner et al. |
| 2004/0162508 A1 | 8/2004 | Uebelacker |
| 2004/0249401 A1 | 12/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0059965 A1 | 3/2005 | Eberl et al. |
| 2005/0075662 A1 | 4/2005 | Pedersen et al. |
| 2005/0090888 A1 | 4/2005 | Hines et al. |
| 2005/0113722 A1 | 5/2005 | Schultheiss |
| 2005/0113822 A1 | 5/2005 | Fuimaono et al. |
| 2005/0171527 A1 | 8/2005 | Bhola |
| 2005/0228372 A1 | 10/2005 | Truckai et al. |
| 2005/0245866 A1 | 11/2005 | Azizi |
| 2005/0251131 A1 | 11/2005 | Lesh |
| 2006/0004286 A1 | 1/2006 | Chang et al. |
| 2006/0069424 A1 | 3/2006 | Acosta et al. |
| 2006/0074484 A1 | 4/2006 | Huber |
| 2006/0184076 A1 | 8/2006 | Gill et al. |
| 2006/0190022 A1 | 8/2006 | Beyar et al. |
| 2006/0221528 A1 | 10/2006 | Li et al. |
| 2007/0016112 A1 | 1/2007 | Schultheiss et al. |
| 2007/0088380 A1 | 4/2007 | Hirszowicz et al. |
| 2007/0129667 A1 | 6/2007 | Tiedtke et al. |
| 2007/0156129 A1 | 7/2007 | Kovalcheck |
| 2007/0239082 A1 | 10/2007 | Schultheiss et al. |
| 2007/0239253 A1 | 10/2007 | Jagger et al. |
| 2007/0244423 A1 | 10/2007 | Zumeris et al. |
| 2007/0250052 A1 | 10/2007 | Wham |
| 2007/0255270 A1 | 11/2007 | Carney |
| 2007/0282301 A1 | 12/2007 | Segalescu et al. |
| 2007/0299481 A1 | 12/2007 | Syed et al. |
| 2008/0097251 A1 | 4/2008 | Babaev |
| 2008/0188913 A1 | 8/2008 | Stone et al. |
| 2009/0041833 A1 | 2/2009 | Bettinger et al. |
| 2009/0227992 A1 | 9/2009 | Nir et al. |
| 2009/0230822 A1 | 9/2009 | Kushculey et al. |
| 2009/0247945 A1 | 10/2009 | Levit et al. |
| 2009/0254114 A1 | 10/2009 | Hirszowicz et al. |
| 2009/0299447 A1 | 12/2009 | Jensen et al. |
| 2010/0016862 A1 | 1/2010 | Hawkins et al. |
| 2010/0036294 A1 | 2/2010 | Mantell et al. |
| 2010/0094209 A1 | 4/2010 | Drasler et al. |
| 2010/0114020 A1 | 5/2010 | Hawkins et al. |
| 2010/0114065 A1 | 5/2010 | Hawkins et al. |
| 2010/0121322 A1 | 5/2010 | Swanson |

| | | |
|---|---|---|
| 2010/0179424 A1 | 7/2010 | Warnking et al. |
| 2010/0286709 A1 | 11/2010 | Diamant et al. |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0208185 A1 | 8/2011 | Diamant et al. |
| 2011/0257523 A1 | 10/2011 | Hastings et al. |
| 2011/0295227 A1 | 12/2011 | Hawkins et al. |
| 2012/0071889 A1 | 3/2012 | Mantell et al. |
| 2012/0095461 A1 | 4/2012 | Herscher et al. |
| 2012/0116289 A1 | 5/2012 | Hawkins et al. |
| 2012/0143177 A1 | 6/2012 | Avitall et al. |
| 2012/0157991 A1 | 6/2012 | Christian |
| 2012/0203255 A1 | 8/2012 | Hawkins et al. |
| 2012/0253358 A1 | 10/2012 | Golan et al. |
| 2013/0030431 A1 | 1/2013 | Adams |
| 2013/0041355 A1 | 2/2013 | Heeren et al. |
| 2013/0116714 A1 | 5/2013 | Adams et al. |
| 2013/0123694 A1 | 5/2013 | Subramaniyan et al. |
| 2013/0150874 A1 | 6/2013 | Kassab |
| 2013/0253622 A1 | 9/2013 | Hooven |
| 2014/0046229 A1 | 2/2014 | Hawkins et al. |
| 2014/0214061 A1 | 7/2014 | Adams et al. |
| 2015/0320432 A1 | 11/2015 | Adams |
| 2016/0151081 A1 | 6/2016 | Adams et al. |
| 2016/0324534 A1 | 11/2016 | Hawkins et al. |
| 2017/0135709 A1 | 5/2017 | Nguyen et al. |
| 2017/0311965 A1 | 11/2017 | Adams |
| 2019/0029703 A1 | 1/2019 | Wasdyke et al. |
| 2019/0388110 A1* | 12/2019 | Nguyen ........... A61B 17/22012 |
| 2021/0085347 A1 | 3/2021 | Phan et al. |
| 2021/0085348 A1 | 3/2021 | Nguyen |
| 2021/0085383 A1 | 3/2021 | Vo et al. |
| 2021/0338258 A1 | 11/2021 | Hawkins et al. |
| 2022/0015785 A1 | 1/2022 | Hakala et al. |
| 2022/0240958 A1 | 8/2022 | Nguyen et al. |
| 2023/0043475 A1 | 2/2023 | Adams |
| 2023/0293197 A1 | 9/2023 | Nguyen et al. |
| 2023/0310073 A1 | 10/2023 | Adams et al. |
| 2023/0329731 A1 | 10/2023 | Hakala et al. |

FOREIGN PATENT DOCUMENTS

| | | |
|---|---|---|
| CA | 2104414 A1 | 2/1995 |
| CN | 1204242 A | 1/1999 |
| CN | 1269708 A | 10/2000 |
| CN | 1942145 A | 4/2007 |
| CN | 101043914 A | 9/2007 |
| CN | 102057422 A | 5/2011 |
| CN | 102271748 A | 12/2011 |
| CN | 102355856 A | 2/2012 |
| CN | 102765785 A | 11/2012 |
| CN | 203564304 U | 4/2014 |
| DE | 3038445 A1 | 5/1982 |
| DE | 202006014285 U1 | 12/2006 |
| EP | 0442199 A2 | 8/1991 |
| EP | 0571306 A1 | 11/1993 |
| EP | 623360 A1 | 11/1994 |
| EP | 0647435 A1 | 4/1995 |
| EP | 2253884 A1 | 11/2010 |
| EP | 2362798 B1 | 4/2014 |
| EP | 3766447 A1 | 1/2021 |
| JP | S62-099210 U | 6/1987 |
| JP | S62-275446 A | 11/1987 |
| JP | H03-63059 A | 3/1991 |
| JP | H06-125915 A | 5/1994 |
| JP | H07-47135 A | 2/1995 |
| JP | H08-89511 A | 4/1996 |
| JP | H10-99444 A | 4/1998 |
| JP | H10-314177 A | 12/1998 |
| JP | H10-513379 A | 12/1998 |
| JP | 2002538932 A | 11/2002 |
| JP | 2004081374 A | 3/2004 |
| JP | 2004357792 A | 12/2004 |
| JP | 2011520248 A | 12/2004 |
| JP | 2005501597 A | 1/2005 |
| JP | 2005095410 A | 4/2005 |
| JP | 2005515825 A | 6/2005 |
| JP | 2006516465 A | 7/2006 |

(56) References Cited

FOREIGN PATENT DOCUMENTS

| | | | |
|---|---|---|---|
| JP | 2007289707 | A | 11/2007 |
| JP | 2007532182 | A | 11/2007 |
| JP | 2008506447 | A | 3/2008 |
| JP | 2011513694 | A | 4/2011 |
| JP | 2011524203 | A | 9/2011 |
| JP | 2011528963 | A | 12/2011 |
| JP | 2012505050 | A | 3/2012 |
| JP | 2012508042 | A | 4/2012 |
| JP | 2015525657 | A | 9/2015 |
| JP | 2015528327 | A | 9/2015 |
| JP | 6029828 | B2 | 11/2016 |
| JP | 6081510 | B2 | 2/2017 |
| WO | WO-1989011307 | A1 | 11/1989 |
| WO | WO-1996024297 | A1 | 8/1996 |
| WO | WO-1999000060 | A1 | 1/1999 |
| WO | WO-1999002096 | A1 | 1/1999 |
| WO | WO-2000056237 | A2 | 9/2000 |
| WO | WO-2004069072 | A2 | 8/2004 |
| WO | WO-2005099594 | A1 | 10/2005 |
| WO | WO-2005102199 | A1 | 11/2005 |
| WO | WO-2006006169 | A2 | 1/2006 |
| WO | WO-2006127158 | A2 | 11/2006 |
| WO | WO-2007088546 | A2 | 8/2007 |
| WO | WO-2007149905 | A2 | 12/2007 |
| WO | WO-2009121017 | A1 | 10/2009 |
| WO | WO-2009126544 | A1 | 10/2009 |
| WO | WO-2009136268 | A1 | 11/2009 |
| WO | WO-2009152352 | A2 | 12/2009 |
| WO | WO-2010014515 | A2 | 2/2010 |
| WO | WO-2010054048 | A2 | 9/2010 |
| WO | WO-2011006017 | A1 | 1/2011 |
| WO | WO-2011094111 | A2 | 8/2011 |
| WO | WO-2011143468 | A2 | 11/2011 |
| WO | WO-2012025833 | A2 | 3/2012 |
| WO | WO-2013059735 | A1 | 4/2013 |
| WO | WO-2014025397 | A1 | 2/2014 |
| WO | WO-2014025620 | A1 | 2/2014 |
| WO | WO-2015017499 | A1 | 2/2015 |
| WO | WO-2019099218 | A1 | 5/2019 |

OTHER PUBLICATIONS

Office Action received for Australian Patent Application No. 2022401861, mailed on Jun. 26, 2025, 3 pages.
Extended European Search Report received for European Patent Application No. 22902343.7 mailed Sep. 9, 2025, 9 pages.

* cited by examiner

20

100

100

120

121

121

120

100
120    140    122    123    121    132    8C
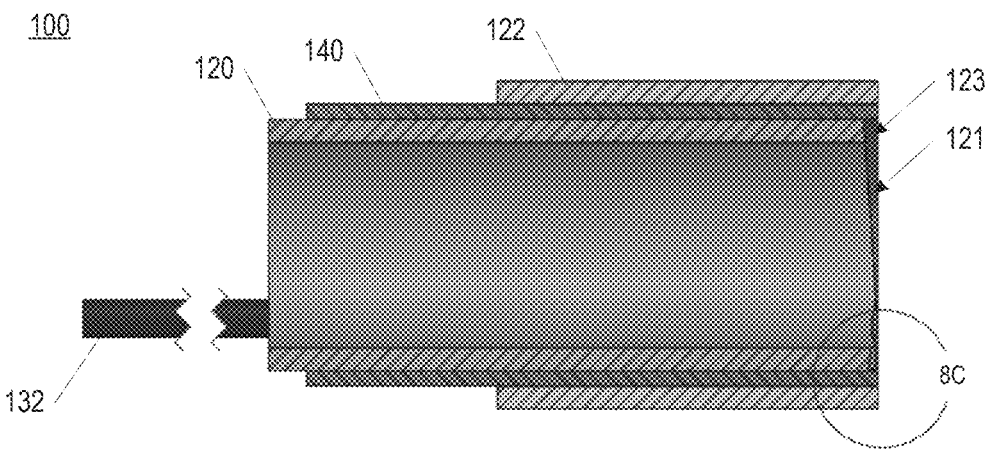
FIG. 8A
132    8A    120    140    122    8A    125    126
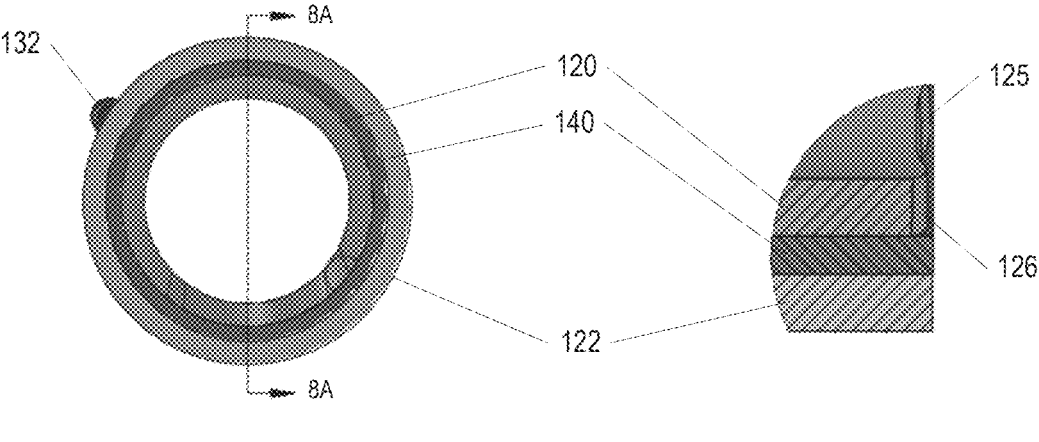
FIG. 8B                    FIG. 8C

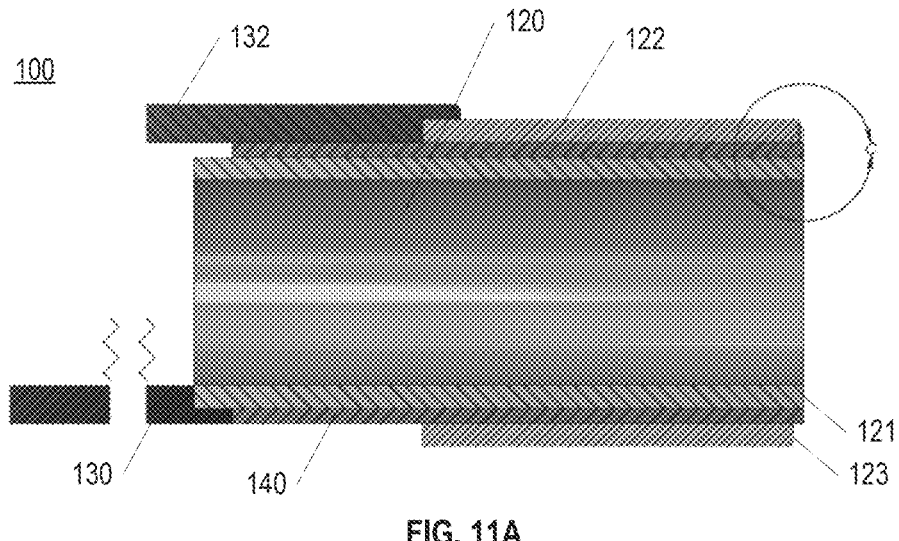
FIG. 11A
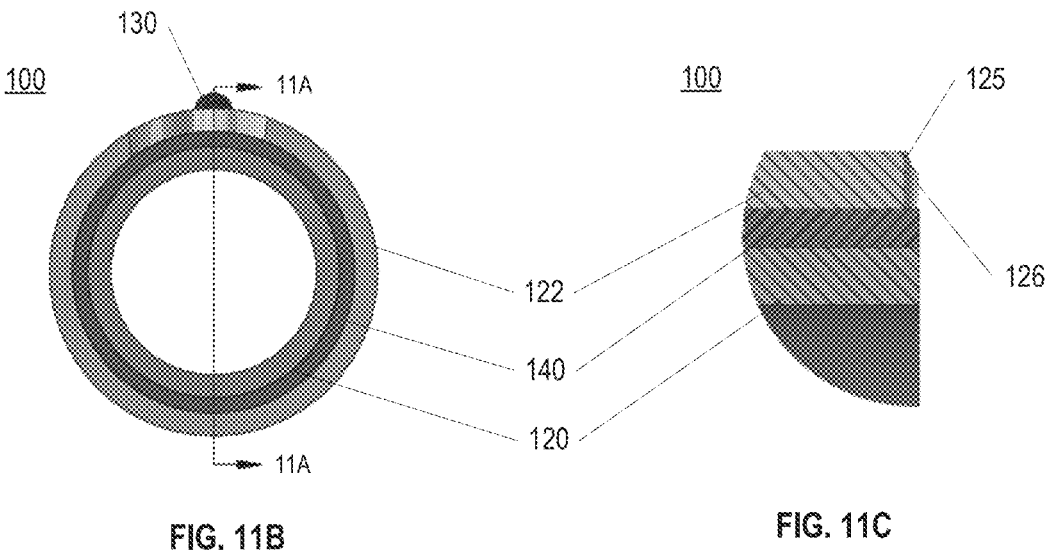
FIG. 11B        FIG. 11C

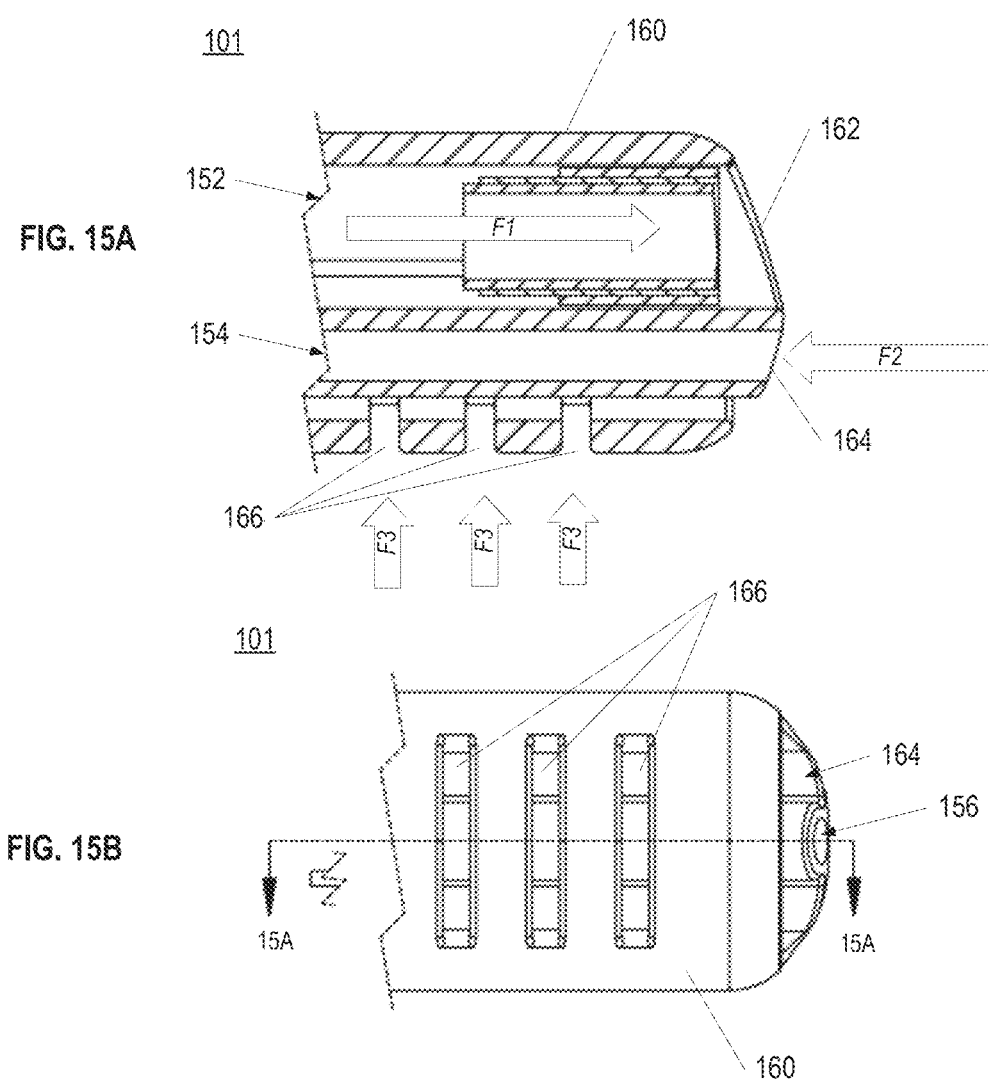
FIG. 15A
FIG. 15B
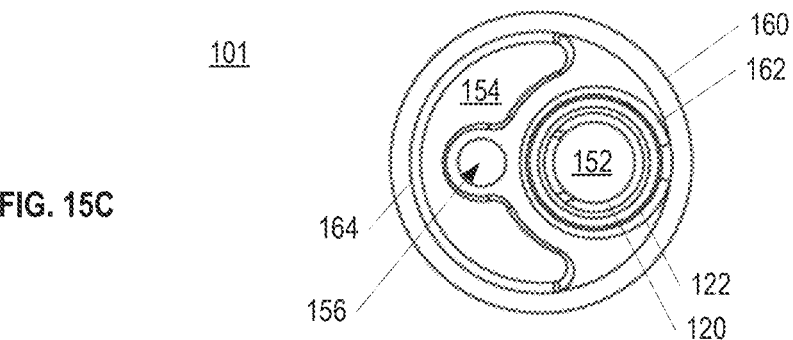
FIG. 15C

Pressure (Mpa)

|  | @10mm | Est.@~1mm |
|---|---|---|
| Peak Positive (Mpa) | 1.32 | 13.2 |
| Peak Negative (Mpa) | 0.19 | 1.9 |
| Peak to Peak (Mpa) | 1.5 | 15 |

| | Est. @1mm |
|---|---|
| Peak Positive: | 4.20 MPa |
| Peak Negative: | 2.03 MPa |
| Peak to Peak: | 6.23 MPa |

FIG. 31B
FIG. 31C
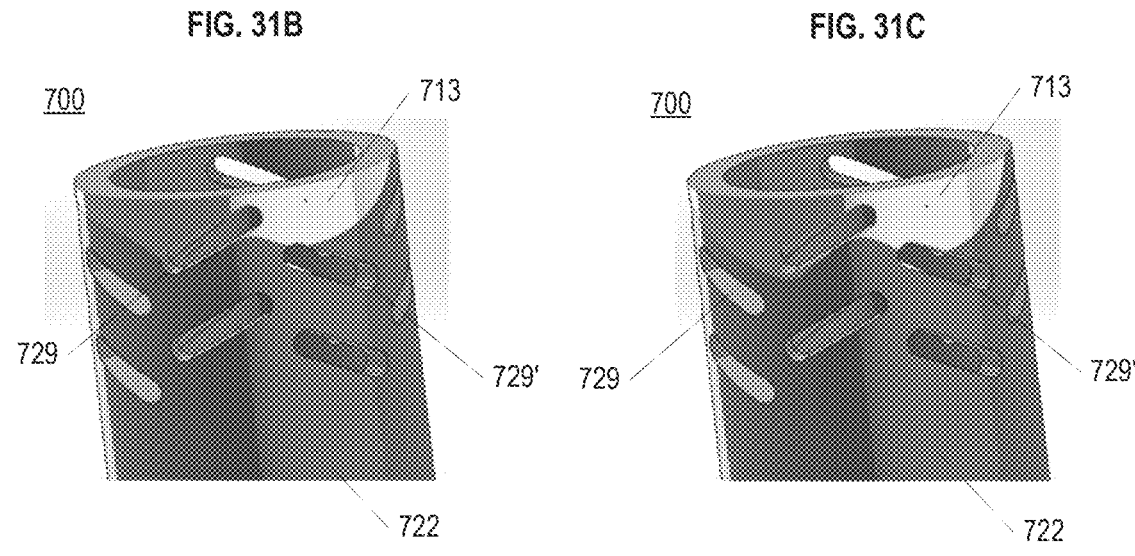
FIG. 31D
FIG. 31E
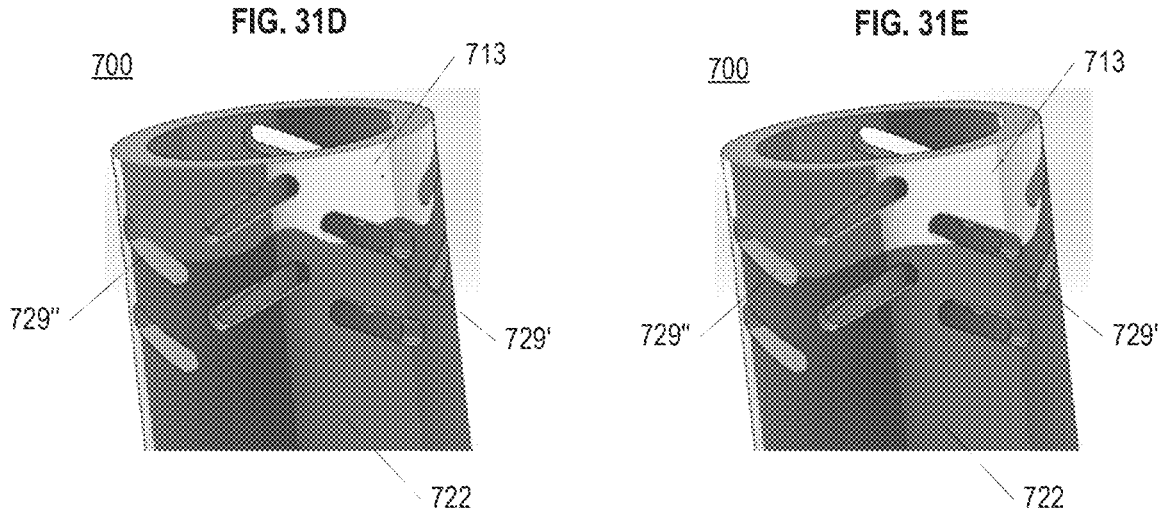

1

ELECTRODE DESIGN FOR DIRECTIONAL LITHOTRIPSY CATHETERS

CROSS-REFERENCE TO RELATED APPLICATIONS

This application claims priority to U.S. Provisional Patent Application Ser. No. 63/284,582 entitled "DUAL-LAYER ELECTRODE DESIGN FOR LITHOTRIPSY CATH-ETERS" filed on Nov. 30, 2021, and to U.S. Provisional Patent Application Ser. No. 63/349,994 entitled "HELICAL ELECTRODE DESIGN FOR LITHOTRIPSY CATH-ETERS" filed on Jun. 7, 2022, which are hereby incorporated by reference in their entireties.

FIELD OF THE DISCLOSURE

The present disclosure relates generally to the field of medical devices and methods, and more specifically to electrode assemblies for inclusion in catheter devices used for treating lesions in a body lumen, such as calcified lesions and occlusions in vasculature and kidney stones in the urinary system.

BACKGROUND

Calcified lesions in body lumens can negatively impact patient health. For example, when calcium builds up in the walls of the coronary arteries, the calcification of the arteries can restrict blood flow to the heart muscle, which can eventually lead to a heart attack. Catheter devices are one type of device that can be used to treat calcified lesions in a body lumen, such as an artery. When treating lesions with a catheter device, it is important to minimize the damage to the surrounding soft tissues, while still breaking up the lesion as much as possible.

A wide variety of catheters have been developed for treating lesions, such as calcified lesions and plaques in vasculature associated with arterial disease. For example, treatment systems for percutaneous coronary angioplasty or peripheral angioplasty use angioplasty balloons to dilate a calcified lesion and restore normal blood flow in a vessel. In these types of procedures, a catheter carrying a balloon is advanced into the vasculature along a guide wire until the balloon is aligned with calcified plaques. The balloon is then pressurized, causing the balloon to expand in a vessel to push calcified plaques back into the vessel wall and dilate occluded regions of vasculature. Balloons having different diameters and lengths can be used to access different anatomy, appropriate to coronary vasculature or different types of peripheral vasculature (e.g., above-the-knee, below-the-knee, arm artery disease, etc.).

More recently, catheters have been developed that include one or more electrode pairs for generating shock waves inside an angioplasty balloon. Such shock wave devices can be particularly effective for treating calcified lesions because the acoustic pressure from the shock waves can crack and disrupt lesions near the angioplasty balloon without harming the surrounding tissue. This therapy has become known as intravascular lithotripsy (IVL), although the principles of using shock wave devices are not limited to systems that include balloons. In these devices, the catheter is advanced over a guidewire through a patient's vasculature until it is positioned proximal to a lesion in a body lumen. The balloon is then inflated with conductive fluid so that the balloon expands to contact the lesion. The shock wave emitters can then be activated to produce acoustic shock waves (a conversion of electrical to mechanical energy) that propagate through the walls of the angioplasty balloon and into the lesions. Once the lesions have been cracked by the acoustic shock waves, the balloon can be expanded further to increase the cross-sectional area of the lumen and improve blood flow through the vessel.

Catheters have also been developed that include electrode pairs for generating directed cavitation bubbles for the treatment calcified lesions in vasculature. In these devices, an open-ended catheter is advanced into a patient's vasculature using a guidewire until it is proximal to a lesion. A relatively lower voltage is applied across the electrode pairs at a relatively higher repetition rate, causing gas cavitation bubbles to form on the surface of the electrodes. The cavitation bubbles begin to accumulate on the electrodes, until fluid flow through the open distal tip of the catheter flows the cavitation bubbles into a target lesion in the body lumen. Once the lesion has been sufficiently reduced by the cavitation bubbles, debris can be aspirated from the treatment site and the catheter can be removed from the vessel. Implementations of such open-ended catheters allow for a degree of directional control, guiding where the cavitation bubbles are formed and how they progress and develop outward from the catheter.

Efforts have been made to improve the design of electrode assemblies included in shock wave and directed cavitation catheters. For instance, low-profile electrode assemblies have been developed that reduce the crossing profile of a catheter and allow the catheter to more easily navigate calcified vessels to deliver shock waves in more severely occluded regions of vasculature. Examples of low-profile electrode designs can be found in U.S. Pat. Nos. 8,888,788, and 10,709,462, both of which are incorporated herein by reference. Other catheter designs have improved the delivery of shock waves, for instance, by specific electrode construction and configuration thereby directing shock waves in a forward direction to break up tighter and harder-to-cross occlusions in vasculature. Examples of forward-firing catheter designs can be found in U.S. Pat. No. 10,966, 737 and U.S. Publication Nos. 2019/0388110 and 2021/085348, all of which are incorporated herein by reference.

Despite these advances in electrode assembly design, the duration of a treatment with a shock wave or cavitation catheter is limited by the lifespan of electrode pairs included in the catheter, which slowly erode and degrade as shock waves and/or cavitation bubbles are generated across the electrodes. Many currently available catheter designs include electrodes formed from conductive wires or other narrow conductive materials, which have a relatively small conductive surface area and degrade quickly during a procedure. Other electrode assemblies degrade in random or unfavorable patterns that reduce the lifespan of the electrodes. Accordingly, many catheters cannot be used for more than one hour before the electrodes have eroded too far to continue treatment. As a result, many currently available designs lack the longevity necessary for longer shock wave procedures, such as procedures to remove resistant lesions and treat more chronically occluded regions of vasculature. Thus, provided herein are variations of electrode structures and designs to address the unmet need for shock wave and cavitation catheter designs that incorporate electrode assemblies with an increased lifespan and more favorable degradation patterns. In particular, the electrode structures and designs herein also provide for a significant degree of directional control for the formation of a shock waves and cavitation bubbles emitted from the electrode assembly.

SUMMARY

A catheter having an electrode pair that is configured to generate shockwaves and/or cavitation bubbles can be useful to treat calcified lesions in a body lumen (such as the vasculature) without damaging the surrounding soft tissues. When used to treat lesions, voltage can be applied across the electrodes which causes shockwaves and/or cavitation bubbles to form. Thereafter, the shockwaves and/or cavitation bubbles can be flowed outwardly, such as from the distal end of an open-ended catheter, to the treatment location. Once the lesion has been sufficiently reduced, debris can be aspirated from the treatment site.

When using such catheter devices to treat and remove calcified lesions, the electrodes of the electrode pair can erode. Erosion of the electrodes (also referred to as degradation) can then limit the duration of the treatment because once the erosion proceeds too far, the electrodes will no longer generate shockwaves and/or cavitation bubbles that are capable of treating lesions. Thus, prolonging the life of the electrodes is a paramount concern for electrode assemblies used in catheters to calcified occlusions (e.g., lesions). Moreover, ensuring that the erosion proceeds in a relatively controlled manner is also a paramount concern, because largely asymmetrical erosion can severely shorten the usable duration of the electrodes.

In one embodiment, the above goals are realized in a catheter that includes an electrode assembly formed from concentric conductive metal sheaths separated by an insulating layer. Shock waves and/or cavitation bubbles are formed across the distal side edges of the conductive sheaths, which act as electrodes of an electrode pair, causing the distal side edges to slowly degrade over time. The distal side edges of the conductive sheaths are shaped such that the degradation proceeds in a semi-controlled manner and is more evenly distributed around the circumference of the conductive sheaths. This increases the longevity of the electrode assembly, allowing for longer duration treatments with a catheter.

An exemplary embodiment provides a catheter for treating an occlusion in a body lumen. The catheter includes an elongated tube and a cylindrical inner conductive sheath mounted within the elongated tube. The inner conductive sheath has a distal side edge. A cylindrical outer conductive sheath is mounted circumferentially around the inner conductive sheath within the elongated tube. The outer conductive sheath has a distal side edge proximal to the distal side edge of the inner conductive sheath. An insulation sheath is mounted within the elongated tube between the outer conductive sheath and the inner conductive sheath. When a voltage pulse is applied across the inner conductive sheath and the outer conductive sheath, current flows across an arcing region between the inner conductive sheath and the outer conductive sheath to generate cavitation bubbles and/or shock waves, which can be used to treat an occlusion in a body lumen.

In a further embodiment, provided herein is a catheter system comprising an electrode assembly that includes a conductive sheath mounted within the catheter, an insulation sheath circumferentially mounted within the conductive sheath, and a flat coil disposed on an inner surface of the insulation sheath. In one or more examples, the conductive sheath and the flat coil can form the electrodes of an electrode pair such that when a voltage is applied to the electrode assembly, current travels between the flat coil and the conductive sheath. As the current travels, an arcing region can appear at the shortest distance between the flat coil and the conductive sheath. At the arcing region, shockwave and/or cavitation bubbles can be created. Thus, in one or more examples, when a voltage pulse is applied across the flat coil and the conductive sheath of the electrode assembly, cavitation bubbles and/or shockwaves can be generated, which can be used to treat an occlusion in a body lumen.

One embodiment of the present disclosure can have a catheter for treating an occlusion in a body lumen, where that catheter includes: an elongated tube; a cylindrical inner conductive sheath mounted within the elongated tube, the inner conductive sheath having a distal side edge; a cylindrical outer conductive sheath mounted circumferentially around the inner conductive sheath within the elongated tube, the outer conductive sheath having a distal side edge proximal to the distal side edge of the inner conductive sheath; and an insulation sheath mounted within the elongated tube between the outer conductive sheath and the inner conductive sheath; where when a voltage pulse is applied across the inner conductive sheath and the outer conductive sheath, current flows across an arcing region between the inner conductive sheath and the outer conductive sheath to generate cavitation bubbles and/or shock waves. In some aspects, the elongated tube includes a fluid lumen for flowing conductive fluid along the catheter and through a fluid outflow port at a distal end of the catheter. In such aspects, the outer conductive sheath, the insulation sheath, and the inner conductive sheath are mounted within the fluid lumen such that fluid flowing through the fluid lumen flows through the inner conductive sheath. In other aspects, the elongated tube includes an aspiration lumen for removing debris from the body lumen and in optional aspects also includes a guidewire lumen sized to receive a guidewire. In further aspects, the arcing region is located where the distal side edge of the outer conductive sheath is closest to the distal side edge of the inner conductive sheath. In such aspects, where generating cavitation bubbles and/or shock waves causes the distal side edge of the inner conductive sheath to erode proximate to the arcing region, and the erosion of the inner conductive sheath causes current to flow across a secondary arcing region between the distal side edge of the inner conductive sheath and the distal side edge of the outer conductive sheath. In similar aspects, generating cavitation bubbles and/or shock waves causes the distal side edge of the outer conductive sheath to erode proximate to the arcing region, and the erosion of the outer conductive sheath causes current to flow across a secondary arcing region between the distal side edge of the outer conductive sheath and the distal side edge of the inner conductive sheath. In some aspects, when a voltage pulse is applied a positive pressure spike is generated and thereafter a negative pressure spike is generated.

Another embodiment of the present disclosure can have catheter for treating an occlusion in a body lumen, the catheter including: an elongated tube; a cylindrical conductive sheath mounted within the elongated tube, the conductive sheath having a distal side edge; an insulation sheath mounted circumferentially within the conductive sheath, the insulation sheath having a distal side edge proximal to the distal side edge of the conductive sheath; a flat coil disposed on an inner surface of the insulation sheath, the flat coil having a distal end proximal to the distal side edge of the conductive sheath and the distal side edge of the insulation sheath; and where when a voltage pulse is applied across the flat coil and the conductive sheath, current flows across an arcing region between the flat coil and the conductive sheath to generate cavitation bubbles and/or shock waves. In some aspects, the flat coil has a rectangular cross-section with a planar inner surface on a side opposite the inner surface of the insulation sheath. In other aspects, the elongated tube comprises a fluid lumen for flowing conductive fluid along the catheter and through a fluid outflow port at a distal end of the catheter, and the conductive sheath, the insulation sheath, and the flat coil can all be mounted within the fluid lumen such that fluid flowing through the fluid lumen flows through the flat coil. In further aspects, the arcing region is located where the distal side edge of the conductive sheath is closest to the distal end of the flat coil. In such aspects, generating cavitation bubbles and/or shock waves causes the insulation sheath to erode proximate to the arcing region, and the erosion of the insulation sheath exposes an outer surface of the flat coil causing current to flow across a secondary arcing region between the outer surface of the flat coil and the distal side edge of the conductive sheath. Similarly, generating cavitation bubbles and/or shock waves causes the distal side edge of the conductive sheath to erode proximate to the arcing region, and the erosion of the conductive sheath begins before the erosion of the insulation sheath begins. In some aspects, the elongated tube includes an aspiration lumen for removing debris from the body lumen, and in optional aspects the elongated tube includes a guidewire lumen sized to receive a guidewire. In alternative aspects, the flat coil is constructed with one or more cross ties extending along a length of the flat coil between each coil of the flat coil. In other aspects, an adhesive is disposed in an area between coils of the flat coil on an inner surface of the insulation sheath, where the adhesive fills the area between the coils and secures the flat coil to the insulation sheath. In further aspects, when the voltage pulse is applied, a positive pressure spike is generated and thereafter a negative pressure spike is generated.

BRIEF DESCRIPTION OF THE FIGURES

Illustrative aspects of the present disclosure are described in detail below with reference to the following drawing figures. It is intended that that embodiments and figures disclosed herein are to be considered illustrative rather than restrictive.

FIG. 8A illustrates a left side cross-sectional view of an exemplary electrode assembly of a catheter, such as the electrode assembly of FIG. 6, according to aspects of the present disclosure.

FIG. 8B illustrates a front view of an exemplary electrode assembly of a catheter, such as the electrode assembly of FIG. 6, according to aspects of the present disclosure.

FIG. 8C illustrates an enlarged and more detailed cross-sectional view of the degraded distal side edge of the exemplary electrode assembly of FIG. 8A, according to aspects of the present disclosure.

FIG. 11A illustrates a left side cross-sectional view of the exemplary electrode assembly of a catheter shown in FIG. 10, according to aspects of the present disclosure.

FIG. 11B illustrates a front view of the exemplary electrode assembly of a catheter shown in FIG. 10, according to aspects of the present disclosure.

FIG. 11C illustrates an enlarged and more detailed cross-sectional view of the degraded distal side edge of the exemplary electrode assembly of FIG. 11A, according to aspects of the present disclosure.

FIG. 15A illustrates a top side cross-sectional view of the distal end of the exemplary catheter shown in FIG. 14B, according to aspects of the present disclosure.

7

Figure 14A:
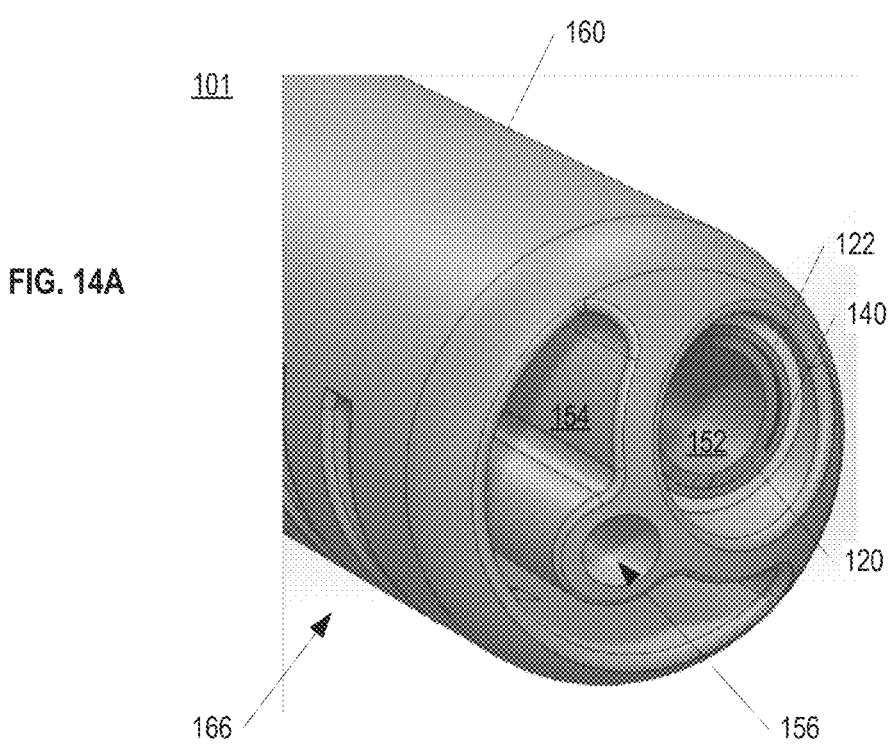
FIG. 14A illustrates a perspective view of the distal end of an exemplary catheter having a guidewire lumen, according to aspects of the present disclosure.
Figure 14B:
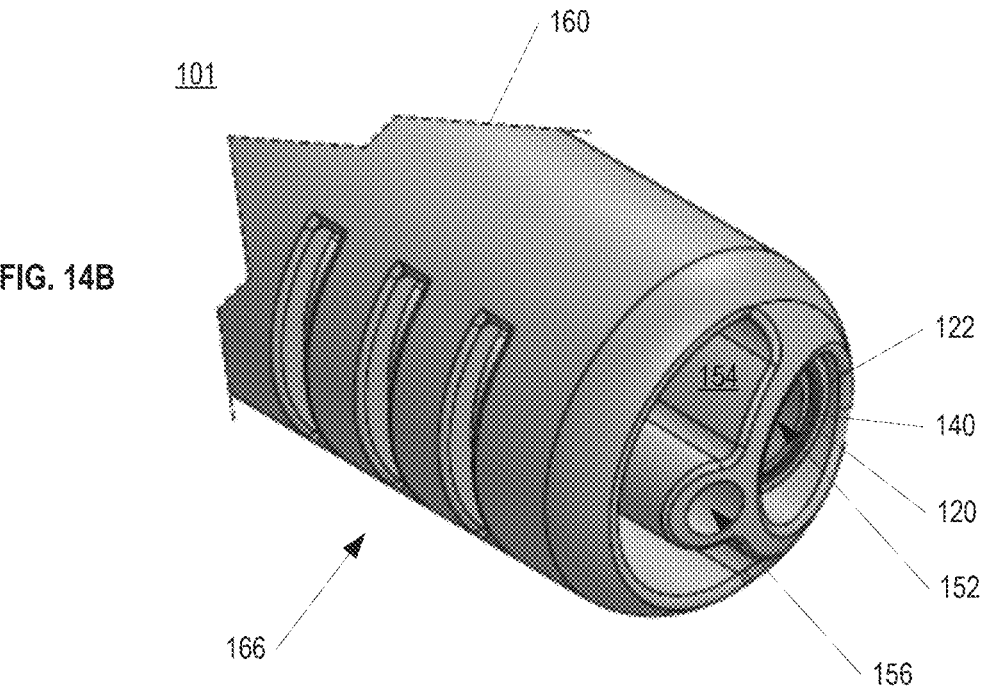
FIG. 14B illustrates a perspective view of the distal end of an exemplary catheter having a guidewire lumen, according to aspects of the present disclosure.

FIG. 15B illustrates a left side view of the distal end the exemplary catheter shown in FIG. 14B, according to aspects of the present disclosure.

FIG. 15C illustrates a front view the distal end of the exemplary catheter shown in FIG. 14B, according to aspects of the present disclosure.

Figure 3:
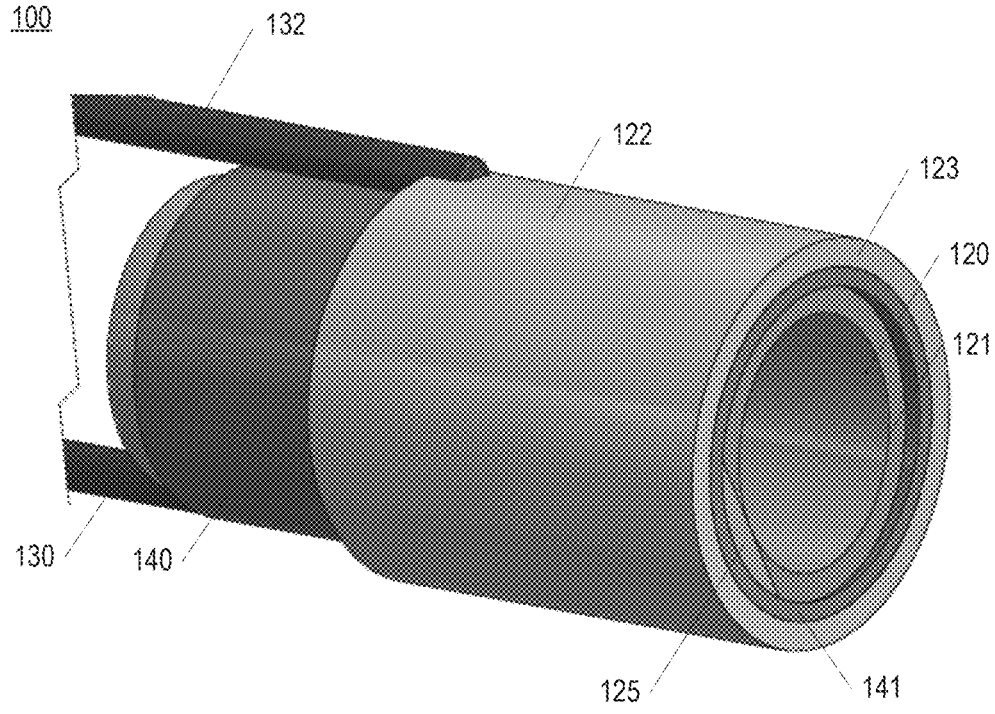
FIG. 3 illustrates a perspective view of an exemplary electrode assembly of a catheter, according to aspects of the present disclosure.
Figure 16:
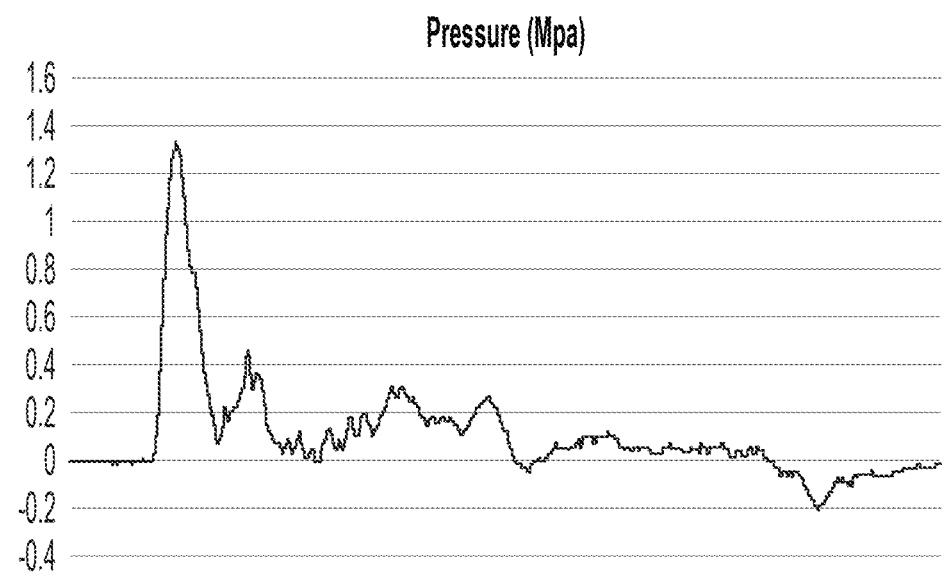

FIG. 16 is a graph showing measurements of pressure generated by a device fabricated in accordance with FIGS. 3 to 5.

Figure 17:
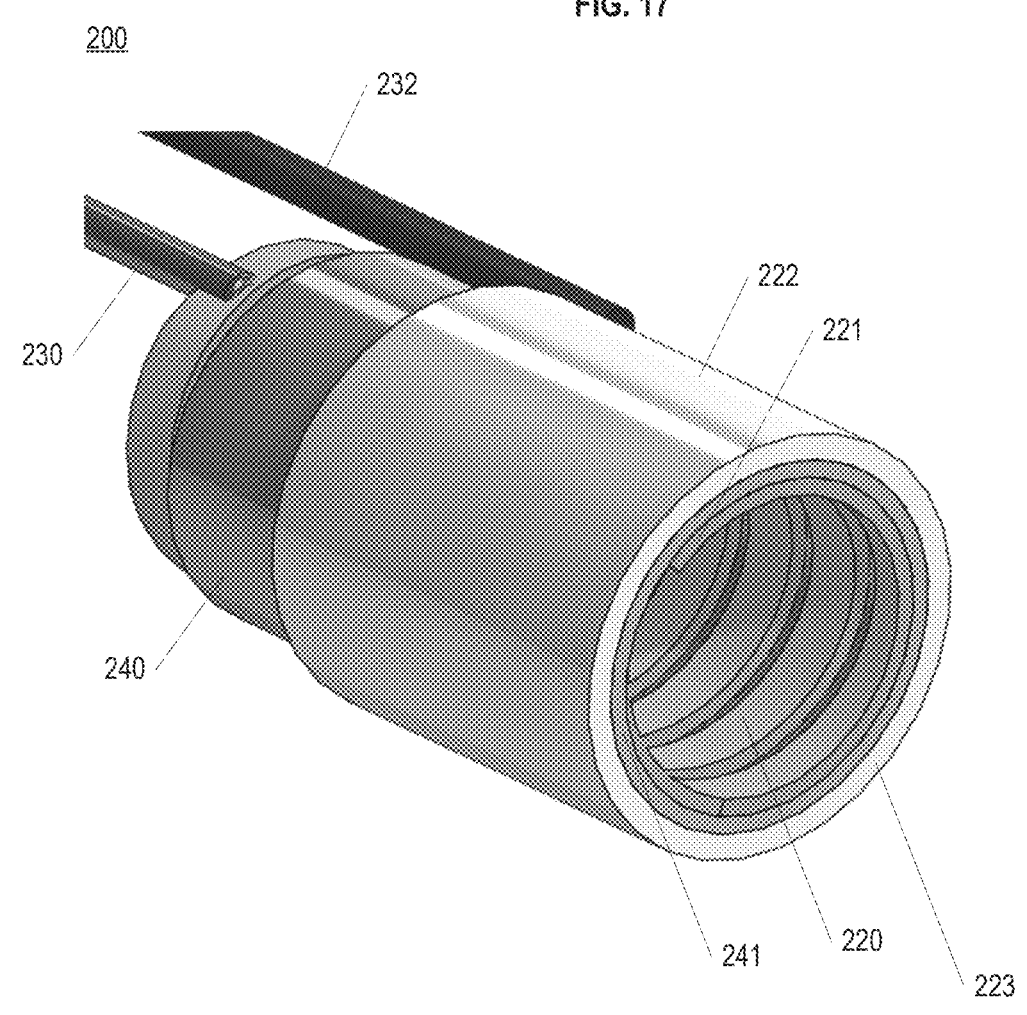

FIG. 17 illustrates a perspective view of an exemplary electrode assembly of a catheter, according to aspects of the present disclosure.

Figure 18:
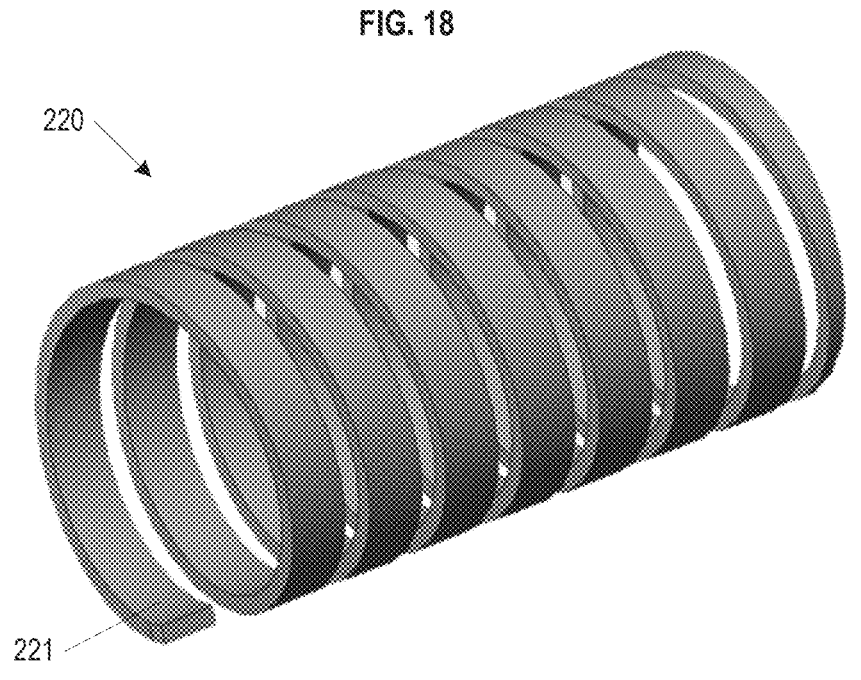

FIG. 18 illustrates a perspective view of an exemplary flat coil of an electrode assembly, according to aspects of the present disclosure.

Figure 19:
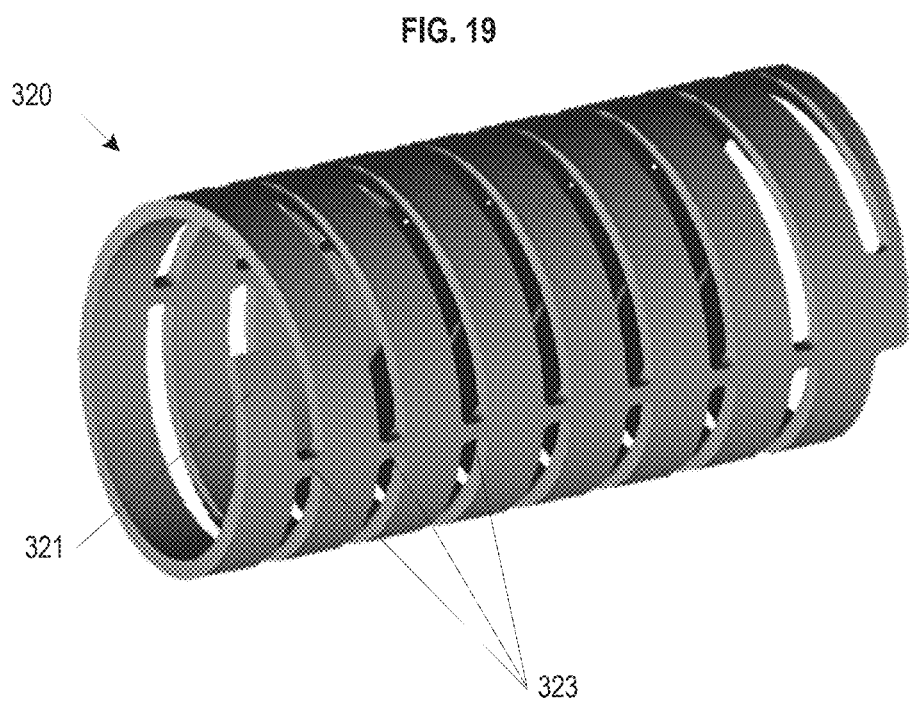

FIG. 19 illustrates a perspective view of an exemplary flat coil with cross ties of an electrode assembly, according to aspects of the present disclosure.

Figure 20:
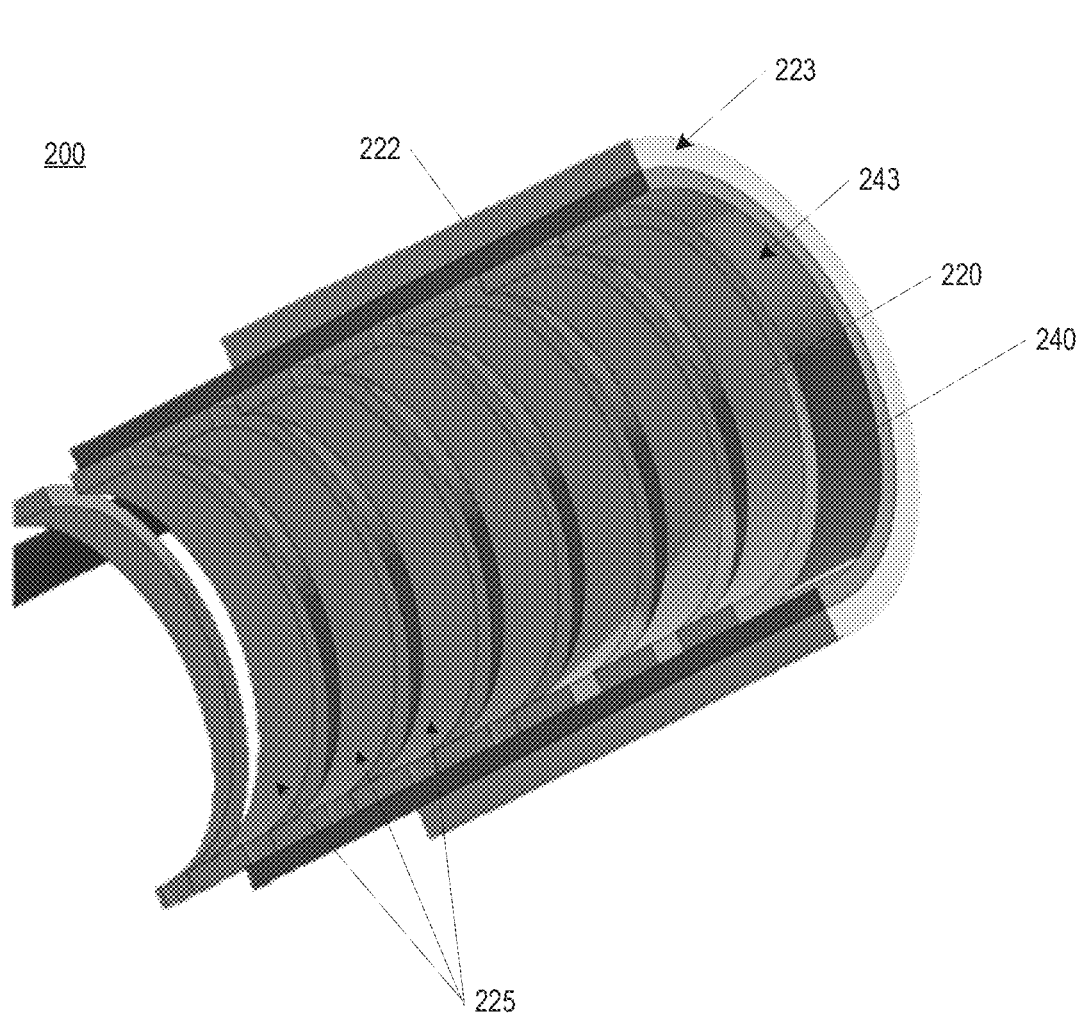

FIG. 20 illustrates a perspective cross-sectional view of an exemplary electrode assembly of a cathode, according to aspects of the present disclosure.

Figure 21A:
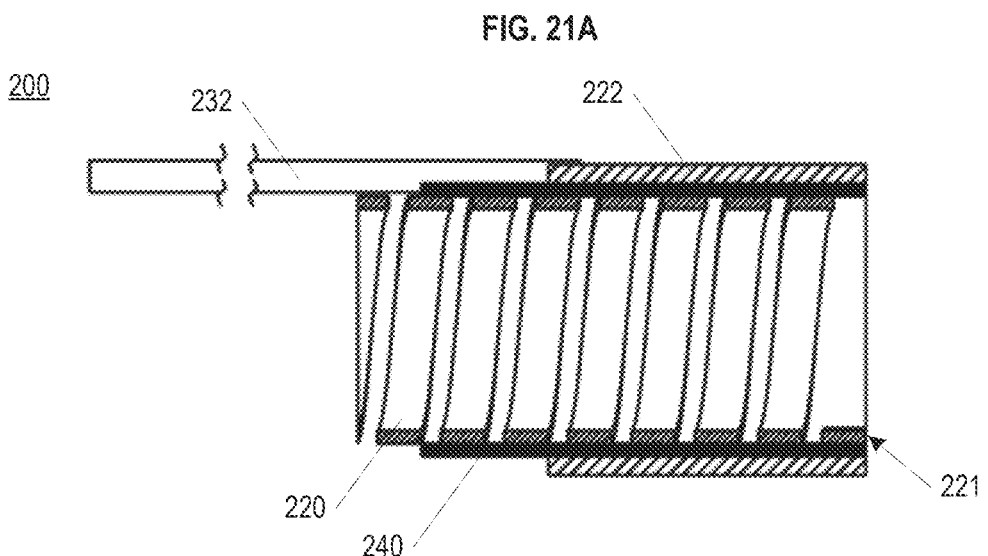

FIG. 21A illustrates a left side cross-sectional view of an exemplary electrode assembly of a catheter, according to aspects of the present disclosure.

Figure 21B:
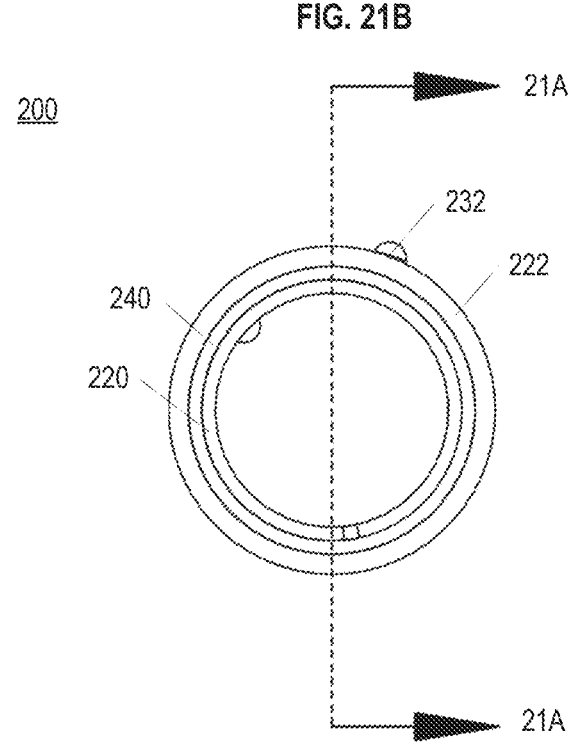

FIG. 21B illustrates a front view of the exemplary electrode assembly of FIG. 21A, according to aspects of the present disclosure.

Figure 22:
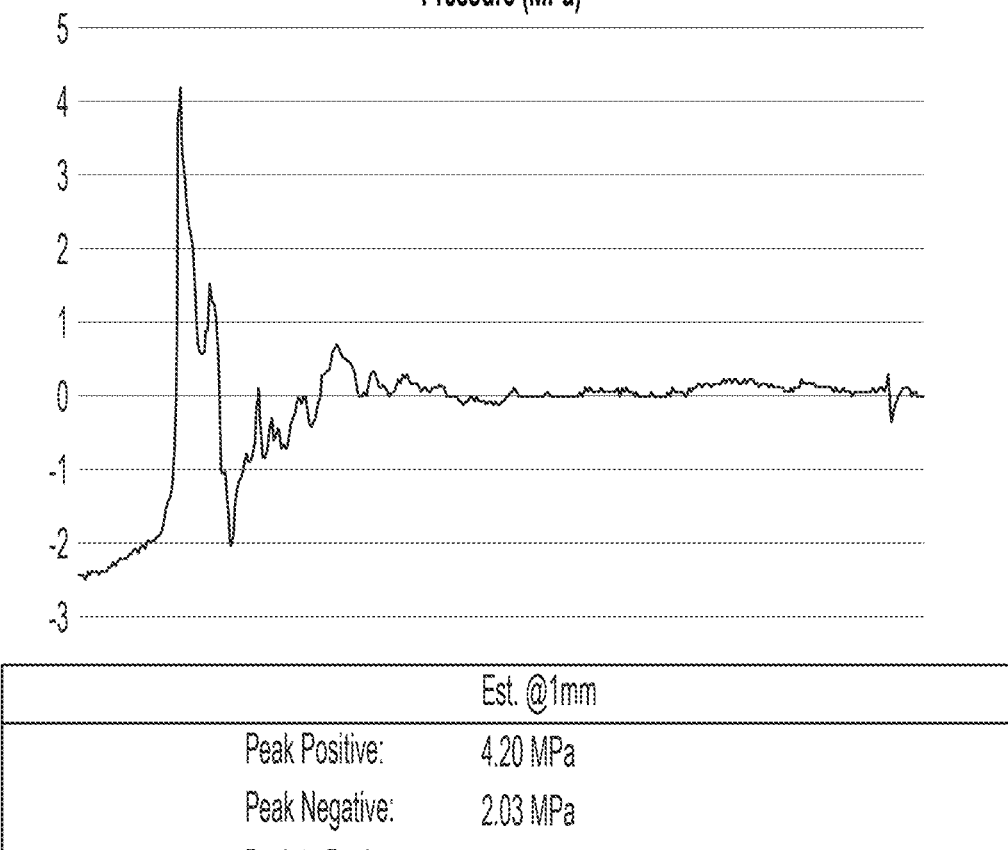

FIG. 22 is a graph showing measurements of pressure generated by a device fabricated in accordance with FIG. 17.

Figure 23:
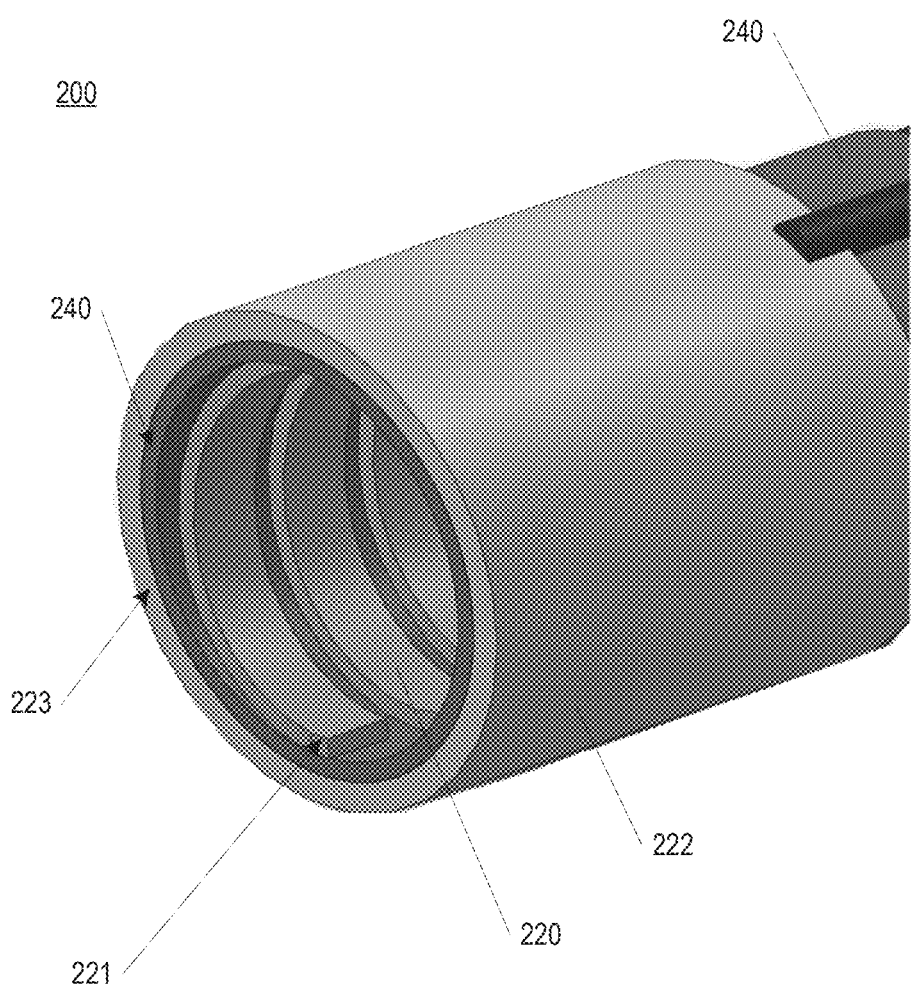

FIG. 23 illustrates a perspective view of the exemplary electrode assembly of FIG. 17 before any erosion, according to aspects of the present disclosure.

Figure 24A:
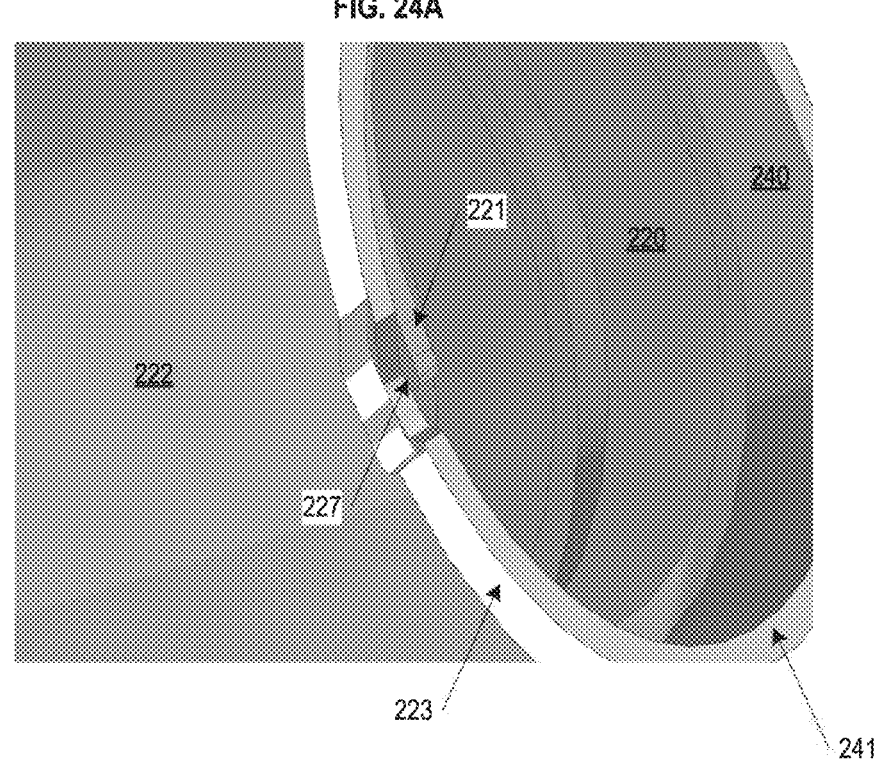

FIG. 24A illustrates an enlarged detail view of the eroded distal side edge of the exemplary electrode assembly of FIG. 17, according to aspects of the present disclosure.

Figure 24B:
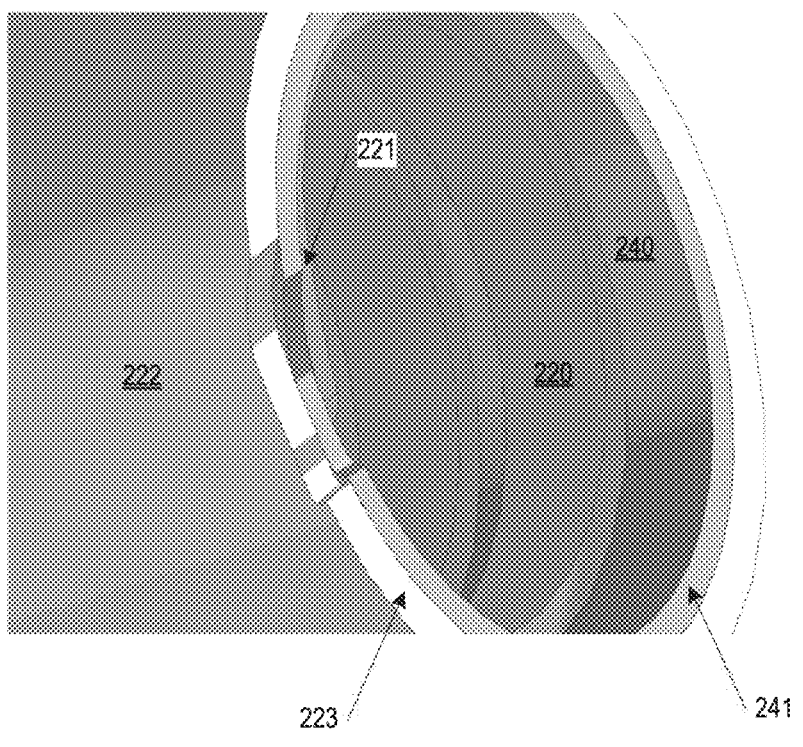

FIG. 24B illustrates an enlarged detail view of the eroded distal side edge of the exemplary electrode assembly of FIG. 17 as the erosion expands, according to aspects of the present disclosure.

Figure 25A:
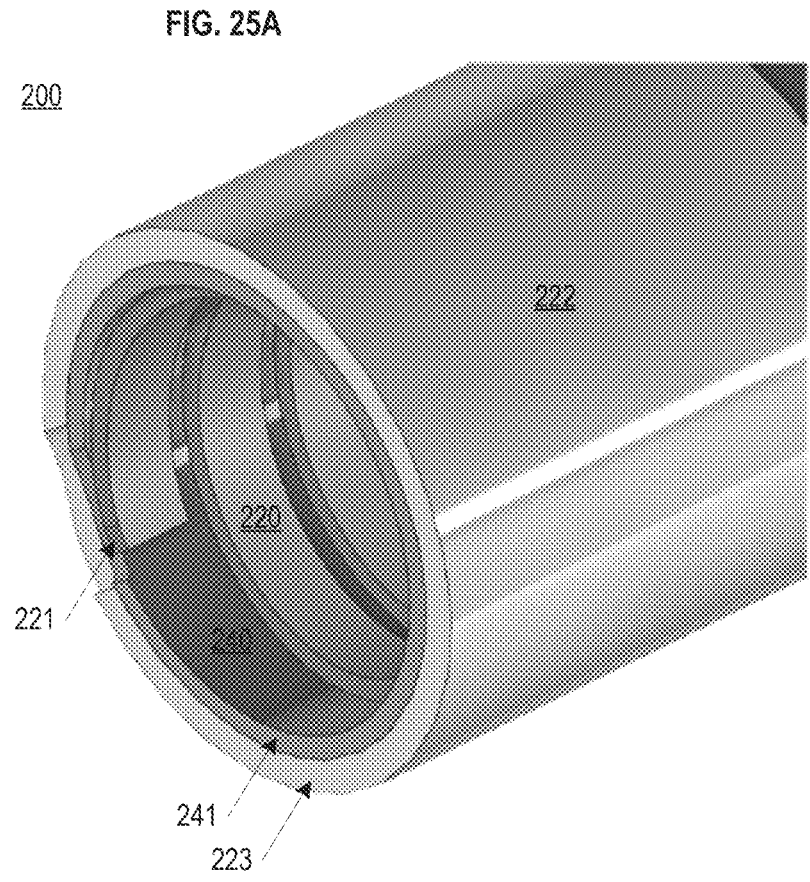

FIG. 25A illustrates a perspective view of the exemplary electrode assembly of FIG. 17 after initial erosion caused by the generation of a series of shock waves and/or cavitation bubbles, according to aspects of the present disclosure.

Figure 25B:
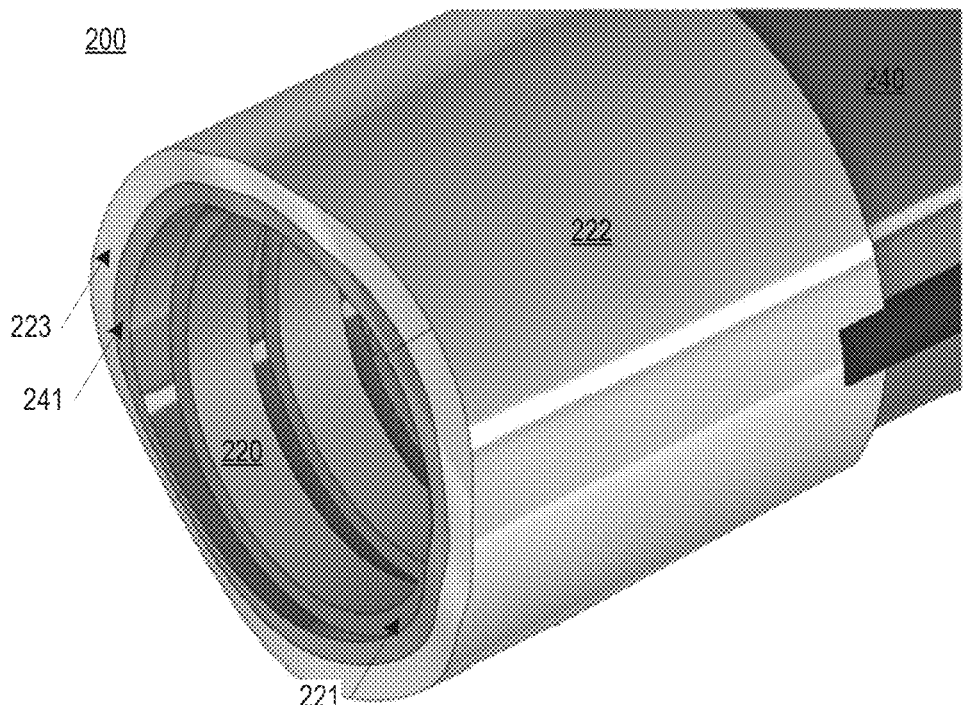

FIG. 25B illustrates a perspective view of the exemplary electrode assembly of FIG. 17 after extensive erosion caused by the generation of a series of shock waves and/or cavitation bubbles, according to aspects of the present disclosure.

Figure 26:
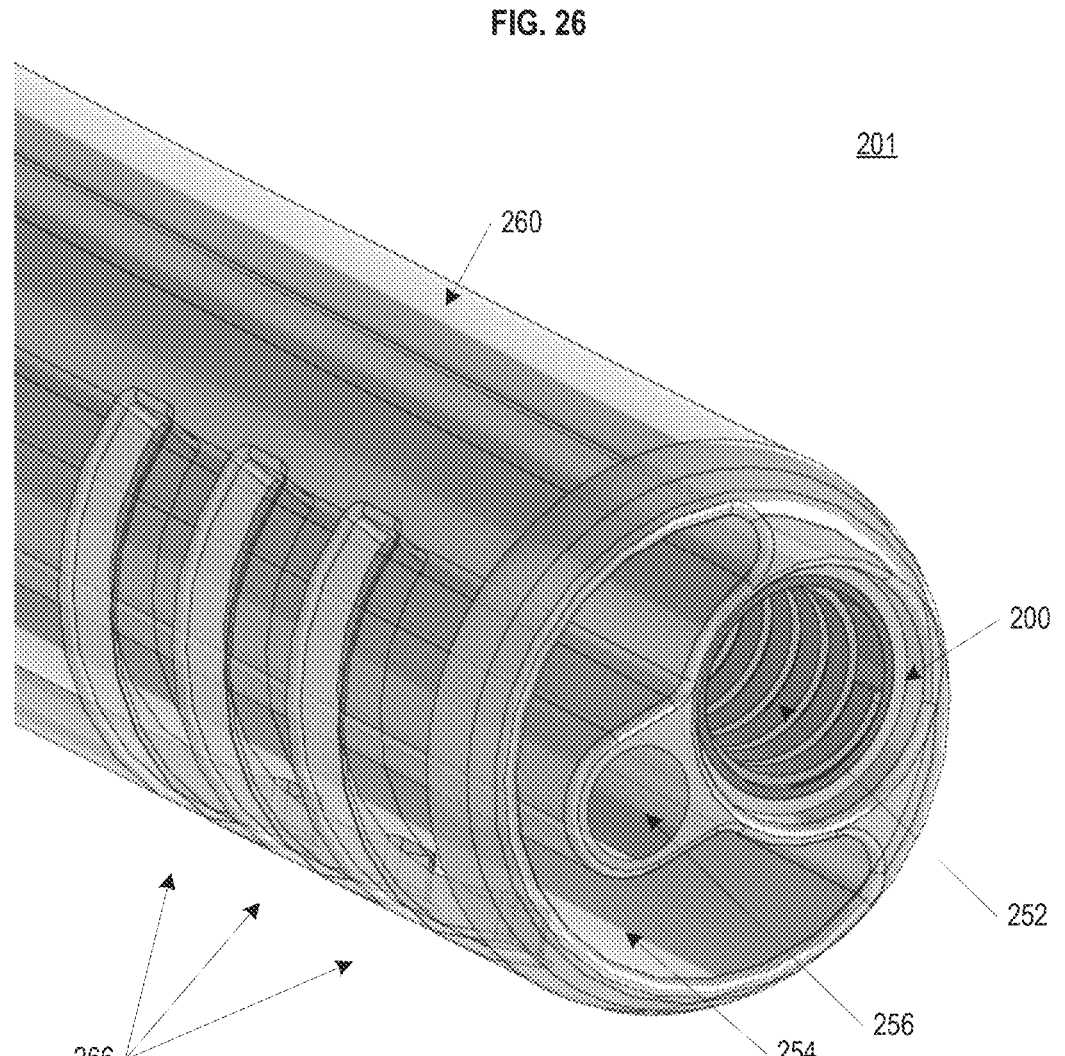

FIG. 26 illustrates a perspective view of the distal end of an exemplary catheter according to aspects of the present disclosure.

Figure 27A:
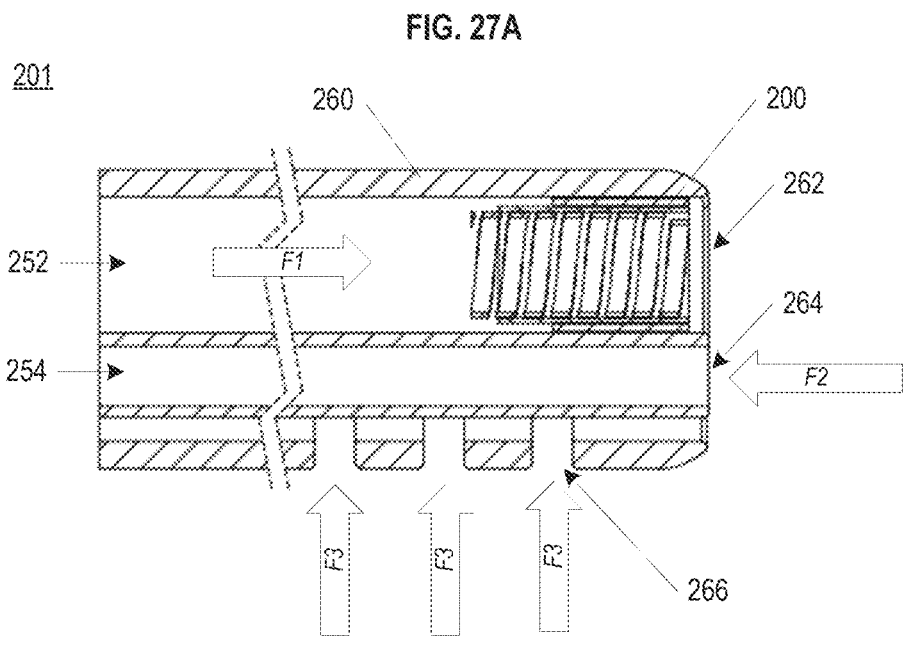

FIG. 27A illustrates a left side cross-sectional view of the distal end of an exemplary catheter, according to aspects of the present disclosure.

Figure 27B:
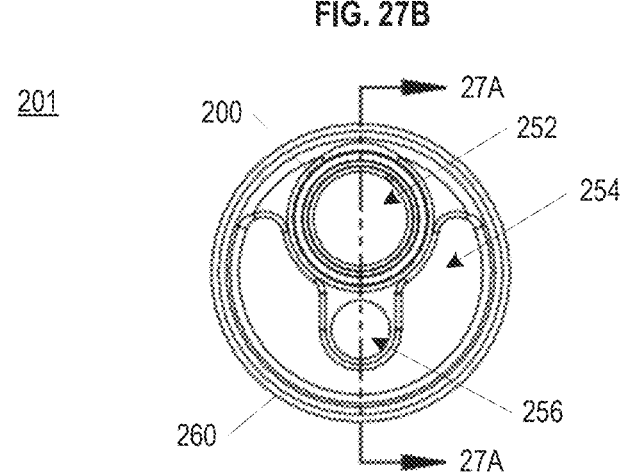

FIG. 27B illustrates a front view of the distal end of an exemplary catheter, according to aspects of the present disclosure.

Figure 28A:
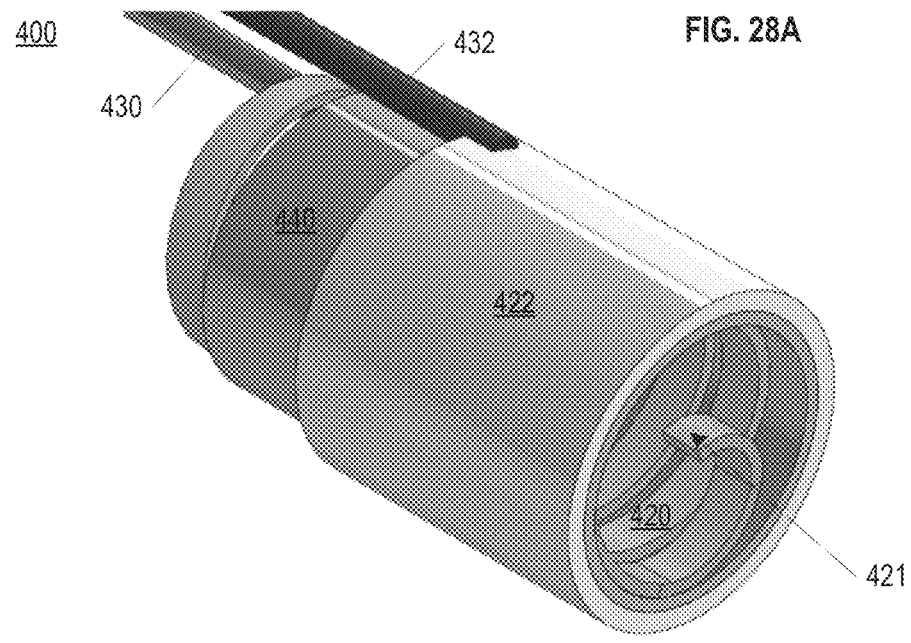
Figure 28B:
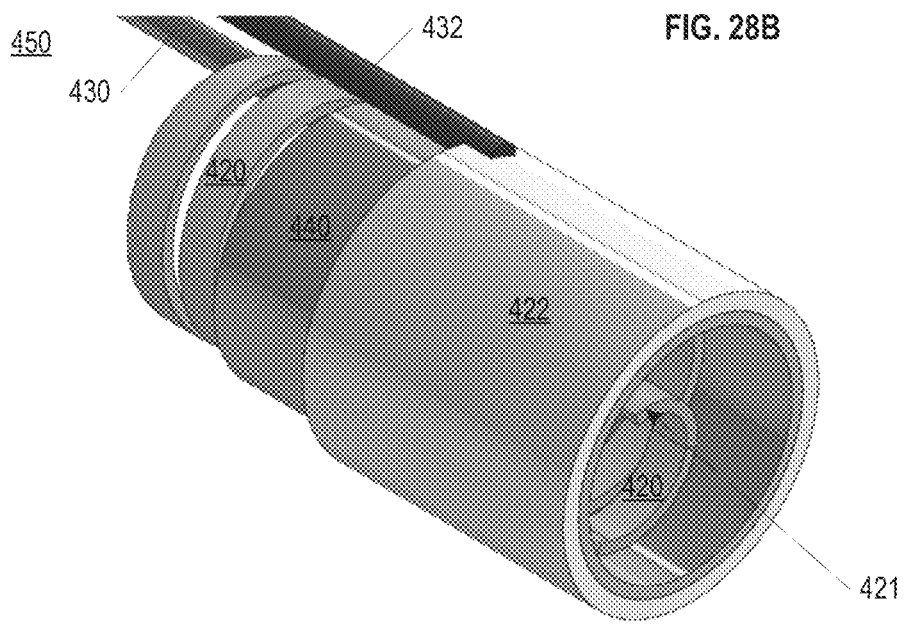

FIGS. 28A and 28B illustrate perspective views of exemplary electrode assemblies having an interior coiled electrode with a curved distal tip, according to aspects of the present disclosure.

Figure 29:
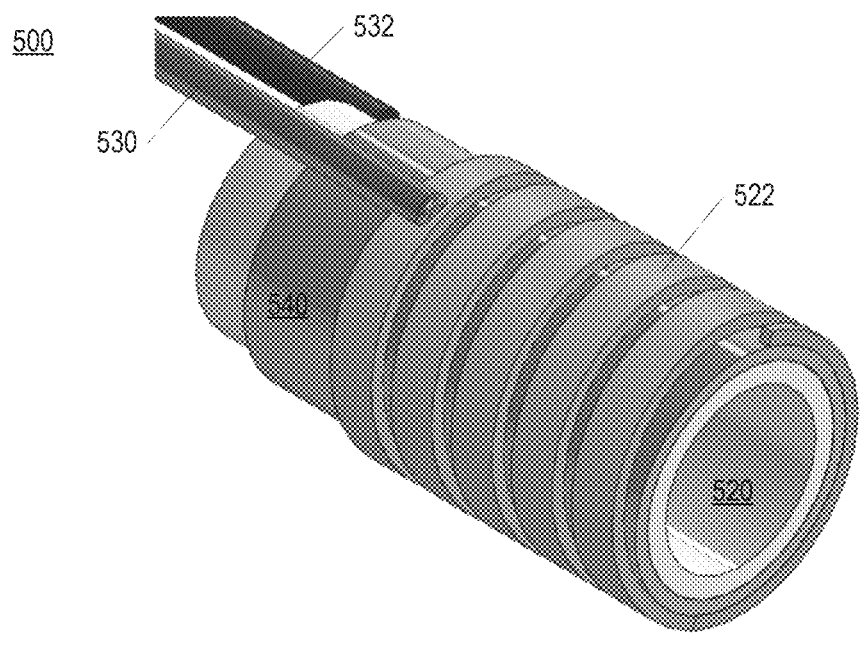

FIG. 29 illustrates a perspective view of an exemplary electrode assembly having an exterior coiled electrode and a solid tube interior electrode, according to aspects of the present disclosure.

Figure 30:
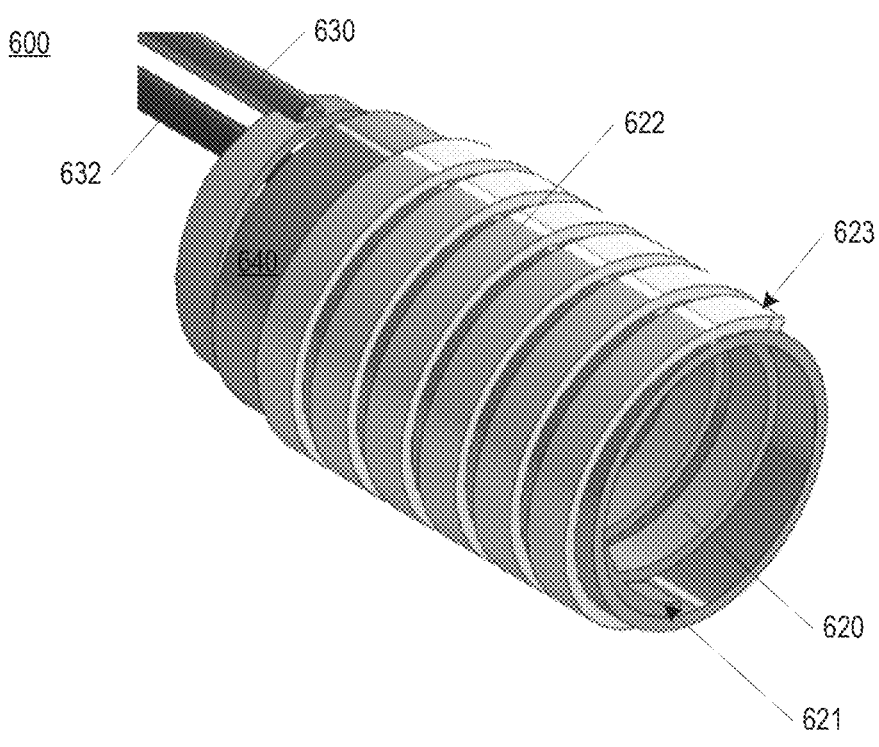

FIG. 30 illustrates a perspective view of an exemplary electrode assembly having an exterior clockwise coiled electrode and an interior counterclockwise coiled electrode, according to aspects of the present disclosure.

Figure 31A:
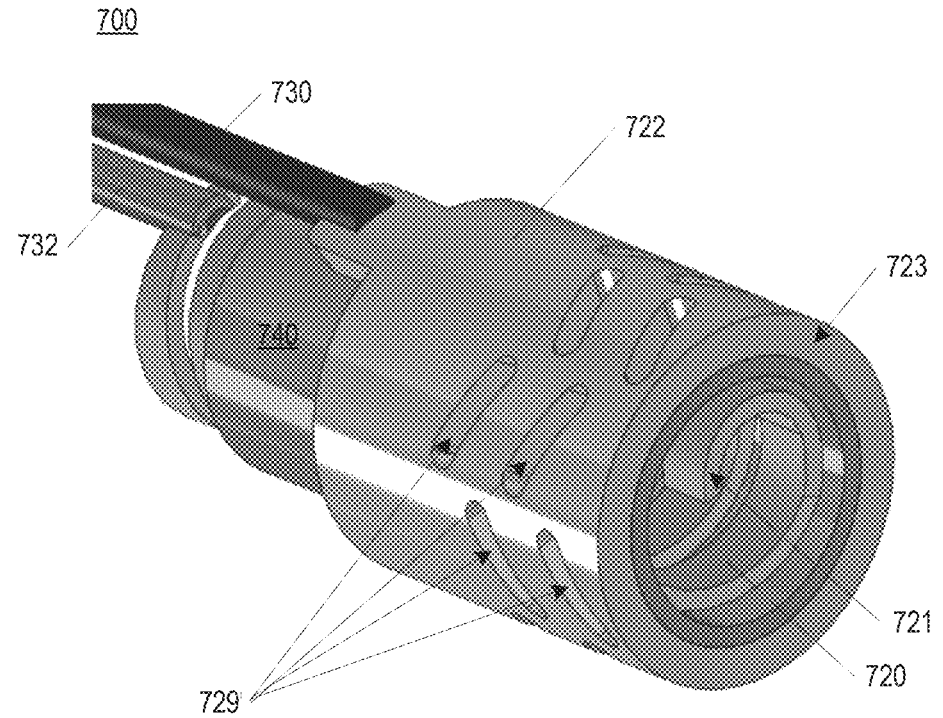

FIG. 31A illustrates a perspective view of an exemplary electrode assembly having an exterior electrode having cut-out patterning, according to aspects of the present disclosure.

FIGS. 31B through 31E illustrate an exemplary progression of electrode degradation for an electrode having cut-out patterning as shown in FIG. 31A, according to aspects of the present disclosure.

FIGS. 32A through 32H, are captured images from a high-speed video showing an exemplary electrode assembly generating a forward-directional vapor bubble, according to aspects of the present disclosure.

DETAILED DESCRIPTION

The following description is presented to enable a person of ordinary skill in the art to make and use the various embodiments disclosed herein. Descriptions of specific devices, assemblies, techniques, and applications are provided only as examples. Various modifications to the examples described herein will be readily apparent to those of ordinary skill in the art, and the general principles described herein may be applied to other examples and applications without departing from the spirit and scope of the various embodiments. Thus, the various embodiments are not intended to be limited to the examples described herein and shown, but rather are to be accorded the scope consistent with the claims.

Described herein are catheters incorporating design elements that improve the lifespan of an electrode assembly, allowing for longer duration shock wave and cavitation treatments. As shock waves and/or cavitation bubbles are generated across an electrode pair, the electrode surface slowly erodes at the location where current flows between the electrodes (i.e., at an "arcing region" between the electrodes of a pair). Once an initial arcing region has been eroded and the distance between the electrodes at the initial arcing region increases, current may begin to flow from an undesirable secondary arcing region or may cease to flow entirely, such that shock waves and/or cavitation bubbles are no longer generated. Over the course of a treatment, the electrodes may erode and degrade in a non-uniform manner that limits the usable lifespan of the electrode assembly. For instance, when the electrodes are formed from insulated wires or other narrow conductive materials with a relatively small conductive surface area, erosion of the electrodes advances quickly and can result in the early termination of a shock wave procedures. Other catheter designs may include electrodes that are a uniform distance apart across their surfaces, causing degradation to proceed in a stochastic manner that results in uncontrolled and uneven degradation across the electrode surface. Another electrode design can be formed from two cylindrical conductive metal sheaths mounted concentrically within a catheter, which can demonstrate a longer lifespan than insulated wire electrode designs. However, as the lifespan of the electrode design directly impacts treatment duration, increasing the lifespan of the electrodes is desirable.

To increase the lifespan of an electrode assembly, in some of the implementations described herein, the electrode assemblies have been shaped such that degradation proceeds in a predictable or semi-controlled manner across the surface area of an electrode. In particular, the electrode pairs of the assemblies are shaped such that certain portions of the electrode surfaces are closer in distance, while other portions are farther apart. Accordingly, when a voltage is applied across the electrode pairs, current initially flows across an initial arcing region where the electrodes are closest in distance. Once the electrode surface erodes at the initial arcing region, current begins to flow across a secondary arcing region that provides a new least-resistance (i.e., closest distance) path between the electrodes. As the treatment continues, successively farther-distance portions will begin to degrade as the arcing region moves across the remaining surface area of the electrode.

To increase the lifespan of an electrode assembly, in other implementations described herein, the assemblies can incorporate a flat uninsulated helical electrode. The flat helical electrode can have a larger cross-sectional area relative to round wires, which can ensure the flat helical electrode has a lower resistance and thus supplies a higher current flow to the arcing region. Relative to an electrode pair with two concentric conductive sheaths, the flat helical electrode can generate usable cavitation for a longer duration, thereby enabling longer shockwave and cavitation treatments. Further, the use of a flat helical electrode can improve manufacturability of the electrode assemblies.

Depending on the shape of the electrodes, the location of the initial and further arcing regions can be configured to be relatively predictable or predetermined. For instance, by providing a gradual slope along the surface of the electrode, or a series of notches, waves, or other shapes along the electrode surface, certain portions of an electrode surface can be placed a predetermined distance from a corresponding electrode of a pair. Through the course of a procedure, the surface of the electrodes degrades in a semi-controlled manner according to the relative distance between the electrodes of the pair, beginning with closest distance portion of the electrode surface (i.e., the initial arcing region), and continuing to successively farther portions of the electrode surface. This results in more even erosion across the electrode surface and increased longevity of an electrode assembly, allowing for longer duration shock wave and/or cavitation treatments.

The catheter designs described herein may be similar to current shock wave catheters in that they include at least one electrode pair within the working length of a catheter that delivers acoustic shock waves and/or cavitation bubbles to a treatment site proximate to the catheter's distal tip. For instance, as described in U.S. Pat. No. 10,709,462, incorporated herein by reference, a first electrode of a catheter can be formed from a side edge of a conductive metal sheath mounted within the catheter. An electrode pair can be formed by positioning a second conductive material a controlled distance (i.e., a gap) apart from the conductive sheath to allow for a reproducible arc across the electrodes for a given current and voltage. In some examples, as described in the above reference, a second electrode of an electrode pair can be formed by from an electrically conductive portion (e.g., an insulation-removed portion) of a wire extending along the length of the catheter. Additionally or alternatively, as described herein, an exemplary electrode pair can be formed from two cylindrical conductive metal sheaths mounted concentrically within a catheter. Such an electrode assembly may have a relatively smaller crossing profile compared to existing electrode assembly designs, for instance, with a crossing profile between 0.8 mm to 1.2 mm in diameter. Such an electrode assembly design may also facilitate manufacturing of a catheter by simplifying the process for constructing the electrode assembly.

As provided herein, it should be appreciated that any disclosure of a numerical range describing dimensions or measurements such as thicknesses, length, weight, time, frequency, temperature, voltage, current, angle, etc. is inclusive of any numerical increment or gradient within the ranges set forth relative to the given dimension or measurement.

Figures 1A, 1B, 1C, 1D, 1E, 1F, 1G:
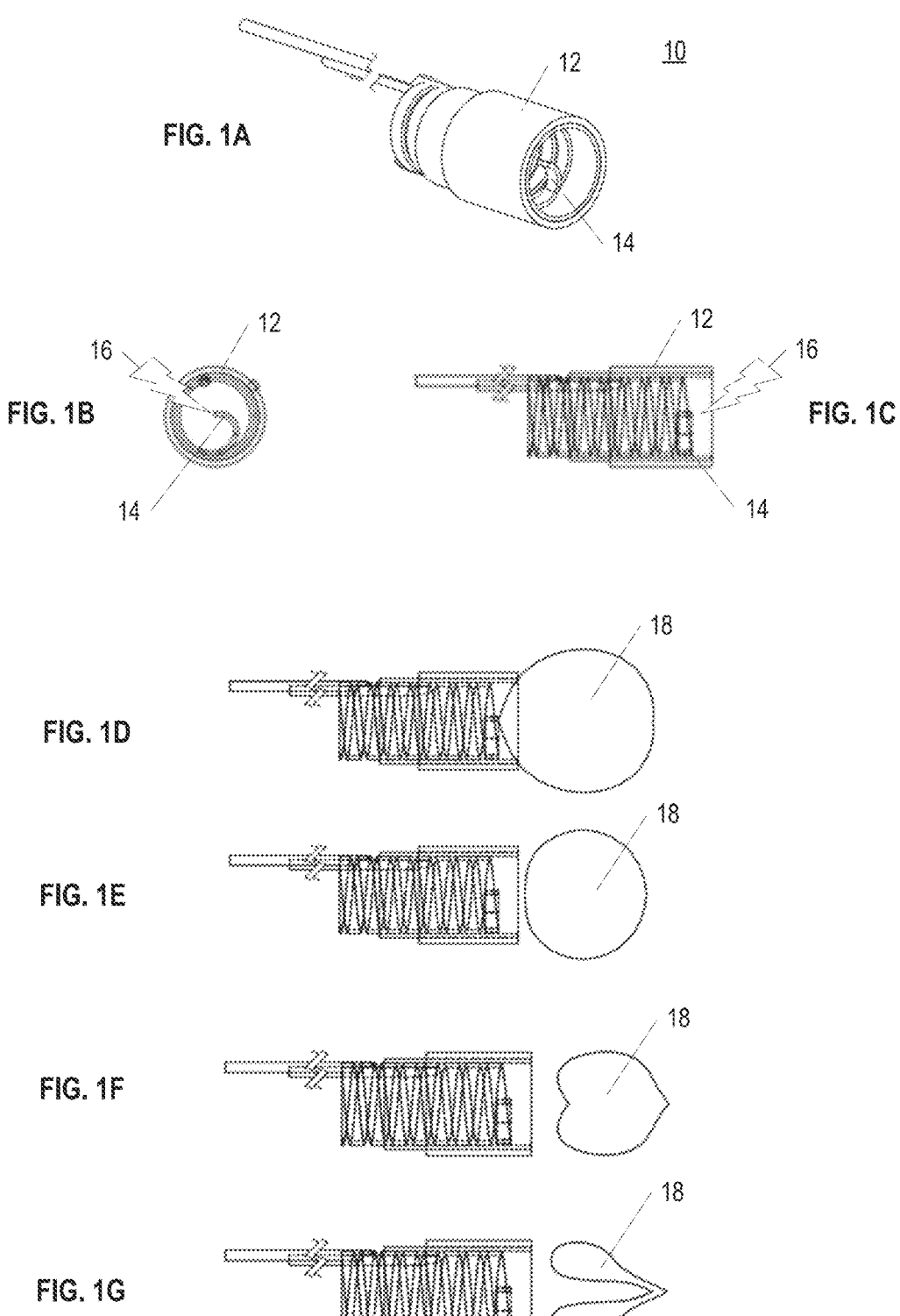
FIGS. 1A-1G illustrate a mode of action for generating forward-firing cavitation bubbles using electrode assemblies, according to aspects of the present disclosure.

FIGS. 1A-1G illustrate a mode of action for generating forward-firing cavitation bubbles using electrode assemblies. An exemplary electrode assembly 10 is illustrated in perspective view in FIG. 1A having an outer electrode 12 and an inner electrode 14, and is understood to be submerged within a conductive fluid. It should be appreciated that in other implementations and variations, the electrodes of an electrode assembly may be configured in different orientations, different shapes, or present different profiles relative to each other. FIB. 1B illustrates the electrode assembly 10 in a front view and FIG. 1C illustrates the electrode assembly in a cross-sectional side profile view. Both FIGS. 1B and 1C further illustrate the location of an electrical spark 16, which can be generated in the gap between outer electrode 12 and inner electrode 14 when energy is applied across the paired electrodes of the electrode assembly 10. Depending on the polarity of the power source, the current driven to the electrode assembly 10 can travel from the inner electrode 14 across to the outer electrode 12, or vice versa. The electrical spark 16 formed by the electrode assembly causes a vapor bubble 18 to form within the conductive fluid.

FIGS. 1D through 1G illustrate the expansion and collapse of the vapor bubble 18 generated by the electrical spark 16. In FIG. 1D, approximately 250-280 µs after the occurrence of the electrical spark 16, the vapor bubble 18 forms and expands originating from the location of the electrical spark 16. At least in part due to the arrangement of the inner electrode 12 and the outer electrode 14 relative to each other, the expansion of vapor bubble 18 is directed distally from the open end of the electrode assembly 10. In particular as shown in this example, the cylindrical walls of the electrode assembly 10 and the outer electrode 14 constrain the initial expansion space of the vapor bubble 18, directing the vapor bubble 18 outward and distal direction (relatively forward) away from the electrode assembly 10. Further, the position of the inner electrode 12 within the structure of the electrode assembly 10 centralizes the origin point for expansion of the vapor bubble 18, reducing any bias away from a longitudinal centerline of the electrode assembly 10. In other words, the vapor bubble 18 starts expanding in the middle of the electrode assembly cylinder, and accordingly continues to expand in a direction relatively outward and distal (forward) from the end of the electrode assembly.

The progression in the change of the shape of the vapor bubble 18, the expansion and collapse of the vapor bubble 18, further shows the mode of action for implementations of the present disclosure. In FIG. 1D, the vapor bubble 18 is expanding outward from the origin point of the vapor bubble 18 (i.e., where the electrical spark 16 occurred). In FIG. 1E, the vapor bubble 18 has a relatively more spherical shape and has moved forward away from its origin point. In FIG. 1F, the vapor bubble 18 has moved further forward and has begun collapsing, having a shape that is relatively elliptical, with the vapor bubble 18 impinging inward at its trailing edge and extending to a focal point at its leading edge. In FIG. 1G, the vapor bubble 18 has moved yet further forward away from its origin point and has collapsed with further impingement at its trailing edge to have a wishbone shape. At this point, the leading edge of the vapor bubble 18 is approximately one millimeter (1 mm) in front of the distal end of the electrode assembly. The leading edge of the vapor bubble 18 as shown in FIG. 1G has a focal point that has extended prominently forward, and without being bound to this theory, it is at this extended focal point that a maximum force (approximately 0.5-1.0 N) is exerted by the vapor bubble 18. Accordingly, a surface positioned at the distance where maximum force is exerted by the vapor bubble 18 can be ablated by that force of the vapor bubble 18. For clinical applications considered by the present disclosure, such surfaces can be fibrous tissue, calcified tissue, lesions, or other tissues within a patient body.

The cycle of running energy across the electrodes to generate an electrical spark and a subsequent vapor bubble can be on the order of thirty seconds (30 sec). Accordingly, in some embodiments twenty cycles for a total run time of ten minutes can be run to repeatedly and quickly ablate a target tissue, where the ablation can be characterized as a "chipping away" mode of action. In other embodiments, the frequency of electrical spark generation can be relatively greater, in the range from about 100-200 Hz (e.g., 125 Hz, 150 Hz, 175 Hz, and other increments of frequency within this rage), where the ablation can be characterized as a "woodpecker" mode of action. It should be appreciated that that other exemplary numbers of cycles and total run times can be used to achieve similar ablative effects.

Figure 2:
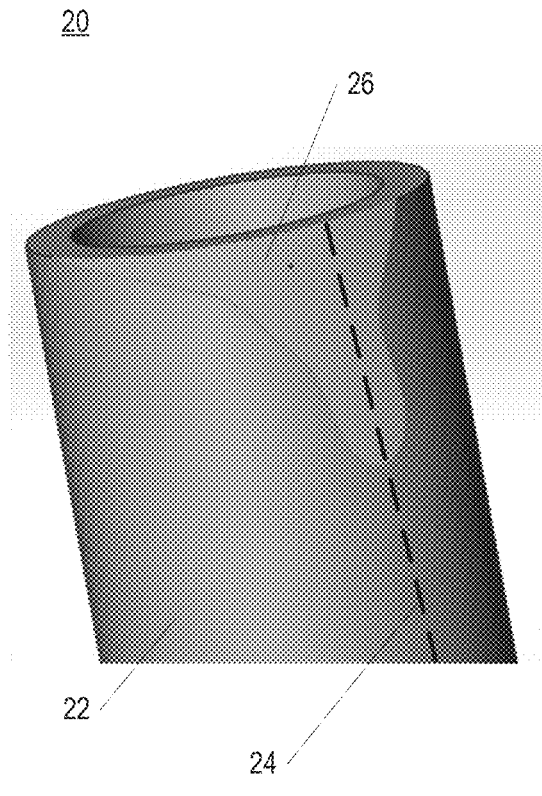
FIG. 2 illustrates an exemplary erosion pattern for the degradation of a cylindrical electrode.

FIG. 2 illustrates an exemplary erosion pattern for the degradation of a cylindrical electrode 20. As illustrated, the cylindrical electrode 20 is formed of a conductive sheet 22 (e.g., a metal or an alloy) that has been rolled into a cylindrical shape. In such constructions, there will often be a scam 24 (shown with a dashed line in FIG. 2) where the edges of the conductive sheet 22 meet to form a cylindrical tube. It is generally observed that electrical current will tend to arc at locations on an electrode where there is a sharp edge or corner; in the context of cylindrical electrode 20, the seam 24 will accordingly present a relatively sharp edge where current will preferentially arc toward and thus primarily erode the conductive sheet 22. Erosion region 26 illustrates an exemplary erosion pattern that tracks along the seam 24 in a longitudinal direction down the length of cylindrical electrode 20, gradually widening and degrading the distal end of cylindrical electrode 20, but ultimately creating an uneven and irregularly shaped electrode edge. Without mitigation, such an irregularly shaped electrode can lead to misfiring of an electrode, and in the context of a shock wave generating device, to the failure to generate shock waves and cavitation bubbles.

There are several differences with the mode of action of both previously implemented IVL applications and the present disclosure in comparison with traditional lithotripsy. In contrast with traditional histotripsy, IVL is not an extracorporeal treatment, leading to substantially different decisions to deliver shock waves in an intravascular environment. Further, histotripsy uses a focused ultrasound that can deliver high intensity short pulses, with energy in the range of 30-50 MPa at a frequency of 500-800 kHz. Moreover, histotripsy typically targets soft tissue, which is not the typical target tissue for IVL applications.

In contrast with previously implemented IVL applications, the present disclosure does not generate shock waves within a balloon or other sealed volume. Accordingly, there is a greater flexibility to the pressures used and types of tissues that can be treated. In further contrast with previously implemented IVL applications, the structures of the present disclosure have different acoustic properties. Embodiments of the present disclosure generate a lower peak positive pressure, a similar peak negative pressure, at higher frequency (100-200 Hz in the present disclosure versus 1-2 Hz for traditional IVL). In addition, the present disclosure aims at pulverizing lesions and aspirating debris, compared to IVL which break lesions that remain in situ. Moreover, traditional IVL relies on the initial shock wave with a high peak positive to break calcified lesions and has a lower peak negative which helps to prevent soft tissue damage. As is understood from the present disclosure, directional lithotripsy can take advantage of the initial and subsequent shock waves generated to break calcified lesions while still avoiding soft tissue damage.

FIG. 3 illustrates an exemplary electrode assembly 100 of a catheter. The assembly 100 includes a first cylindrical conductive sheath configured as an inner conductive sheath 120 and a second cylindrical conductive sheath configured as an outer conductive sheath 122. The outer conductive sheath 122 is mounted circumferentially around and concentric with the inner conductive sheath 120, such that the inner and outer conductive sheaths form respective inner and outer electrodes of an electrode pair. The conductive sheaths 120, 122 are formed from a conductive material, such as a conductive metal or alloy, that has been shaped into an extended tubular or cylindrical shape. In some examples, the inner conductive sheath 120 and/or outer conductive sheath 122 are formed from an erosion resistant metal tubing, such as stainless steel, platinum, palladium, iridium, molybdenum, tungsten, or copper tubing. The inner conductive sheath 120 may be any desired thickness, for example, between 0.002 and 0.003 inches thick. The outer conductive sheath 122 may be relatively thicker than the inner conductive sheath. For instance, the outer conductive sheath 122 could be approximately 0.004 to 0.006 inches thick. However, in other examples the inner conductive sheath 120 is thicker than the outer conductive sheath 122. For instance, the inner conductive sheath 120 could be between 0.004 to 0.006 inches thick, and the outer conductive sheath 122 could be relatively thinner, e.g., between 0.002 and 0.003 inches thick.

The inner conductive sheath 120 and the outer conductive sheath 122 each include a respective distal side edge 121, 123. The distal side edge 121 of the inner conductive sheath 120 is positioned proximate to the distal side edge 123 of the outer conductive sheath 122 to provide an arcing region between the sheaths across which current can flow to generate a shock wave inside the catheter. Together, the distal side edge 121 of the inner conductive sheath 120 and the distal side edge 123 of the outer conductive sheath 122 form an electrode pair of the electrode assembly 100. As will be described in more detail below, the distal side edge 121 of the inner conductive sheath 120 may be shaped such that a particular portion of the distal side edge 121 (e.g., portion 125) is closer to the outer conductive sheath 122 than the remainder of the distal side edge (i.e., to provide a predetermined initial arcing region between the conductive sheaths).

As seen in FIG. 3, the inner conductive sheath 120 and the outer conductive sheath 122 are separated by a cylindrical insulating layer 140, e.g., an insulation sheath, mounted between and concentric with the conductive sheaths 120, 122. The insulating layer 140 is formed from a non-conductive insulating material that prevents unintended current flow between the inner surface of the outer conductive sheath 122 and the outer surface of the inner conductive sheath 120. In some examples, the insulating layer 140 is formed from a polymeric material, e.g., a polyimide, shaped into an extended tubular or cylindrical shape. In some examples, the insulating layer 140 is approximately 0.002 to 0.004 inches thick. As seen in FIG. 3, the insulating layer 140 has a distal side edge 141 that is proximate to (e.g., flush with) the distal side edges 121, 123 of the respective inner and outer conductive sheaths 120, 122. The proximal side edge of the insulating layer 140 extends beyond the proximal side edge of at least one of the inner conductive sheath 120 and/or the outer conductive sheath 122 to prevent unintended current flow between the proximal side edges of the conductive sheaths 120, 122. The shape and position of the insulation layer 140 ensures that the initial arcing region between the inner conductive sheath 120 and outer conductive sheath 122 (i.e., the path of least resistance for current flow, normally the closest-distance location between the sheaths) is between the respective distal side edges 121, 123, and more particularly at the flush portion 125 of the inner conductive sheath 120.

Figure 4A:
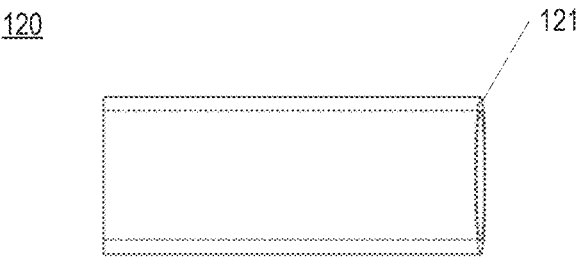
FIG. 4A illustrates a side view of an exemplary inner conductive sheath of an electrode assembly, such as the electrode assembly of FIG. 3, according to aspects of the present disclosure.
Figure 4B:
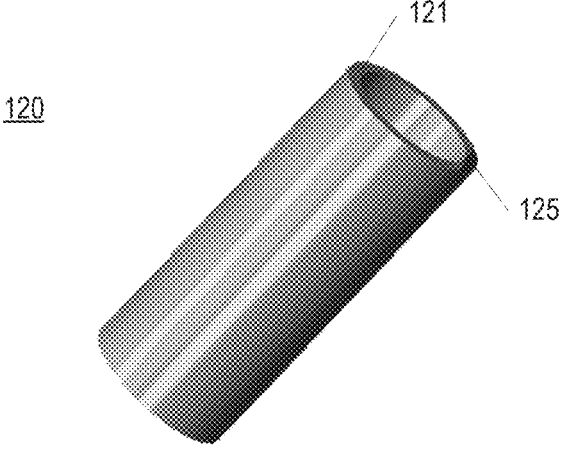
FIG. 4B illustrates a perspective view of an exemplary inner conductive sheath of an electrode assembly, such as the electrode assembly of FIG. 3, according to aspects of the present disclosure.

FIGS. 4A-4B illustrate an exemplary cylindrical inner conductive sheath 120 of an electrode assembly, such as the electrode assembly 100 of FIG. 3. FIG. 4A shows a side view of the exemplary inner conductive sheath 120, and FIG. 4B shows a perspective view of the exemplary inner conductive sheath 120. In some examples, the distal side edge 121 of the inner conductive sheath 120 is shaped to have various regions that are closer or farther away from the paired distal side edge 123 of the outer conductive sheath 122, which can thereby promote degradation in a predefined or semi-controlled manner. For instance, the distal side edge 121 of the inner conductive sheath 120 could be shaped such that a portion 125 of the distal side edge 121 is closest to the distal side edge 123 of the outer conductive sheath 122 in order to provide a predetermined initial arcing region for current flow between the conductive sheaths 120, 122. Second and further arcing regions could be provided by shaping additional portions of the distal side edge 121 to be the second closest to the distal side edge 123, and so on.

Figure 5A:
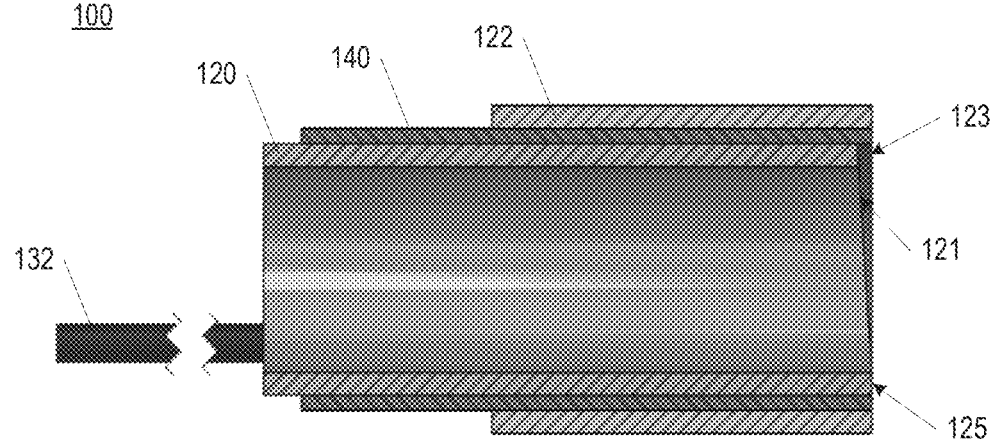
FIG. 5A illustrates a left side cross-sectional view of an exemplary electrode assembly of a catheter, according to aspects of the present disclosure.
Figure 5B:
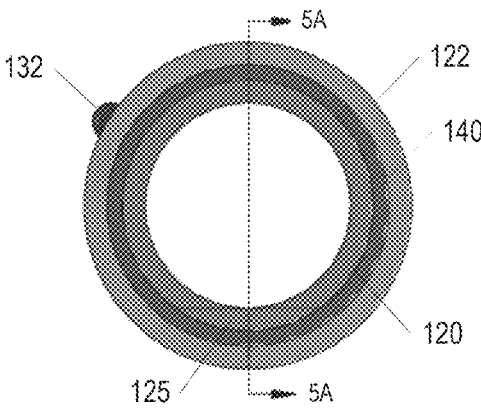
FIG. 5B illustrates a front view of the exemplary electrode assembly of FIG. 4A, according to aspects of the present disclosure.

FIGS. 5A-5B provide more detailed views of the electrode assembly 100 shown in FIG. 3. FIG. 5A illustrates a left side cross-sectional view of the electrode assembly 100. FIG. 5B illustrates a front view of the exemplary electrode assembly 100 showing the cutting plane used to generate the cross-sectional view in FIG. 5A. As seen in FIG. 5A, at least a portion the distal side edge 121 of the inner conductive sheath 120 is angled relative to the distal side edge 123 of the outer conductive sheath 122. At least a further portion (i.e., portion 125) of the distal side edge 121 is substantially flush with the distal side edge 123 of the outer conductive sheath 122 and the distal side edge 141 of the insulating layer 140 to provide an initial arcing region that is a relatively short distance away from the distal side edge 123 of the outer conductive sheath 122. The angled portion of the distal side edge 121 is angled in a proximal direction relative to the distal side edge 123 of the outer conductive sheath 122, such that the angled portion is farther away from the distal side edge 123 of the outer conductive sheath 122 than the flush portion 125. In some examples, the angled portion is angled a relatively small amount, e.g., between 2 degrees and 4 degrees or less than 2 degrees. However, in other examples the angled portion of the distal side edge 121 is angled a relatively larger amount, e.g., between 4 and 10 degrees, between 10 and 20 degrees, between 20 and 45 degrees, or greater than 45 degrees relative to the distal side edge 123 of the outer conductive sheath 122. It is understood that the angled portion of the distal edge 121 can be at any increment or gradient of degree within the above stated ranges.

Returning to FIG. 3, the electrode assembly 100 also includes two insulated wires 130, 132 extending along the length of the catheter. More particularly, a first insulated wire 130 is electrically connected with the inner conductive sheath 120 and a second insulated wire 132 is electrically connected with the outer conductive sheath 122. The insulated wires 130, 132 provide an electrical connection between the conductive sheaths 120, 122 and an external voltage source, e.g., a high voltage pulse generator (not pictured). In some examples, the inner conductive sheath 120 is connected to a positive terminal of the voltage source, and the outer conductive sheath 122 is connected to a negative terminal of the voltage source or to ground. However, the reverse connection is also envisioned (i.e., with the outer conductive sheath 122 connected to a positive terminal, and the inner conductive sheath connected to a negative terminal or to ground). In some examples, the conductive portions of the wires 130, 132 are heat-sealed or otherwise fixed to the conductive sheaths 120, 122 to provide a direct electrical connection. The insulated wires 130, 132 may extend within a fluid lumen of the catheter, e.g., fixed to a side wall of the lumen or disposed within grooves extending along the lumen. In other examples, the wires 130, 132 extend through a separate lumen of the catheter, e.g., a wire lumen.

A series of high voltage pulses can be delivered across the wires 130, 132 by an external voltage source, e.g., a pulsed high voltage source, to generate a series of shock waves and/or cavitation bubbles at the electrode assembly 100. Negative and positive terminals of the external voltage source are connected to the proximal ends of the first insulated wire 132 and the second insulated wire 132, creating a potential difference across the inner conductive sheath 120 and the outer conductive sheath 122 (i.e., an electrode pair of the electrode assembly) when high voltage pulses are delivered across the wires 130, 132. The potential difference causes current to flow through the electrode pair to generate shock waves and/or cavitation bubbles. The direction of current flow is dependent on the polarity of the electrodes, with current flowing from the more positively charged electrode (i.e., the electrode that is connected to the positive terminal of the voltage source) to the more negatively charged electrode (i.e., the electrode that is connected to the negative terminal of the voltage source). The duration and magnitude of the voltage pulse is sufficient to generate a gas bubble on the surface of the electrodes (i.e., on the distal side edges 121, 123 of the conductive sheaths 120, 122) and/or a shock wave.

The magnitude and other characteristics of the cavitation bubbles and/or shock waves can be controlled by adjusting the magnitude and duration of the applied voltage pulses. For instance, delivering relatively lower voltages at higher repetition rates (e.g., voltages between about 800 V and 2000 V, and repetition rates between about 20 Hz and 200 Hz) generally produces cavitation bubbles on the electrodes. When a series of relatively lower voltage and higher repetition rate voltage pulses are applied across the wires 130, 132, a plurality of gas cavitation bubbles accumulate on the surface of the electrodes. The cavitation bubbles can be flowed through the open tip of a catheter and into a treatment site to break up a calcified lesion. Applying higher voltage pulses at lower repetition rates (e.g., voltages between about 2500 V and 6000 V and repetition rates between about 1 Hz and 4 Hz) produces higher magnitude acoustic shock waves in the catheter. When a series of relatively higher voltage pulses are applied across the wires 130, 132, a plasma arc of electric current eventually forms across a bubble at the arcing region 125 between the inner conductive sheath 120 and the outer conductive sheath 122. The current traverses the bubble and creates a rapidly expanding and collapsing bubble that produces an acoustic shock wave that propagates toward a target lesion. The characteristics of the cavitation bubbles and/or shock waves can also be controlled by adjusting aspects of the electrode assembly, e.g., the distance between electrodes of an electrode pair, the surface area of the electrodes, and the shape of the electrodes.

FIG. 16 is a graph showing measurements of pressure generated by a device fabricated in accordance with FIGS. 3 to 5. The measurements were made by a hydrophone located about ten millimeters (10 mm) from the emitter location, where in the context of the present disclosure, an emitter broadly refers to the region of the electrode assembly where the current travels across the electrode pair, generates a shock wave, and propagates a resulting bubble. The measurements in FIG. 16 are in megapascals (MPa), and as a general estimate, the pressure close to the emitter at one millimeter (1 mm) in front of the emitter (i.e., the distance of cavitation bubble and subsequent shock wave formation), is about an order of magnitude greater than the pressure measured at the hydrophone 10 mm distant. As can be seen in FIG. 16, there is a large positive spike at the beginning of the shock wave pulse of about 1.32 MPa. Based on the measurement at the hydrophone, the estimated pressure close to the emitter (1 mm) would be about 13.2 MPa. A smaller but still significant negative spike is recorded near the end of the pulse, about nine microseconds (9 μs) after the initial positive spike. The negative pressure spike is caused by the collapse of the vapor bubble. At distance of ten millimeters (10 mm) from the emitter, the hydrophone measured 0.19 MPa, corresponding to an estimated negative pressure close to the emitter of about 1.9 MPa. Accordingly, the peak-to-peak difference in pressure at one millimeter (1 mm) from the emitter would be about 15 MPa. As noted herein, this type of pressure swing can enhance clearing of the lesions from the treatment site.

The magnitude and frequency of the voltage pulses can also be controlled to improve the characteristics of acoustic pressure waves resulting from the generation of shock waves or cavitation bubbles at an electrode pair. For instance, delivering voltage pulses with a relatively short pulse widths, e.g., below fifty microseconds (<50 μs), can produce acoustic pressure waves having relatively high amplitude negative pressures. Increased negative pressures can improve the mechanism of action of a shock wave or cavitation catheter by providing a negative suction-like force that facilitates the clearing of lesions and debris from a treatment site. In some examples, voltage pulses can be delivered across an electrode pair at relatively low frequencies, e.g., frequencies between 30-40 Hz, between 40-50 Hz, or greater than 50 Hz, and relatively short pulse widths, e.g., pulse widths of approximately ten microseconds (10 μs) or less than ten microseconds, to produce acoustic pressure waves having high negative pressure. In certain examples, an electrode pair of a catheter can produce acoustic pressure waves having peak negative pressures of approximately 3 MPa, with peak-to-peak pressures of approximately 10 MPa. However, in other examples an electrode pair may produce acoustic pressure waves having even greater peak pressure, for instance, peak pressures between 10 MPa and 20 MPa, between 20 MPa and 40 MPa, or up to 50 MPa.

When voltage pulses are applied during a shock wave and/or cavitation treatment, current flows across the lowest-resistance path between the electrodes of an electrode pair, which is generally the location where the electrodes are closest in distance. Thus, an initial arcing region is located where the distal side edge 121 of the inner conductive sheath 120 is closest to the distal side edge 123 of the outer conductive sheath 122. Repeated generation of cavitation bubbles and/or shock waves will cause the electrodes to erode proximate the initial arcing region. For instance, in the example shown in FIG. 3, generating cavitation bubbles and/or shock waves will cause the distal side edge 121 of the inner conductive sheath 120 to erode proximate to the portion 125 of the distal side edge 121 that is flush with and closest to the distal side edge 123 of the outer conductive sheath 122. Throughout the course of a treatment, the distal side edge 121 of the inner conductive sheath 120 will continue to erode proximate to the initial arcing region. Once the initial arcing region erodes far enough that it is no longer the shortest distance between the inner conductive sheath 120 and the outer conductive sheath 122, current will begin to flow across a secondary arcing region that provides the shortest distance path between the distal side edge 123 of the outer conductive sheath 122 and the partially degraded distal side edge 121 of the inner conductive sheath 120. As the shock wave treatment continues, the angled shape of the inner conductive sheath 120 promotes degradation in a semi-controlled pattern around the distal side edge 121 of the inner conductive sheath, beginning at the flush portion 125 and proceeding along the portions of the distal side edge 121 that are successively farther from the outer conductive sheath 122. In other words, the structure of the constituent electrodes guides the location of the electrical arcs and thereby partially controls the pattern of electrode erosion throughout use of the electrode assembly.

Figure 6:
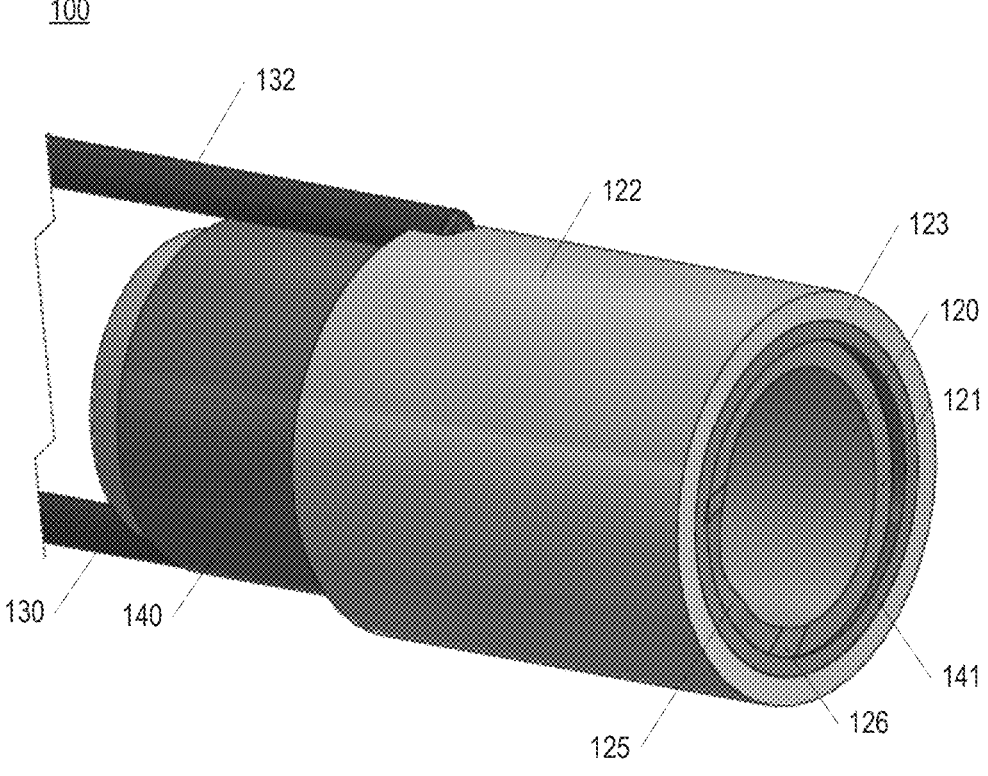
FIG. 6 illustrates a perspective view of the exemplary electrode assembly of FIG. 3 after the inner conductive sheath has been degraded by the generation of a series of shock waves or cavitation bubbles, according to aspects of the present disclosure
Figure 7A:
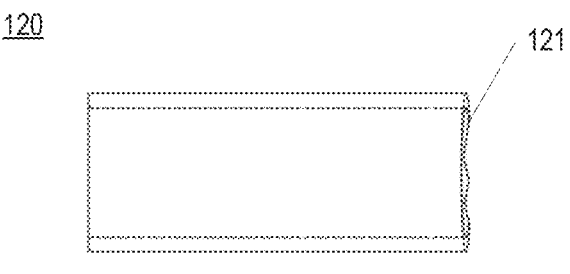
FIG. 7A illustrates a front side view of an exemplary inner conductive sheath of an electrode assembly, such as the electrode assembly of FIG. 6, according to aspects of the present disclosure.
Figure 7B:
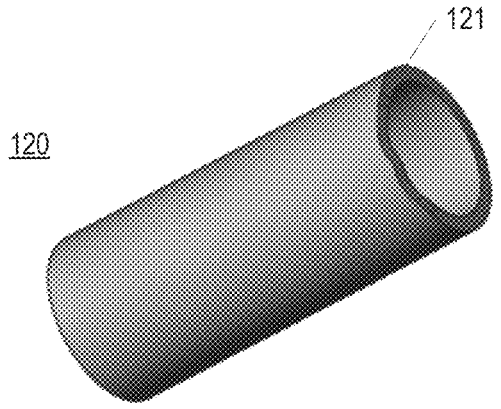
FIG. 7B illustrates a perspective view of an exemplary inner conductive sheath of an electrode assembly, such as the electrode assembly of FIG. 6, according to aspects of the present disclosure.

FIG. 6 illustrates a partially eroded exemplary electrode assembly 100, such as the assembly 100 shown in FIGS. 3 and 5A-5B, after the inner conductive sheath 120 has been at least partially eroded by the generation of a series of shock waves and/or cavitation bubbles. FIG. 7A shows a side view of the exemplary eroded inner conductive sheath 120, and FIG. 7B shows a perspective view of the exemplary eroded inner conductive sheath 120. FIGS. 8A-8B provide more detailed views of the partially eroded electrode assembly 100 shown in FIG. 6. FIG. 8A illustrates a left side cross-sectional view of the exemplary eroded electrode assembly 100. FIG. 8B illustrates a front view of the exemplary electrode assembly 100 showing the cutting plane used to generate the sectional view in FIG. 8A. FIG. 8C shows an enlarged left side cross-sectional view of the exemplary electrode assembly 100 shown in FIG. 8A to provide a more detailed view of the degraded distal side edge of the inner conductive sheath 100.

As seen in FIGS. 6, 7A-7B, and 8A-8C, the repeated generation of shock waves and cavitation bubbles has caused the distal side edge 121 of the inner conductive sheath 120 to erode proximate to the initial arcing region, creating one or more divots in the distal side edge 121. The degradation of the electrode surface at the initial arcing region has increased the distance between the portion 125 and the distal side edge 123 of the outer conductive sheath 122, causing a different portion 126 of the electrode surface to become closer in distance to the distal side edge 123 (accordingly, portion 125 is no longer flush as shown in FIGS. 4B, 5A, and 5B). As additional voltage pulses are applied across the sheaths 120, 122, erosion of the inner conductive sheath 120 at the initial arcing region will cause current to flow across a secondary arcing region between the distal side edge 121 of the inner conductive sheath 120 and the distal side edge 123 of the outer conductive sheath 122 (e.g., a region proximate to the new closest-in-distance portion 126).

In the particular embodiment shown in FIGS. 6 and 8A-8C, the secondary arcing region is proximate to the initial arcing region around the circumference of the distal side edge 121. The gradually sloping angle of the distal side edge 121 causes degradation to proceed outward from the initial arcing region (e.g., a region proximate to portion 125) to portions of the distal side edge 121 that are farther and farther from the distal side edge 123 of the outer conductive sheath 122 (e.g., to portion 126 and then subsequent farther-in-distance portions of the distal side edge 121). Eventually, when the entire circumference of the distal side edge 121 has eroded to an approximately equal distance from the distal side edge 123 of the outer conductive sheath 122, degradation may proceed in a stochastic manner as current flows across the relatively least resistance (i.e., closest distance) path between the sheaths 120, 122.

In the embodiments shown in FIGS. 6, 7A-7B, and 8A-8C, the erosion is shown as affecting primarily the distal side edge 121 of the inner conductive sheath 120. This is the observed pattern, particularly when the inner conductive sheath 120 is connected to the positive terminal of a voltage source. It should be noted that the distal side edge 123 of the outer conductive sheath 122 may also erode in a similar fashion, particularly if the polarity of the power supply with respect to the sheaths is reversed such that the outer conductive sheath 122 is connected to the positive terminal of the voltage source. When the polarity of the electrode assembly is reversed, current flows in the opposite direction across the arcing region between the sheaths 120, 122, causing erosion that affects primarily the distal side edge 123 of the outer conductive sheath 122. Electrode assembly designs where the erosion occurs primarily on the outer conductive sheath 122 may provide an increased electrode lifespan compared to assemblies where erosion occurs primarily on the inner conductive sheath 120, due to the relatively larger circumference and greater electrode surface area of the outer conductive sheath's distal side edge 123.

In these example embodiments, the distal side edge 123 of the outer conductive sheath 122 may be shaped to promote degradation in a predetermined or semi-controlled manner, e.g., shaped similarly to the distal side edge 121 of the inner conductive sheath 120 shown in FIGS. 6, 7A-7B, and 8A-8C. As described previously in relation to the inner conductive sheath 120, the outer conductive sheath 122 can be shaped such that various regions of the distal side edge 123 are closer or farther away from the paired distal side edge 121 of the inner conductive sheath 120. For instance, the distal side edge 123 of the outer conductive sheath 122 could be shaped such that a portion 125 of the distal side edge 121 is closest to the distal side edge 121 of the inner conductive sheath 120 to provide a predetermined initial arcing region. Second and further arcing regions could be provided by shaping additional portions of the distal side edge 123 to be the second closest to the distal side edge 121, and so on.

Figure 9A:
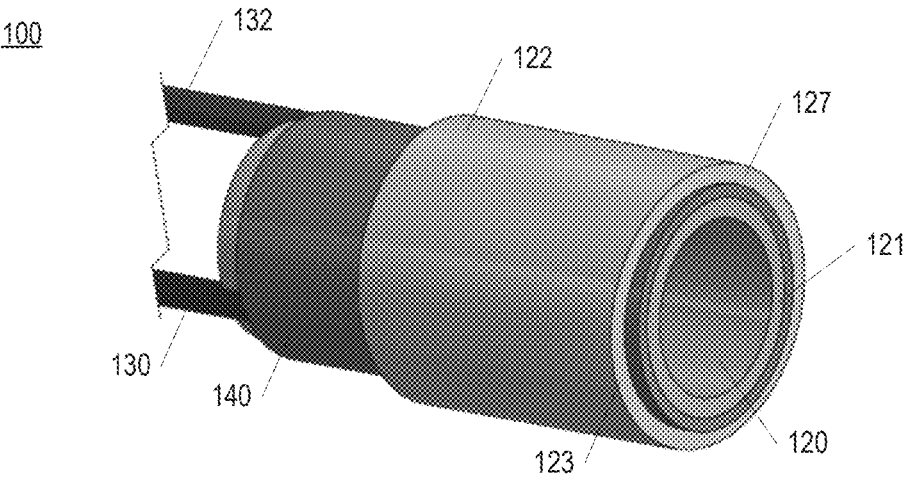
FIG. 9A illustrates a perspective view of an exemplary electrode assembly of a catheter, according to aspects of the present disclosure.
Figure 9B:
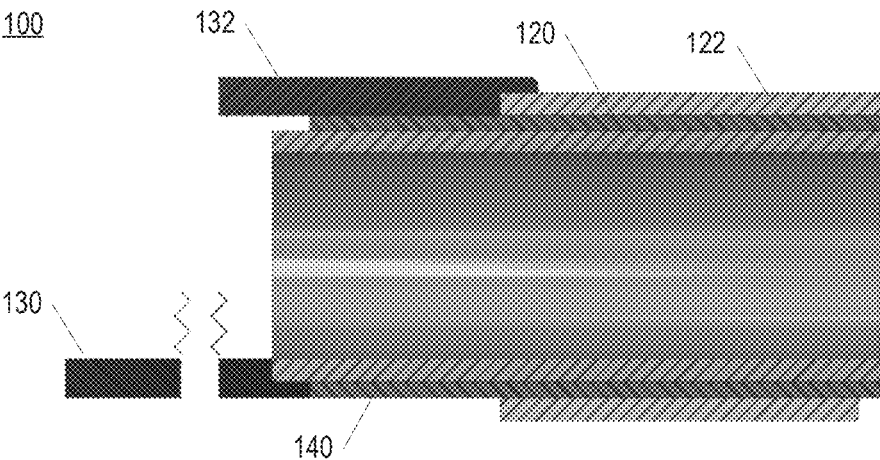
FIG. 9B illustrates a left side cross-sectional view of the exemplary electrode assembly of a catheter shown in FIG. 9A, according to aspects of the present disclosure.

FIGS. 9A and 9B illustrate one exemplary electrode assembly, where the distal side edge 123 of the outer conductive sheath 122 is angled relative to the distal side edge 121 of the inner conductive sheath 120. At least a portion, here portion 127, of the distal side edge 123 is substantially flush with the distal side edge 121 of the inner conductive sheath 120 and the distal side edge of the insulating layer 140 to provide an initial arcing region that is a relatively short distance away from the distal side edge 121 of the inner conductive sheath 120. As seen in FIGS. 9A-9B, the surface of the distal side edge 123 gradually slopes away from the distal side edge 121 of the inner conductive sheath 120 in a proximal direction relative to the distal side edge 121. In some examples, the distal side edge

123 is angled a relatively small amount, e.g., between 2 degrees and 4 degrees or less than 2 degrees. However, in other examples distal side edge 123 is angled a relatively larger amount, e.g., between 4 and 10 degrees, between 10 and 20 degrees, between 20 and 45 degrees, or greater than 45 degrees relative to the distal side edge 121 of the inner conductive sheath 120. It is understood that the angled portion of the distal edge 123 can be at any increment or gradient of degree within the above stated ranges.

Figure 10:
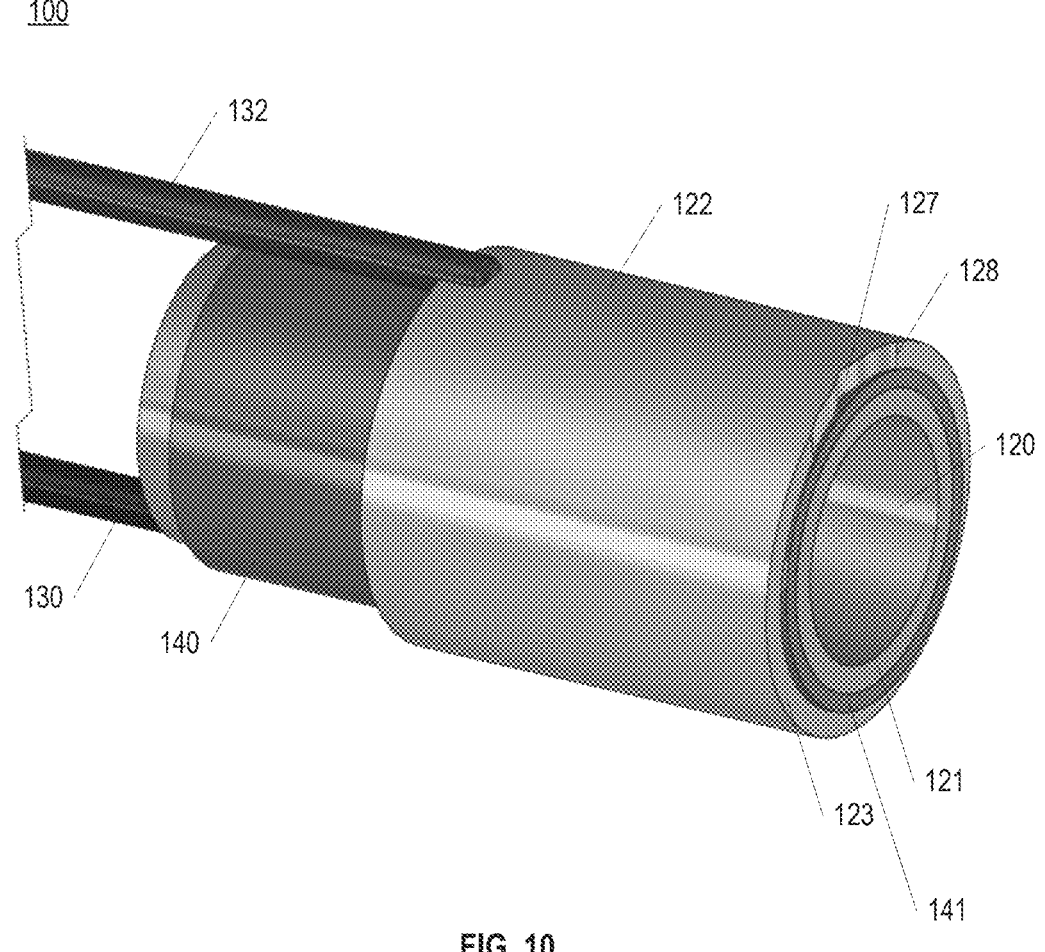
FIG. 10 illustrates a perspective view of the exemplary electrode assembly of FIG. 9A after the outer conductive sheath has been degraded by the generation of a series of shock waves or cavitation bubbles, according to aspects of the present disclosure

FIG. 10 illustrates the electrode assembly of FIGS. 9A-9B after the outer conductive sheath 122 has been at least partially eroded by the generation of a series of shock waves and/or cavitation bubbles. FIGS. 11A-11C provide more detailed views of the partially eroded electrode assembly 100 shown in FIG. 10. FIG. 11A illustrates a left side cross-sectional view of the partially eroded electrode assembly 100. FIG. 11B illustrates a front view of the partially electrode assembly 100 showing the cutting plane used to generate the sectional view in FIG. 11A. FIG. 11C shows an enlarged left side cross-sectional view of the exemplary electrode assembly 100 shown in FIG. 11A to provide a more detailed view of the degraded distal side edge of the inner conductive sheath 100. As seen in FIGS. 10 and 11A-11C, the repeated generation of shock waves and/or cavitation bubbles has caused the distal side edge 123 of the outer conductive sheath 122 to erode proximate to the initial arcing region, increasing the distance between the portion 127 and the distal side edge 121 of the inner conductive sheath 120. Eventually, erosion of the outer conductive sheath 122 at the initial arcing region causes a different portion 128 of the distal side edge 123 to become closer in distance to the distal side edge 121 of the inner conductive sheath 120. As additional voltage pulses are applied across the sheaths 120, 122, current will begin to flow across a secondary arcing region between the distal side edge 123 of the outer conductive sheath 122 and the distal side edge 121 of the inner conductive sheath 120 that provides the new closest-in-distance path between the sheaths. In the particular embodiment shown in FIGS. 10 and 11A-11C, the gradually sloping angle of the distal side edge 123 causes degradation to proceed outward from the initial arcing region (e.g., a region proximate to portion 127) to portions of the distal side edge 123 that are farther and farther from the distal side edge 121 of the inner conductive sheath 120 (e.g., to portion 128 and then subsequent farther-in-distance portions of the distal side edge 123).

While FIGS. 3, 5A-5B, 6, 8A-8C, 9A-9B, 10, and 11A-11C illustrate exemplary electrode assemblies formed from concentric conductive sheaths 120, 122 shaped with angled distal side edges 121, 123, other electrode configurations may also result in favorable degradation patterns. For instance, in some examples one or more of the distal side edges 121, 123 are shaped with a different pattern that places various portions of the edge at different predetermined distances from the other conductive sheath, e.g., shaped with undulating waves, notches, differently angled portions, or some other surface configuration. Further, while the preceding example electrode assemblies include only one shaped conductive sheath, in some examples both the inner conductive sheath 120 and the outer conductive sheath 122 include shaped distal side edges 121, 123. Additionally or alternatively, the insulating layer 140 could be shaped to promote erosion in a desired pattern across the conductive sheaths 120, 122. For instance, the insulating layer 140 could have a shaped (e.g., angled) distal side edge, or one or more apertures through the insulating layer defining various arcing regions between the inner conductive sheath 120 and the outer conductive sheath 122.

To even further increase the useable lifespan of an electrode assembly included in a catheter, the polarity of the electrode assembly can be switched one or more times during a shock wave or cavitation procedure. For instance, U.S. Pat. No. 10,226,265, incorporated herein by reference, describes switching the polarity of voltage pulses applied across an electrode pair to cause the direction of current flow to change during a procedure. As described previously, an electrode connected to a positive terminal of a voltage source generally experiences increased erosion compared to an electrode connected to a negative terminal or to ground. Accordingly, switching the polarity of an electrode assembly during a procedure can allow a user to control the relative degradation at the surface of each electrode of an electrode pair. Over the course of a shock wave or cavitation procedure, polarity switching can be used to more evenly distribute degradation across both electrodes of an electrode pair, increasing the useable lifespan of an electrode assembly. It should be noted that electrode polarity switching can be implemented in any electrode assembly design, including but not limited to the assemblies shown throughout the present disclosure.

Polarity switching can be implemented using a controller, e.g., a polarity switching circuit and/or a multiplexer, in electrical connection with the external voltage source and the electrode assembly. As described previously, the external voltage source is configured to selectively deliver a series of high voltage pulses across the wires 130, 132 of the electrode assembly to generate shock waves and/or cavitation bubbles at an electrode pair of the assembly. The direction of current flow across the electrode pair is determined by the polarity of the electrodes, i.e., the relative negative and positive charge of the electrodes. The polarity can be modified by selectively connecting the positive and negative terminals of the voltage source across the first and second insulated wires 130, 132 to cause current to flow in a particular direction across the electrodes of electrode pair (i.e., from the positive electrode to the negative electrode). Accordingly, the controller is configured to control the direction of current flow through an electrode pair by selectively delivering high voltage pulses with a desired polarity across an electrode assembly.

When a series of voltage pulses is delivered across an electrode assembly, the polarity can be controlled by the controller such that a certain number of pulses in the series cause current to flow in a first direction, and the remaining number of pulses in the series cause current to flow in a second direction opposite the first direction. In a particular example, the polarity of the assembly can be switched at periodic intervals during a procedure, e.g., with the controller causing polarity switches after every voltage pulse or after a certain number of voltage pulses (e.g., switching polarity every two, three, four, or more pulses of a series). In another example, the controller can be configured to control the polarity such that a certain proportion of voltage pulses cause current to flow in a first direction, and a remaining proportion of voltage pulses cause current to flow in a second direction opposite the first direction. For instance, the polarity of the assembly may be controlled such that current flows in a first direction for one half, one third, or one quarter of the voltage pulses in a series, and flows in the opposite direction for the remaining pulses in the series.

To selectively promote erosion of the outer conductive sheath 122, the controller may cause a relatively greater number of voltage pulses of a series to be delivered with the outer conductive sheath connected to the positive terminal of the voltage source. For instance, the controller may cause current to flow from the inner conductive sheath 120 to the outer conductive sheath 122 for one-fifth (⅕), one-fourth (¼), one-third (⅓), two-fifths (⅖), one-half (½), three-fifths (⅗), two-thirds (⅔), three-fourths (¾), four-fifths (⅘), or some other proportion or ratio of the voltage pulses of a series. However, a controller can be configured to switch the polarity of an electrode assembly such that current flows in a particular direction across the assembly for any desired proportion of voltage pulses of a series.

Moreover, a controller can be configured with a progressing sequence of voltage pulsing, such that the number of pulses in a given direction (e.g., from inner conductive sheath 120 to outer conductive sheath) can increase or decrease over the course of use. For a decreasing example, in a given treatment procedure with 300 pulses the first half (150 pulses) of a voltage pulsing sequence may have a ratio of four-fifths (⅘) with 120 pulses with current going in the inner-to-outer direction and 30 pulses with current going in the outer-to-inner direction, and the second half (the remaining 150 pulses) of the voltage pulsing sequence may have a ratio of one-half (½) with 75 pulses for current in each direction. It can be understood that further variations of pulse sequencing can be extrapolated from this example.

In some examples, the controller automatically initiates polarity switches based on readings at a sensor in electrical connection with the controller. For instance, the sensor may be configured to measure operating parameters of the electrode assembly, such as current flow through the assembly, voltage pulse width, time from the delivery of a voltage pulse to the initiation of a shock wave across an electrode pair, temperature of one or more of the electrodes, or some other parameter. If the parameter is greater than or lower than a predefined polarity switching threshold, the controller changes the direction of current flow across the electrode pair by modifying the polarity of the voltage pulses. In some examples, the sensor is configured to measure a parameter that correlates with the relative erosion of the electrodes of an electrode pair, so that the controller can initiate polarity switches automatically to balance the erosion between the electrodes of the pair. In a particular example, the sensor measures the flow of current across an electrode pair, and the controller automatically initiates a polarity switch when current falls below a predefined polarity switching threshold value (e.g., a threshold that indicates that current flow has been negatively impacted by electrode degradation). In another example, the sensor measures a voltage pulse width or a duration of time between the delivery of a voltage pulse and the initiation of a shock wave or cavitation bubble at an electrode pair. If the voltage pulse width or duration of time measured by the sensor exceeds a predefined polarity switching threshold value (e.g., a threshold indicating that the formation of a shock waves/cavitation bubbles has been negatively impacted by electrode degradation), the controller automatically initiates a polarity switch to change the direction of current flow through the electrode pair.

In some examples, the controller is configured to terminate the delivery of voltage pulses when a parameter measured by the sensor is greater than or lower than a termination threshold value (e.g., to end the shock wave or cavitation procedure responsive to an error mode or undesirable operating conditions detected by the sensor). In such examples, the threshold value for polarity switching may be a function of the termination threshold value. For instance, polarity switching may be implemented when the measured parameter is greater than or lower than approximately 70% of the termination threshold. In a particular example, the termination threshold is one hundred milliseconds (100 ms) between the delivery of a voltage pulse and the initiation of a shock wave or cavitation bubble at an electrode pair, and the polarity switching threshold is approximately seventy milliseconds (70 ms) between the delivery of the pulse and the generation of a shock wave or cavitation bubble. In other examples, polarity switches may be initiated when the measured parameter is between 50-70%, between 70-90%, or between 90-100% of the termination threshold value.

Figure 12:
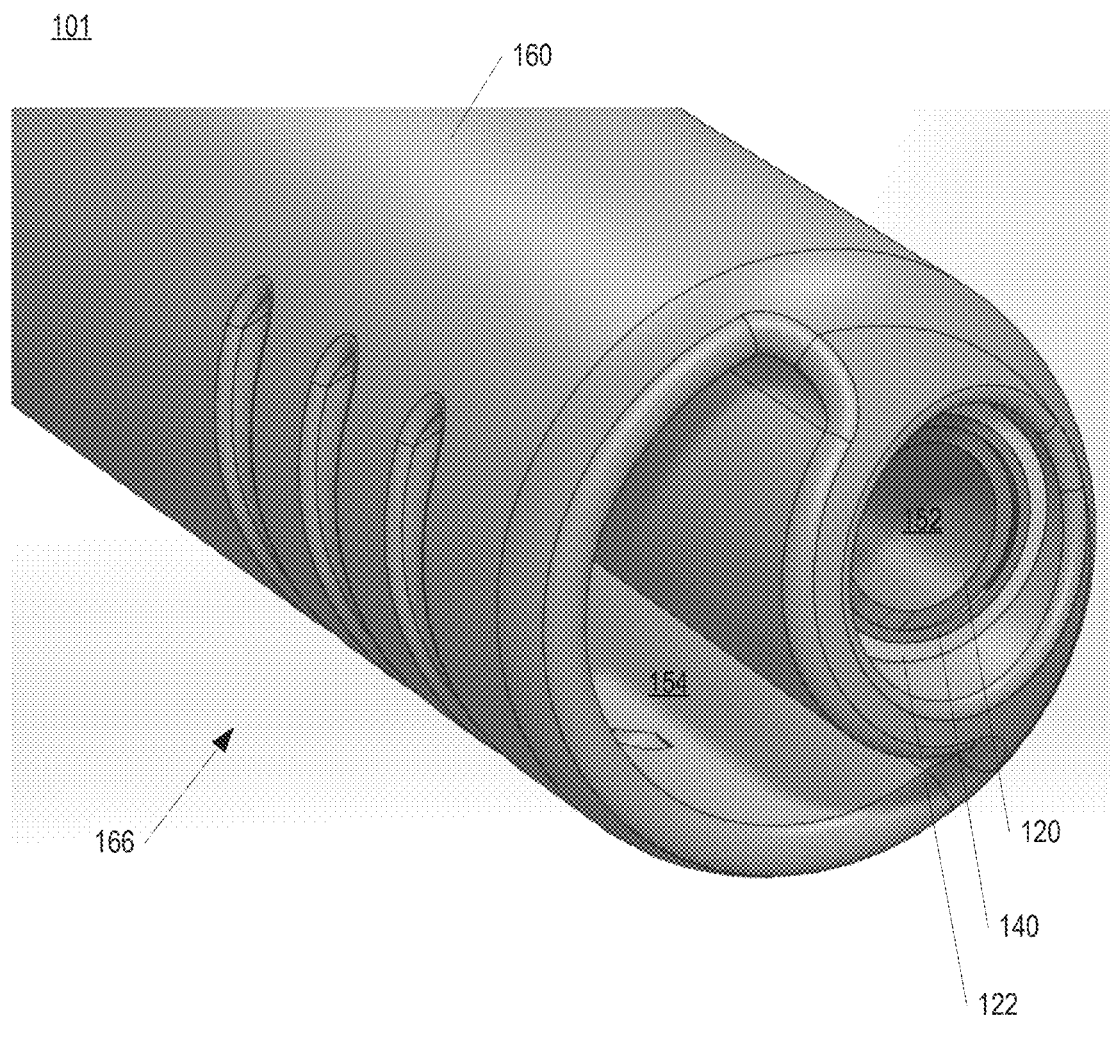
FIG. 12 illustrates a perspective view of the distal end of an exemplary catheter, according to aspects of the present disclosure.
Figure 13A:
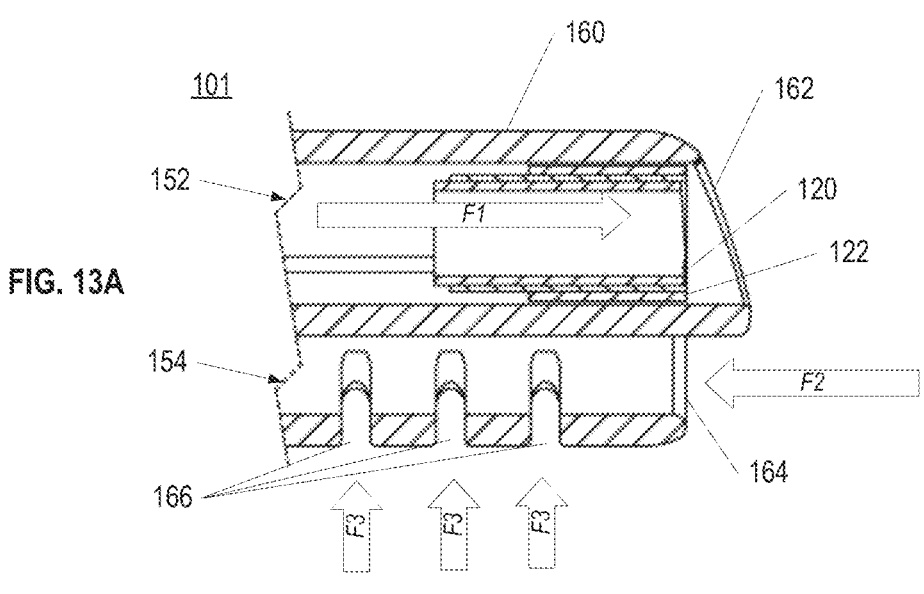
FIG. 13A illustrates a top side cross-sectional view of the distal end of the exemplary catheter shown in FIG. 12, according to aspects of the present disclosure.
Figure 13B:
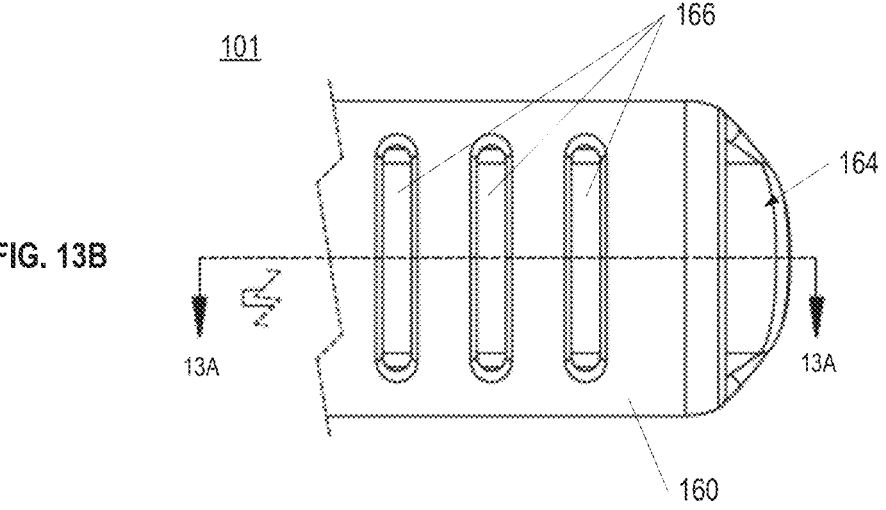
FIG. 13B illustrates a left side view of the distal end of the exemplary catheter shown in FIG. 12, according to aspects of the present disclosure.
Figure 13C:
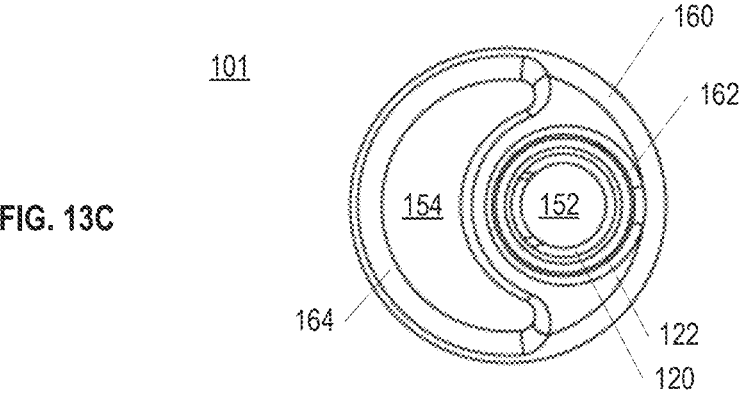
FIG. 13C illustrates a front view of the distal end of the exemplary catheter shown in FIG. 12, according to aspects of the present disclosure.

FIG. 12 illustrates a perspective view of the distal end of an exemplary catheter 101 that includes a dual-layer electrode assembly, such as any of the exemplary electrode assemblies 100 shown throughout and described in this disclosure. FIGS. 13A-13C provide additional views of the distal end of the exemplary catheter 101 shown in FIG. 12, particularly illustrating fluid lumen 152 and aspiration lumen 154. FIG. 13A provides a top side cross-sectional view of the exemplary catheter 101 depicting the flow of fluid through the catheter body. FIG. 13B provides a left side view of the exemplary catheter 101 showing the cutting plane used to generate the sectional view in FIG. 13A. FIG. 13C provides a front view of the exemplary catheter 101 depicting the fluid lumen 152 and the aspiration lumen 154.

FIGS. 14A-14B illustrate perspective views of alternative embodiments of a catheter 101 further featuring a guidewire lumen 156. FIG. 14A provides an example including an electrode assembly having a shaped inner conductive sheath 120 (e.g., one of the exemplary electrode assemblies throughout this disclosure). FIG. 14B provides an example of a similar catheter design including an electrode assembly having a shaped outer conductive sheath 122. FIGS. 15A-15C provide additional views of the distal end of the exemplary catheter 101 shown in FIG. 14B, including a top side cross-sectional view in FIG. 15A, a left side view in FIG. 15B showing the cutting plane used to generate the sectional view in FIG. 15A, and a front view in FIG. 15C depicting the fluid lumen 152, the aspiration lumen 154, and the guidewire lumen 156.

As seen in FIGS. 12 and 14A-14B, an exemplary catheter 101 includes an annular catheter body, i.e., an elongated tube 160, that terminates at a distal end (i.e., the end of the catheter 101 shown in FIGS. 12 and 14A-14B that is introduced into a body lumen). The elongated tube 160 is formed from a rigid or semi-rigid material, such as a shaped polymeric material. The elongated tube 160 includes a number of lumens, for instance, a fluid lumen 152, an aspiration lumen 154, and optionally a guidewire lumen 156. The fluid lumen 152 is configured for flowing a fluid, e.g., a conductive fluid such as saline, along the length of the catheter body and through a fluid outflow port 162 at a distal end of the elongated tube 160. The aspiration lumen 154 is configured to receive debris from the treatment site through a fluid inflow port 164, and flow the debris through the lumen 154 and to a proximal portion of the catheter 101. In some examples, the catheter 101 further includes one or more aspiration ports 166 extending through side walls of the elongated tube 160, such that debris can be suctioned through the side walls and into the aspiration lumen 154. In some examples, and as seen in FIGS. 14A-14B, the catheter 101 includes a guidewire lumen 156 sized to receive a guidewire. To facilitate positioning of the catheter 101 with a body lumen, a guidewire can be inserted through the guidewire lumen and the catheter can be maneuvered over the guidewire through the lumen to a treatment site proximate to a lesion.

As seen in FIGS. 12, 13A, 14A-14B, and 15A, an electrode assembly is mounted within the elongated tube 160 proximate to the distal tip of the catheter 101 such that shock waves can be generated within the catheter body. In some examples, the electrode assembly is mounted within the fluid lumen 152 such that fluid flowing through the lumen flows across the electrode assembly. The outer conductive sheath 122 is mounted inside the fluid lumen 152 adjacent to the walls of the fluid lumen 152, such that the outer surface of the outer conductive sheath 122 contacts the inner surface of the fluid lumen 152. The insulation sheath 140 is mounted in the fluid lumen 152 inside and concentric with the outer conductive sheath 122 such that the outer surface of the insulation sheath 140 contacts the inner surface of the outer conductive sheath 122. The inner conductive sheath 120 is also mounted in the fluid lumen 152 inside and concentric with the outer conductive sheath 122 and the insulation sheath 140, with the outer surface of the inner conductive sheath 120 contacting the inner surface of the insulation sheath 140. In other words, the outer conductive sheath 122 is mounted within the fluid lumen 152 circumferentially around the inner conductive sheath 120, with the insulation layer 140 positioned therebetween.

FIGS. 13A and 15A both depict the flow of fluid, e.g., conductive fluid, through the distal end of the exemplary catheter 101. As seen in FIGS. 13A-13C and FIGS. 15A-15C, the electrode assembly is mounted within the fluid lumen 152 of the catheter 101 such that fluid flowing through the fluid lumen 152 flows through the inner conductive sheath 120 before exiting the fluid outflow port 162 (see, e.g., the upper horizontal arrow F1 in FIGS. 13A and 15A representing the flow of fluid through the fluid lumen 152). The conductive fluid in the catheter 101 provides a path for current to flow between the inner conductive sheath 120 and the outer conductive sheath 122, i.e., to allow for the generation of cavitation bubbles and/or shock waves during a treatment. Fluid flow through the inner conductive sheath 120 can also cause cavitation bubbles produced by the electrode assembly to flow out of the distal end of the catheter 101 and into a lesion to aid in cracking and disrupting the lesion. Additionally, the flow of fluid through the inner conductive sheath 120 can be used to clear debris from the surface of the electrodes (e.g., debris produced from erosion of the surfaces of the inner conductive sheath 120 and/or outer conductive sheath 122) and to regulate the temperature of the electrode assembly (e.g., by cooling the electrode assembly). Fluid can be received into the catheter 101 through a fluid inflow port 164 located at the distal end of the aspiration lumen 154. In some examples, fluid may also be received via aspiration ports 166 extending through the outer surface of the elongated tube 160. Inward suction through the aspiration lumen 154 allows the catheter 101 to circulate fluid through the treatment site to aspirate the site and remove any bubbles and debris produced during treatment (see, e.g., the lower horizontal arrow F2 and three vertical arrows F3 in FIGS. 13A and 15A representing the flow of fluid into the aspiration lumen 154).

FIG. 17 illustrates a perspective view of an exemplary electrode assembly 200 of a catheter. In one or more examples, the electrode assembly 200 can be used to generate shock waves and/or cavitation bubbles to treat calcified lesions in the vasculature of a patient using acoustic pressure without harming the surrounding tissue. As shown in FIG. 17, the electrode assembly 200 includes a flat helical wire configured as a flat coil 220, and a cylindrical conductive sheath configured as a conductive sheath 222, separated by an insulation sheath 240. The insulation sheath 240 is mounted circumferentially within the conductive sheath 222, with the flat coil 220 disposed on an inner surface of the insulation sheath 222 such that the flat coil 220 and the conductive sheath 222 form respective electrodes of an electrode pair.

The conductive sheath 222 and the flat coil 220 can be formed from a conductive material, such as a conductive metal or alloy. In one or more examples, the conductive sheath 222 can be formed from an erosion resistant metal tubing, such as stainless steel, platinum, palladium, iridium, molybdenum, tungsten, or copper tubing that has been shaped into an extended tubular or cylindrical shape. The flat coil 220 can similarly be formed from an erosion resistant metal material, such as stainless steel, platinum, palladium, iridium, molybdenum, tungsten, or copper that has been shaped into a flat helical coil. The flat coil 220 can be any desired thickness, for example, between 0.002 and 0.003 inches thick. In one or more examples, the conductive sheath 222 can be relatively thicker than the flat coil 220. For instance, the conductive sheath 222 could be approximately 0.004 to 0.006 inches thick. Alternatively, the flat coil 220 can be thicker than the conductive sheath 222. For example, the flat coil 220 could be between 0.004 to 0.006 inches while the conductive sheath 222 can be relatively thinner, e.g., between 0.002 to 0.003 inches thick.

In one or more examples, the flat coil 220 and the conductive sheath 222 form an electrode pair of an electrode assembly for a catheter. As shown in FIG. 17, the flat coil 220 has a distal end 221 and the conductive sheath has a distal side edge 223. The distal end 221 of the flat coil 220 is positioned proximate to the distal side edge 223 of the (relatively outer) conductive sheath 222, to create an arcing region across which current can flow between the flat coil 220 and the conductive sheath 222. In one or more examples, current flowing across this arcing region can generate shockwaves and/or cavitation bubbles inside the catheter.

As seen in FIG. 17, the flat coil 220 and the conductive sheath 222 are separated by the insulator sheath 240. The insulating sheath 240 can be formed from a non-conductive insulating material that prevents unintended current flow between certain regions of the flat coil 220 and the conductive sheath 222. In one or more examples, the insulator sheath 240 can block any flow of current between the flat coil 220 and the conductive sheath 222 along the length of the insulator sheath 240. Because current is prevented from flowing between the flat coil 220 and the conductive sheath 222 along the length of the insulator sheath 240, the current can only flow across the arcing region between the distal end 223 of the conductive sheath 222 and the distal end 221 of the flat coil 220. In one or more examples, the insulator sheath 240 can be formed from a polymeric material, e.g., a polyimide, that is shaped into an extended tubular or cylindrical shape. In one or more examples, the insulator sheath 240 can be approximately 0.002 to 0.004 inches thick.

As shown in FIG. 17, the insulator sheath 240 has a distal side edge 241. In one or more examples, the distal side edge 241 of the insulator sheath 240 can be proximate to (e.g., flush with) the distal side edges of the conductive sheath 222 and/or the flat coil 220. The proximal side edge of the insulator sheath 240 can extend beyond the proximal side edge of at least one of the conductive sheath 222 and the flat coil 220 to prevent unintended current flow between the proximal side edges of the conductive sheath 222 and the flat coil 220. The shape and position of the insulating sheath 240 can ensure that the arcing region between the flat coil 220 and the conductive sheath 222 (e.g., the path of least resistance for current flow, normally the closest distance between the flat coil and the sheath) is between the distal end 221 and the distal side edge 223 of the flat coil 220 and the conductive sheath 222, respectively. In one or more examples, the arcing region will initially begin more particularly at the distal end 221 of the flat coil 220 that is located at the very end of the coil.

FIG. 18 illustrates a perspective view of an exemplary flat coil 220 of an electrode assembly, such as the electrode assembly 200 of FIG. 17. As shown in FIG. 18, the flat coil 220 is shaped as a flat wire with a rectangular cross-section that loops around a central axis in a series of coils. In one or more examples, and as will be discussed below, the flat coil 220 can be disposed on an inner surface of the insulation sheath 240 of the electrode assembly 200. In such configuration, the flat coil 220 can include a flat planar inner surface near the distal end 221 of the flat coil 220 that is on a side opposite to the inner surface of the insulation sheath 240. In one or more examples, the flat coil 220 can be manufactured via laser-cutting the shape of the flat coil 220 from an erosion resistant metal tubing, such as stainless steel, platinum, palladium, iridium, molybdenum, tungsten, or copper tubing.

FIG. 19 illustrates a perspective view of an exemplary flat coil 320 with cross ties of an electrode assembly, which can also be used in devices such as the electrode assembly 200 of FIG. 17. As shown, the flat coil 320 is shaped similarly to the flat coil 220 of FIG. 18, with a rectangular cross-section that loops around a central axis in a series of coils. Distinct from the flat coil 220 of FIG. 18, however, the flat coil 320 has a number of cross ties 323 that extend between the successive turns of the flat coil 320. That is, the cross ties 323 bridge the gap between each turn of the coil. Similar to the flat coil 220 of FIG. 18, the flat coil 320 can be disposed on an inner surface of an insulation sheath such as the insulation sheath 240 such that the flat coil 320 includes a flat planar inner surface near the distal end 321 of the flat coil 320 that is on a side opposite to the inner surface of the insulation sheath 240. In one or more examples, the cross ties 323 can provide improved structural stability for the flat coil 320. In one or more examples, the flat coil 320 can be manufactured via laser-cutting the shape of the flat coil 320 from an erosion resistant metal tubing, such as stainless steel, platinum, palladium, iridium, molybdenum, tungsten, or copper tubing.

FIG. 20 illustrates a perspective cross-sectional view of an exemplary electrode assembly 200 of a cathode. As shown in FIG. 20, the flat coil 220 has a number of individual coils 225 (i.e., "turns" of the flat coil 220) that are each disposed on an inner surface 243 of the insulation sheath 240. In one or more examples, the flat coil 220 can be bonded to the insulation sheath 240 by an adhesive. The adhesive (not shown) can be applied between the coils 225 of the flat coil 220 and be permitted to wick around the inner surface 243 of the insulation sheath 240 such that the adhesive fills the area between each adjacent coils 225 and secures the flat coil 220 to the insulation sheath 240.

FIG. 21A illustrates a left side cross-sectional view of an exemplary electrode assembly 200 of a catheter and FIG. 21B illustrates a front view of the exemplary electrode assembly 200 of FIG. 21A, showing the cutting plane used to generate the cross-sectional view of FIG. 21A. As discussed above, the flat coil 220 of the electrode assembly 200 can have a rectangular cross-section and include a flat planar inner surface that is on a side opposite to the inner surface of the insulation sheath 240. This is shown more clearly in FIG. 21A, which illustrates that the flat coil 220 has a rectangular cross-section that is disposed on the inner surface of the insulation sheath 240. As visible near the distal end 221 of the flat coil 220, the flat coil has a planar inner surface that is on a side opposite the inner surface of the insulation sheath 240.

Returning now to FIG. 17, the electrode assembly 200 can also include two insulated wires 230, 232, extending along the length of the catheter. In particular, a first insulated wire 230 can be electrically connected to the flat coil 220, and a second insulated wire 232 can be electrically connected to the conductive sheath 222. In one or more examples, the insulated wires 230, 232 can provide an electrical connection between the flat coil 220, the conductive sheath 222, and an external voltage source, e.g., a high voltage pulse generator (not pictured). In one or more examples, the flat coil 220 can be connected to a positive terminal of the voltage source, with the conductive sheath 222 connected to a negative terminal of the voltage source or to ground. Alternatively, the flat coil 220 can be connected to a negative terminal of the voltage source or to ground while the conductive sheath is connected to a positive terminal of the voltage source. The conductive portions of the wires 230, 232 can be heat-sealed or otherwise fixed to the conductive sheath 222 and the flat coil 220 to provide a direct electrical connection. In one or more examples, the insulated wires 230, 232 can extend within a fluid lumen of the catheter, e.g., fixed to a side wall of the lumen or disposed within grooves extending along the lumen. The wires 230, 232 can also extend through a separate lumen of the catheter, e.g., a wire lumen. In one or more examples, the wires 230, 232 can be insulated copper wires.

In one or more examples, a series of high voltage pulses can be transmitted across the wires 230, 232 by an external voltage source, e.g., a pulsed high voltage source, to generate a series of shockwaves and/or cavitation bubbles at the electrode assembly 200. Negative and positive terminals of the external voltage source can be connected to the proximal ends of the first insulated wire 230 and the second insulated wire 232, thereby creating a potential difference across the flat coil 220 and the conductive sheath 222 (i.e., an electrode pair of the electrode assembly) when high voltage pulses are delivered across the wires 230, 232. The potential difference can cause current to flow between the electrode pair to generate shockwaves and/or cavitation bubbles. In one or more examples, the direction of the current flow can be dependent on the polarity of the electrodes, with current flowing from the more positively charged electrode (i.e., the electrode connected to the positive terminal of the voltage source via one of the wires 230, 232) to the more negatively charged electrode (i.e., the electrode connected to the negative terminal of the voltage source via one of the wires 230, 232). The duration and magnitude of each of the voltage pulses can be sufficient to generate a gas bubble (e.g., a cavitation bubble) on the surface of the electrodes (i.e., on the distal end 221 of the flat coil 220 and the distal side edge 223 of the conductive sheath 222).

In one or more examples, the magnitude and other characteristics of the shockwaves and/or cavitation bubbles generated can be controlled by adjusting the magnitude and duration of the applied voltage pulses. For instance, delivering relatively lower voltages at high repetition rates (e.g., voltages between about 800 V and 2000 V and repetition rates between about 20 Hz and 200 Hz) can generally produce cavitation bubbles on the electrodes. Delivering relatively higher voltage pulses at lower repetition rates (e.g., voltages between about 2500 V and 6000 V and repetition rates between about 1 Hz and 4 Hz) can generally produce acoustic shockwaves with a higher magnitude relative to cavitation bubbles. For directional lithotripsy electrode assemblies and emitters as considered herein, implementations using lower voltages at high repetition rates has been found to be advantageous to achieve the desired ablative mode of action. Accordingly, embodiments of the present disclosure can be implemented using voltages from about 200 V to about 10,000 V, and more particularly using voltages from about 1,500 V to 2,000 V, and increments and gradients of voltage within these ranges (e.g., 1.60 kV, 1.70 kV, 1.80 kV, 1.90 kV). Similarly, electrode assemblies and emitters as considered herein can be implemented using frequencies such as from about 50 Hz to 500 Hz, from about 100 Hz to 200 Hz, from about 125 Hz to 175 Hz, and at increments and gradients of frequency within that range. In one or more examples, the characteristics of the shockwaves and/or cavitation bubbles can also be controlled by adjusting structural aspects of the electrode assembly, e.g., the distance between electrodes of an electrode pair, the surface area of the electrodes, the shape of the electrodes, etc.

When a series of relatively lower voltages at high repetition rates are transmitted across the wires 230, 232, a plurality of gas cavitation bubbles can accumulate on the surface of the electrodes (e.g., at the distal end 221 of the flat coil 220 and the distal side edge 223 of the conductive sheath 222) of the electrode assembly 200. In one or more examples, cavitation bubbles formed on the surface of the electrodes can flow out through an open tip of the catheter and into a treatment site to break up a calcified lesion. When a series of relatively higher voltages at low repetition rates are transmitted across the wires 230, 232, a plasma arc of electric current can form across a bubble generated at the arcing region between the electrodes (i.e., at the closest distance between the distal end 221 of the flat coil 220 and the distal side edge 223 of the conductive sheath 222). The electric current can traverse the bubble, thereby creating a rapidly expanding and collapsing bubble that produces an acoustic shockwave that propagates outward from the catheter toward a treatment site to break up a calcified lesion.

In contrast with solid cylindrical conductive elements used as an electrode, the flat coil 220 provides a guide for controlled erosion. Whereas a simple cylinder (as part of an electrode pair) will degrade in a somewhat random pattern as current travels across the electrode pair, the flat coil 220 takes advantage of the inclination of electrical current to traverse the shortest path from one electrode across to the other electrode of an electrode pair. Accordingly, the distal end 221 of the flat coil will generally be along the path of least resistance, or in other words, at the shortest distance between the flat coil 22 and the conductive sheath 222. The erosion of flat coil 220 will tend to occur at the distal end 221, consistently moving the distal end 221 back as the flat coil 220 shortens (which in the example of FIG. 17, would be in a clockwise direction). While the location of the distal end 221 will move as erosion processes, the consistency of the location of the spark gap at the distal end 221 is relatively not as random as would be observed along the edge of a solid cylinder. Thus, the flat coil 220 can provide for a sequence of shock waves and cavitation bubbles with a more consistent origin point and less potential for interference over the course of a treatment regimen.

FIG. 22 is a graph showing estimated measurements of pressure generated by a device fabricated in accordance with FIG. 17, focusing on the initial period of the spark generation, before cavitation bubbles are formed. The estimated measurements depicted in FIG. 22 are depicted in megapascals (MPa) and were based off measurements by a hydrophone located about 10 mm from the emitter location. As shown, there exists a large positive spike of about 4.2 MPa, followed by a negative spike to a magnitude of –2.03 MPa, resulting with a peak-to-peak magnitude of 6.23 MPa. The peak-to-peak magnitude of 6.23 MPa can enhance the breaking up of lesions at a treatment site.

In one or more examples, the rise time can be correlated with the efficacy of a catheter that incorporates an electrode design such as the electrode assembly 200 of FIG. 17. That is, a fast rise time can enhance the performance of the catheter when attempting to bore through a calcified lesion. As shown in FIG. 22, the positive peak has a relatively fast rise time with a narrow apex before falling, thus, a device fabricated according to FIG. 17 can perform better than other devices with slower rise times and/or wider peaks (which can be indicative of a slower pressure differential). As shown here, the positive and negative spikes in pressure are caused by the spark generation itself. Subsequently in a cycle of firing the electrode assembly, a positive spike can be caused by the initial bursting of a vapor bubble with the negative spike caused by the collapse of that bubble.

In one or more examples, the pressure magnitude and frequency resulting from the voltage pulses can be controlled to improve the characteristics of the acoustic pressure waves. For instance, delivering voltage pulses with relatively short pulse widths, e.g., below 50 microseconds, can produce acoustic pressure waves with relatively high amplitude negative pressures. Increased negative pressures can provide a negative suction-like force that may facilitate the clearing of lesions and debris from a treatment site. In one or more examples, the voltage pulses can be delivered across an electrode pair at relatively low frequencies, e.g., frequencies between 30-40 Hz, between 40-50 Hz, or greater than 50 Hz. Similarly in one or more examples, the voltage pulses can have relatively short pulse widths, e.g., pulse widths between 2-20 microseconds, pulse widths of about 5 microseconds, pulse widths of about 10 microseconds, or less than 2 microseconds, to produce acoustic pressure waves having high negative pressure.

As discussed above, as shockwaves and/or cavitation bubbles are generated by voltage pulses transmitted across an electrode pair, the electrode surface can slowly erode at the arcing region between the electrodes. FIG. 23 illustrates a perspective view of the exemplary electrode assembly 200 of FIG. 17 before any erosion. As mentioned above, the initial arcing region can generally be located at the path of least resistance between the electrodes of the electrode pair. Referring to FIG. 23, the path of least resistance between the flat coil 220 and the conductive sheath 222 (i.e., the electrodes) will be the location where the gap between the flat coil 220 and the conductive sheath 222 is the shortest and not obstructed by the insulation sheath 240. As shown in FIG. 23, the initial arcing region can thus be located between the distal end 221 of the flat coil 220 and the distal side edge 223 of the conductive sheath 222.

Repeated generation of shockwaves and/or cavitation bubbles by applying voltage to the electrode assembly 200 can then cause the electrodes to erode proximate to the initial arcing region. This is shown more clearly in FIG. 24A and FIG. 24B, which illustrate an enlarged detail view of the erosion process of the electrodes of the electrode assembly 200 of FIG. 17. As shown in FIG. 24A, the distal side edge 223 of the conductive sheath 222 has begun to erode at the arcing region where the distal side edge 223 of the conductive sheath 222 is closest to the distal end 221 of the flat coil 220. In one or more examples, erosion will begin on the conductive sheath 222 before beginning on the flat coil 220.

For instance, as shown in FIG. 24A, the distal edge 223 of the conductive sheath 222 has begun to erode, but the distal end 221 of the flat coil 220 has not. As shown in FIG. 24A, however, the distal end 221 of the flat coil 220 has begun to erode. Thus, the erosion of the distal side edge 223 of the conductive sheath 222 can be more extensive relative to the erosion of the distal end 221 of the flat coil 220 (as visible in FIG. 24B), because the erosion began on the conductive sheath 222 before beginning on the flat coil 220.

In one or more examples, the insulation sheath 240 will also erode based on the application of voltage to the electrode assembly 200. As shown in FIG. 24A, the distal edge 241 of the insulation sheath 240 began after the erosion of the distal side edge 223 of the conductive sheath 222. It is contemplated, however, that the insulation sheath 240 may begin to erode before the conductive sheath 222 begins to erode. As the conductive sheath 222 and the insulation sheath 240 erode, the erosion can expose an outer surface 227 of the flat coil 220, as shown in FIG. 24A as part of distal end 221. In one or more examples, the erosion of the insulation sheath 240 can permit the erosion of the flat coil 220 to begin. The exposure of the outer surface 227 of the flat coil 220 can permit the arcing region to shift; wherein rather than proceeding between the distal end 221 of the flat coil, the arcing region may proceed between the outer surface 227 of the flat coil 220 and the distal side edge 223 of the conductive sheath 222. In one or more examples, rather than shifting, however, the arcing region may expand. That is, the arcing region may proceed between the entire exposed region of the flat coil, including both the distal end 221 and the exposed outer surface 227, and the distal side edge 223 of the conductive sheath 222.

As the erosion begins to wear away the distal end 221 of the flat coil 220, the arcing region can proceed to follow the coils of the flat coil 220. That is, in one or more examples, the arcing region can follow the end of the flat coil 220 as the coil erodes. As seen in FIG. 24B, the progressive erosion of flat coil 220 can lead to the region of exposed outer surface 227 being completely eroded and therefore no longer present; of course, as degradation continues further regions of exposed outer surface 227 may be cyclically exposed and then eroded. Therefore, the inclusion of the flat coil 220 as one of the electrodes of the electrode assembly 200 can permit the erosion of the electrodes to proceed in a semi-controlled predictable manner that follows the flat coil 220. This erosion progression is shown in FIGS. 25A and 25B, with FIG. 25A illustrating the electrode assembly 200 after the initial erosion begins, and FIG. 25B illustrating the electrode assembly after extensive erosion has occurred. Further, erosion that is controlled by the presence of the material of the flat coil 220 can provide for a relatively more even or uniform erosion pattern that progresses around the circumference of the conductive sheath 222.

As shown in FIG. 25A, the erosion of the conductive sheath 222 and the insulation sheath 240 has begun at the initial arcing region near the end of the flat coil 220, but the erosion of the flat coil 220 has not yet begun. In contrast, FIG. 25B depicts extensive erosion, illustrated by the deformed shape of both the conductive sheath 222 and the insulation sheath 240 at the distal side edges 223 and 241, respectively. Relative to FIG. 25A, the flat coil 220 shown in FIG. 25B has eroded to remove entire turns of the flat coil 220 (the end of which is no longer visible because it has eroded along the turns of the coils).

As discussed above, in a circuit, current can generally flow from a positively charged source to a negatively charged source. Moreover, the positive and negative terminals of a voltage source can be connected via the wires 230 and 232 to the flat coil 220 and the conductive sheath 222. In one or more examples, if the flat coil 220 is connected to the negative terminal and the conductive sheath 222 is connected to the positive terminal, the erosion can begin on the conductive sheath 222 first. Alternatively, in examples where the flat coil 220 is connected to the positive terminal and the conductive sheath 222 is connected to the negative terminal, the erosion may begin on the flat coil 222 first. Accordingly, reversing the polarity of the electrode assembly (e.g., by swapping which electrode is connected to the positive or negative terminal, also referred to as "polarity switching") can cause the current to flow in the opposite direction across the arcing region. Altering the direction of the current flow can impact which electrode of the electrode assembly 200 experiences the most erosion.

In one or more examples, the surface area difference between the electrodes can impact the longevity of the device. A first electrode with a larger surface area relative to a second electrode may be able to withstand more erosion than the smaller second electrode. As evident in FIG. 17, the conductive sheath 222 has a greater surface area than the flat coil 220. Thus, in one or more examples, designing the electrode assembly 200 such that erosion occurs primarily on the conductive sheath 222 may enable the electrode assembly 200 capable of performing a longer treatment than if the erosion occurred primarily on the flat coil 220.

In one or more examples, the usable lifespan of an electrode assembly such as the electrode assembly 200 can be extended by switching the polarity of the electrodes one or more times during the treatment procedure. For instance, U.S. Pat. No. 10,226,265 describes switching the polarity of voltage pulses applied across an electrode pair to switch the direction of current flow during a procedure. As described previously, an electrode connected to a positive terminal of a voltage source may generally experience increased erosion compared to an electrode connected to a negative terminal or to ground. Accordingly, switching the polarity of an electrode assembly during a procedure can allow a user to control the relative erosion at the surface of each electrode of an electrode pair. Over the course of a treatment procedure, polarity switching can be used to more evenly distribute erosion across both electrodes of an electrode pair, increasing the useable lifespan of an electrode assembly.

In one or more examples, the electrode assembly 200 can be used in a catheter that implements the above polarity switching technique. Polarity switching can be implemented using a controller, e.g., a polarity switching circuit and/or a multiplexer, in electrical connection with the external voltage source and the electrode assembly. As discussed above, an external voltage source connected to the electrode assembly 200 can be configured to selectively deliver a series of high voltage pulses across the wires 230 and 232 to cause current to flow in a particular direction across the electrodes (i.e., from the positive electrode to the negative electrode). Thus, in one or more examples, a controller can be configured to control the direction of current flow across the electrodes (e.g., the conductive sheath 222 and the flat coil 220) of the electrode assembly 200 by altering the polarity of the electrodes. In one or more examples, the controller can be configured to switch the polarity after a specified duration or after certain number of pulses. For example, the polarity of the electrode assembly can be switched after a specified number of minutes, after a specified number of seconds, after every voltage pulse, after a specified number of pulses, etc.

In one or more examples, the controller may be configured to alter polarity based on readings from a sensor in electrical connection with the controller. For example, the sensor may be configured to measure operating parameters such as the current flow, voltage pulse width, time between voltage pulse and the initiation of a shockwave or cavitation bubble, temperature of one or more of the electrodes, and other such measurable parameters and characteristics of a functional catheter. The controller may be configured to alter the polarity based on a given parameter exceeding a predetermined threshold. In one or more examples, the sensor can measure the current flow across the electrodes and the controller can automatically switch the polarity of the electrode assembly when the current falls below a predefined threshold (e.g., a threshold that indicates the current flow has decreased because of electrode erosion). In one or more examples, the sensor can measure the temperature proximate to the electrodes and the controller can automatically pause or terminate current flow to the electrode assembly when the current falls exceeds a predefined threshold (e.g., a threshold that indicates the temperature of the electrodes is above a target operating status). The controller can also be configured to terminate the delivery of voltage pulses when a measured parameter is greater or lower than a termination threshold value. In one or more examples, the termination threshold values can signify an error mode or undesirable operating conditions.

In one or more examples, the electrode assembly 200 can be used with a catheter to treat an occlusion (e.g., lesions) in a body lumen, such as calcified lesions in vasculature associated with arterial disease. As described above, the electrode assembly 200 can be configured to generate one or more shockwaves and/or cavitation bubbles in response to the application of voltage across the electrodes (e.g., the conductive sheath 222 and the flat coil 220) of the electrode assembly 200. When placed within a catheter, the shockwaves and/or cavitation bubbles created by the electrode assembly 200 can be directed towards occlusions in a treatment area, and can begin to break apart the occlusions as described above.

FIG. 26 illustrates a perspective view of the distal end of an exemplary catheter 201, according to one or more embodiments. The catheter 201 can include an annular catheter body, such as the elongated tube 260. The elongated tube 260 can be formed from a rigid or semi-rigid material, such as a shaped polymeric material. As shown in FIG. 26, the catheter 201 includes an electrode assembly 200 mounted at the distal end of the catheter 201 within the elongated tube 260. In one or more examples, the electrode assembly 200 can be as described above and can include a conductive sheath mounted within the elongated tube 260, an insulation sheath mounted circumferentially within the conductive sheath, and a flat coil disposed on an inner surface of the insulation sheath. (Alternative implementations of the electrode assembly can have other structures as described herein, for example, using a cylindrical inner electrode instead of a flat coil electrode as illustrated.) Thus, in one or more examples, the catheter 201 can be configured to deliver one or more shockwaves and/or cavitation bubbles to a treatment site when a voltage pulse is applied across the flat coil and the conductive sheath of the electrode assembly 100 to create an arcing region as described above.

As shown in FIG. 26, the catheter 201 also includes a number of aspiration ports 266, as well as a fluid lumen 252, an aspiration lumen 254, and optionally a guidewire lumen 256. The guidewire lumen 256 can be sized to receive a guidewire that can be used to position the catheter 201 within a body cavity or lumen. To position the catheter 201, a guidewire can be inserted through the guidewire lumen 256 and used to locate the elongated tube 260 of the catheter 201 proximate to a treatment site. In one or more examples, the catheter 201 can be configured without the guidewire lumen 256 (e.g., for a rapid exchange implementation of the catheter assembly).

The lumens of the catheter 201 are shown more clearly in FIG. 27A, which illustrates a left side cross-sectional view of the distal end of an exemplary catheter such as the catheter 201 cut across the cutting plane shown in FIG. 27B, which illustrates a front view of the distal end of the catheter.

In one or more examples, the fluid lumen 252 can be configured for flowing a fluid along the length of the catheter body and through a fluid outflow port 262 at the distal end of the catheter 201. The aspiration lumen 254 can be configured to receive debris from the treatment site through a fluid inflow port 264 at the distal end of the catheter 201 and/or through the aspiration ports 266 shown in FIG. 26. In one or more examples, the catheter 201 can provide inward suction that causes fluid to be drawn into the aspiration lumen 254 and further enables the catheter 201 to circulate fluid through the treatment site by supplying fluid via the fluid lumen 252 and removing fluid via the aspiration lumen 254. For example, as shown in FIG. 27A, the arrows illustrate the fluid flow, which exits the catheter 201 (arrow F1) through the fluid outflow port 262, and subsequently enters the catheter at one or more of the fluid inflow port 264 (arrow F2) and the aspiration ports 266 (arrows F3), ultimately returning down to the proximal end of the catheter 201.

As shown in FIG. 27A, the electrode assembly 200 is mounted within the fluid lumen 252 of the catheter 201. In one or more examples, the fluid conveyed through the fluid lumen 252 can be a conductive fluid. Thus, in one or more examples, the conductive fluid flowing through the fluid lumen 252 flows through the electrode assembly before exiting the catheter 201. The conductive fluid can provide a path for current to flow between the flat coil 220 and the conductive sheath 222, thereby enabling the generation of shockwave and/or cavitation bubbles during a treatment. In one or more examples, the shockwave and/or cavitation bubbles created can flow out of the fluid outflow port 262 of the catheter 201 towards the treatment location.

FIGS. 28A and 28B illustrate perspective views of exemplary electrode assemblies 400 and 450 having an interior coiled electrode 420 with a curved distal tip 421. Similar to the embodiments shown in FIGS. 25A and 25B, the interior coil electrode 420 (shown here as a flat coil) is positioned within a cylindrical outer electrode 422 (alternatively referred to as a conductive sheath) with an insulation layer 440 therebetween. A first insulated wire 430 is electrically connected with the interior coil electrode 420 and a second insulated wire 432 is electrically connected with the cylindrical outer electrode 422. In contrast with the embodiments shown in FIGS. 25A and 25B, the curved distal tip 421 is bent so as to be initially centered within the circumference of the concentric cylindrical outer electrode 422 and insulation layer 440. Because bubble erosion occurs where spark travels across the electrodes, in the embodiments of FIGS. 25A and 25B, that erosion will start at the edge of the outer electrode where the distal end and edge of the flat coil is located. Accordingly, with the distal end of a coil located at the edge of the cylinder, the erosion will initiate at an off-center position. In FIGS. 28A and 28B, the curved distal tip 421 of the interior coiled electrode 420 moves the initial spark gap location to the center of the cylindrical electrode assembly, which can further aid in directing a relatively even erosion of the cylindrical outer electrode 422. Moreover, initiating the sparks and generated shock waves to the center of the electrode assembly 400 can align and center the cavitation bubbles formed by the electrode assembly. The centered location of bubble formation, being aligned with the centerline or longitudinal axis of the overall catheter, can provide for greater precision in delivering shock wave treatment.

The difference between the electrode assembly 400 in FIG. 28A and the electrode assembly 450 in FIG. 28B is a difference in how the interior coil electrode 420 is positioned. In FIG. 28A with electrode assembly 400, the interior coil electrode 420 is flush (or near flush) with the distal edge of the cylindrical outer electrode 422. In FIG. 28B with electrode assembly 450, the interior coil electrode 420 is recessed a distance within insulation layer 440 away from the distal edge of the cylindrical outer electrode 422. The depth by which interior coil electrode 420 is recessed can be equal to the width of one, two, three, or three or more turns of the interior coil electrode 420. In the embodiment of FIG. 28B, the recessed location of the spark gap and subsequent shockwave can lead to bubble formation that is at least partially within the barrel of the electrode assembly 450 lumen as defined by the insulation layer 440 and cylindrical outer electrode 422. Accordingly, the expansion of a cavitation bubble formed within that lumen is primarily directed out the distal end of the electrode assembly 450, imparting corresponding directionality to the bubble and shock wave treatment.

While erosion of the interior coil electrode 420 will eventually progress toward the cylinder walls, the centered location of the initial sparks and bubble formation may have a continuing effect throughout a cycle of shock wave generation and treatment. In other words, due to physical factors such as residual electrical potential, the fluid dynamics trailing a prior bubble formation, and the like, subsequent bubbles may also be formed in a centered location aligned with the centerline of the overall catheter even though the curved distal tip 421 will be fully eroded and the eroding distal end of the interior coil electrode 420 will be alongside the interior wall of the insulation layer 440.

FIG. 29 illustrates a perspective view of an exemplary electrode assembly 500 having an exterior coiled electrode 522 and a solid tube interior electrode 520, with an insulation layer 540 therebetween. In this embodiment, first insulated wire 530 is electrically connected to exterior coiled electrode 522 and second insulated wire 532 is electrically connected to solid tube interior electrode 520. As noted herein, when implementing polarity switching, it can be advantageous for longevity of the overall device for a solid cylindrical element to be the electrode that is primarily connected to the positive terminal of the voltage source. As shown here, when the cylindrical conductive element of solid tube interior electrode 520 is paired with the flat coil of exterior coiled electrode 522 as the complementary electrode, the ratio of how frequently the solid tube interior electrode 520 receives current acting as the positive terminal can lead to that solid cylindrical element getting hotter than the exterior coiled electrode 522. Accordingly, the wire connecting to the positive terminal of the voltage source (in this implementation being the second insulated wire 532) is moved to be in electrical communication with the solid tube interior electrode 520 to thereby localize and control the heat of the device. The erosion of the exterior coiled electrode 522 and solid tube interior electrode 520 and corresponding shockwave and bubble formation can mirror the embodiments described herein, such as in FIG. 17.

FIG. 30 illustrates a perspective view of an exemplary electrode assembly 600 having an exterior clockwise coiled electrode 622 and an interior counterclockwise coiled electrode 620. In this embodiment, insulation layer 640 is positioned between the two coiled electrodes, with first insulated wire 630 connected to interior counterclockwise coiled electrode 620, and with second insulated wire 632 connected to exterior clockwise coiled electrode 622. The use of two coils twisted in opposing directions further works to maintain a consistency in the spark position and location of shock wave formation. In this implementation, current will travel across between the distance between interior coil distal tip 621 and the exterior coil distal tip 623 and erosion will primarily occur at these locations. As each of the exterior clockwise coiled electrode 622 and the interior counterclockwise coiled electrode 620 are degraded, the respective the exterior coil distal tip 623 and interior coil distal tip 621 will erode and move around the circumference of the insulation layer 640 therebetween. The distance between the exterior coil distal tip 623 and interior coil distal tip 621 will vary as erosion of each element progresses, but that distance will be no greater than the diameter of the insulation layer 640. Accordingly, on average, the spark gap distance between the interior coil distal tip 621 and the exterior coil distal tip 623 as erosion progresses will be maintained within a desired range. Moreover, because each electrode is a coil having their respective distal tips degraded, this implementation can avoid the risk of a permanent erosion bias developing on one side or area of an electrode. It should be readily understood that in an alternative implementation, an exterior coil electrode can be wound in a counterclockwise direction and an interior coil electrode can be wound in a clockwise direction.

FIG. 31A illustrates a perspective view of an exemplary electrode assembly 700 having an outer electrode 722 with erosion-control gaps 729 arranged in a pattern around the surface of the outer electrode 722. In this implementation, the inner electrode is a flat coil 720 having a curved distal tip 721 which is bent so as to be initially centered, with an insulation layer 740 layered in between the flat coil 720 and the outer electrode 722. A first insulated wire 730 is electrically connected to outer electrode 722 and a second insulated wire is electrically connected to the flat coil 720. As noted in FIG. 2, a cylindrical electrode manufactured as a rolled hypotube will often have electrical current tend to arc at locations where there is a sharp edge or corner, and thus erosion will tend to track down a scam of the rolled hypotube material. Taking advantage of the tendency of electrical current to arc toward sharp edges, the electrode assembly 700 implementation as shown in FIG. 31A uses the erosion-control gaps 729 to draw the arc of current around the full circumference of the outer electrode distal edge 723 as the outer electrode 722 erodes. Specifically, as erosion of the outer electrode 722 progresses from the distal to the proximal end of the electrode assembly 700, corresponding with the outer electrode distal edge 723 eroding back in the proximal direction along the length of electrode assembly 700, the forwardmost erosion-control gaps 729 in the outer electrode 722 will become exposed as points for electrical current to arc toward and generate sparks. Accordingly, the location of outer electrode 722 erosion can be localized at the distal-most exposed sharp edges of the erosion-control gaps 729.

As erosion of the outer electrode distal edge 723 continues, and as the forwardmost erosion-control gaps 729 are degraded, different (relatively proximate) erosion-control gaps 729 will become exposed and present a shorter distance for spark gaps and current arcing. Thus, the location of sparking and erosion will tend toward the sharp edges of the erosion-control gaps 729 that are subsequently exposed. As the material around the subsequently erosion-control gaps 729 are degraded, the shortest distance for current arcing can return to previous erosion-control gaps 729 or to different further subsequent erosion-control gaps 729 in the outer electrode. By guiding the location of spark gaps to different areas of the outer electrode distal edge 723 by use of the structure of the erosion-control gaps 729, the overall degradation pattern of the outer electrode 722 can be maintained as relatively even, and thereby avoid directional bias or other physical failure risks resulting from uneven erosion of outer electrode 722.

The erosion-control gaps 729 are illustrated as each having an oblong shape, but in other aspects the erosion-control gaps 729 can have circular shapes, rectangular shapes, triangular shapes, diamond shapes, curved arcs, other geometrical shapes, or combinations thereof. In some aspects, the erosion-control gaps 729 pass through the complete thickness of outer electrode 722. In other aspects, erosion-control gaps 729 pass only partway through the thickness of outer electrode 722. The pattern of the erosion-control gaps 729 can be angled relative to each other in an alternating columns as shown in FIG. 31A. In alternative embodiments, the erosion-control gaps 729 can be patterned at angles parallel to each other, arranged in a gruyère pattern, patterned as rotationally offset rings when viewed along the length of the outer electrode 722, or otherwise arranged in a regular pattern. The erosion-control gaps 729 can be formed in outer electrode 722 by a laser-cutting process or the like as known in the field. It should be readily understood that any of the inner-located electrodes described herein can be used in combination with outer-electrode 722.

FIGS. 31B through 31E illustrate an exemplary progression of electrode degradation for outer electrode 722 having erosion-control gaps 729 in a cut-out patterning as shown in FIG. 31A. The progression of erosion region 713 is shown in FIG. 31B as having degraded outer electrode 722 and consuming most of the forwardmost erosion-control gap 729 and having reached a subsequent erosion-control gap 729' along the length of outer electrode 722. In FIG. 31C, erosion region 713 has spread in a relatively lateral direction (rightward in the figure) around the circumference of the outer electrode close to the next subsequent erosion-control gap 729'. In FIG. 31D, erosion region 713 has continued to spread in a relatively lateral direction (leftward in the figure) around the circumference of the outer electrode close to the next subsequent erosion-control gap 729" while also continuing to erode around the erosion-control gap 729'. Finally in FIG. 31D, the erosion control region 713 continues to degrade outer electrode 722 in a generally even manner, eroding electrode material relatively equally around erosion-control gaps 729' and 729". Accordingly, the erosion-control gap 729 in outer electrode 722 prevent the development of an uneven and irregularly shaped electrode edge over the normal course of degradation due to sparking and cavitation bubble formation.

In alternative embodiments of the various outer-located electrodes described above, a seamless hypotube can be used to minimize current arcing that may result in uneven erosion of the respective electrode. Further, in the embodiments set forth above, it can be understood that the metals or alloys used for the various cylindrical or coiled electrodes, positioned in an interior or exterior location, can be made from erosion resistant materials such as stainless steel, platinum, palladium, iridium, molybdenum, tungsten, copper, or combinations thereof.

Experimental Example

FIGS. 32A through 32H, are paired sets of images and graphs capturing the action of an electrode assembly as descried herein, particularly in reference to FIG. 17. Specifically, each of FIGS. 32A through 32H show captured images from a high-speed video showing an exemplary electrode assembly generating a forward-directional vapor bubble. Paired with each image is a graph displaying the average pressure measurement (in MPa) over time (μs) for the electrode assembly generating such forward-directional vapor bubbles. The pressure measurements were taken by a hydrophone located about 10 mm from the emitter location. As noted above, the pressure close to the emitter (~1 mm) is about an order of magnitude greater than the pressure measured at the hydrophone 10 mm distant from the end of the emitter. The solid circle shown in each graph corresponds to the time of measurement and image capture in the associated image.

Figure 32A:
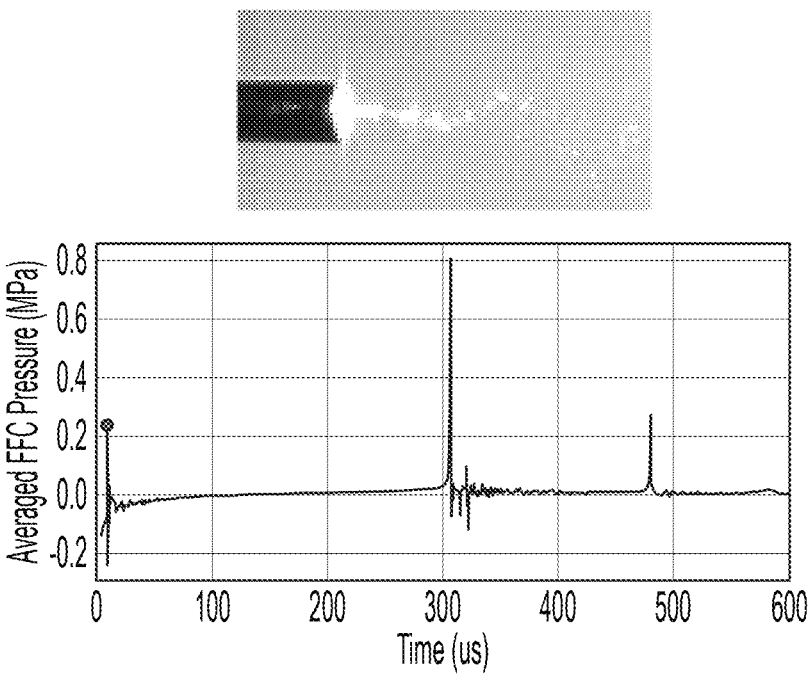
Figure 32B:
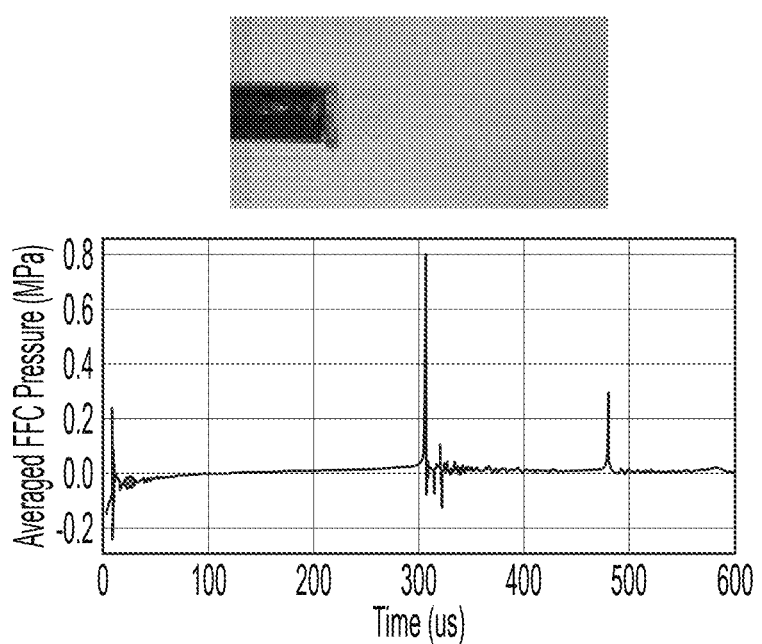
Figure 32C:
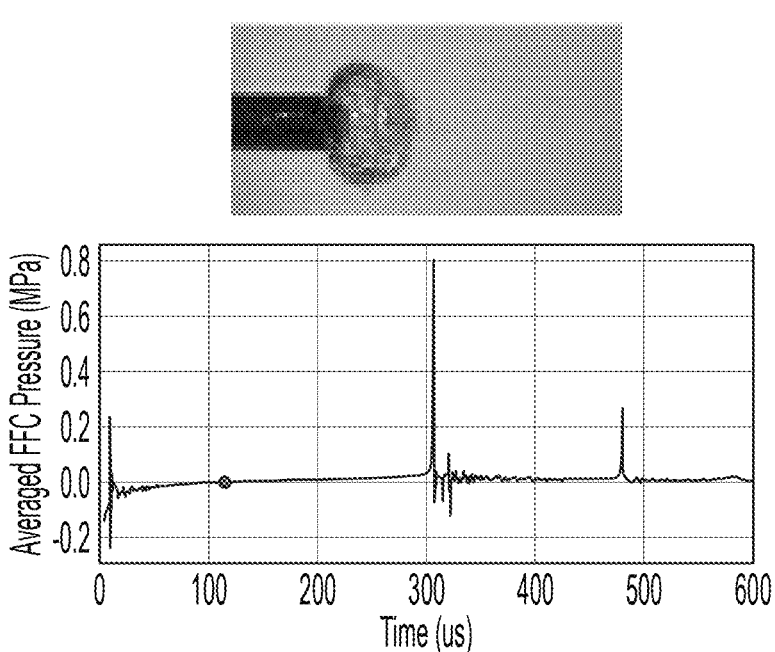
Figure 32D:
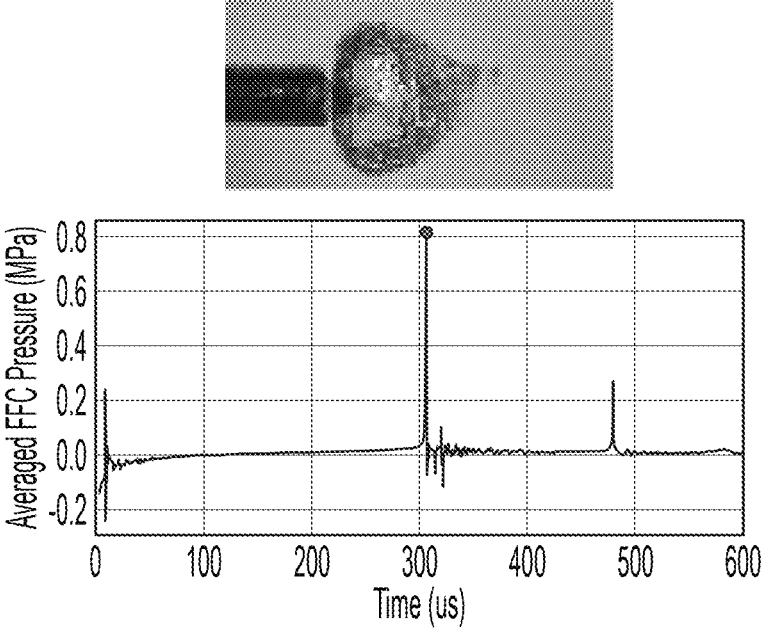
Figure 32E:
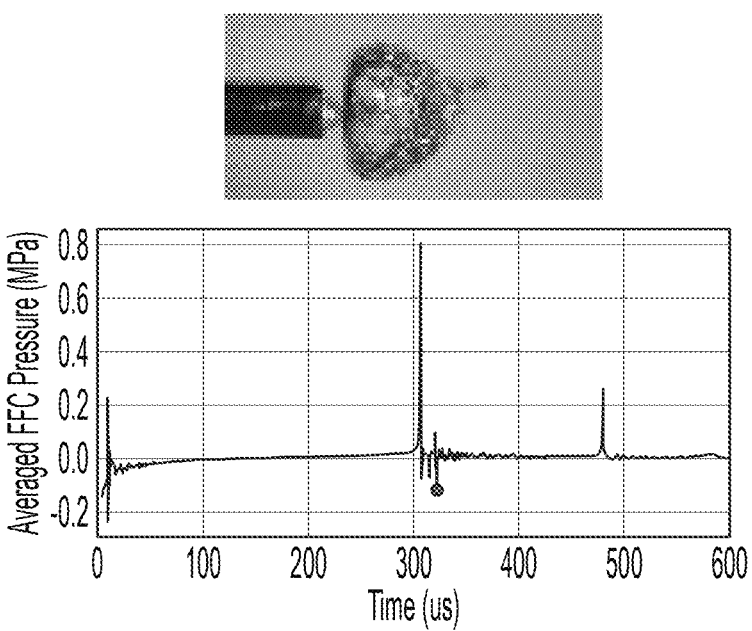
Figure 32F:
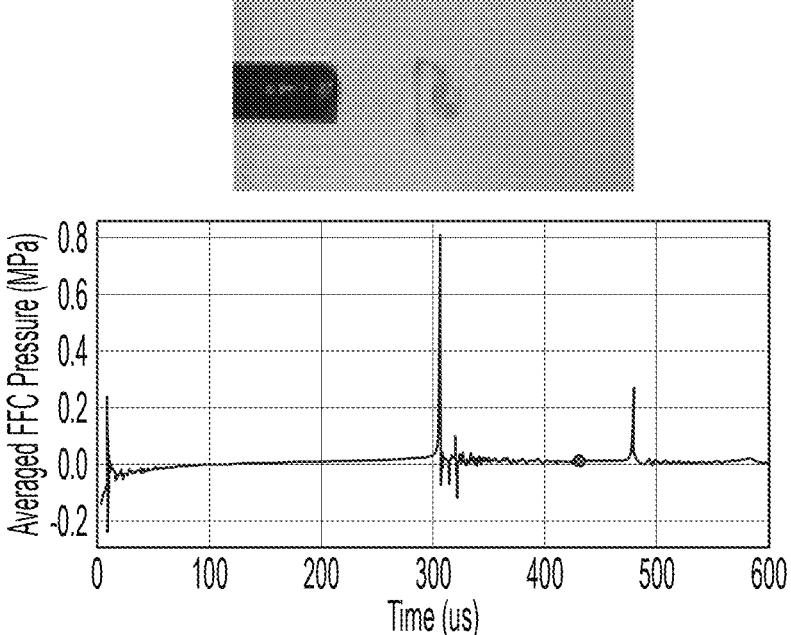
Figure 32G:
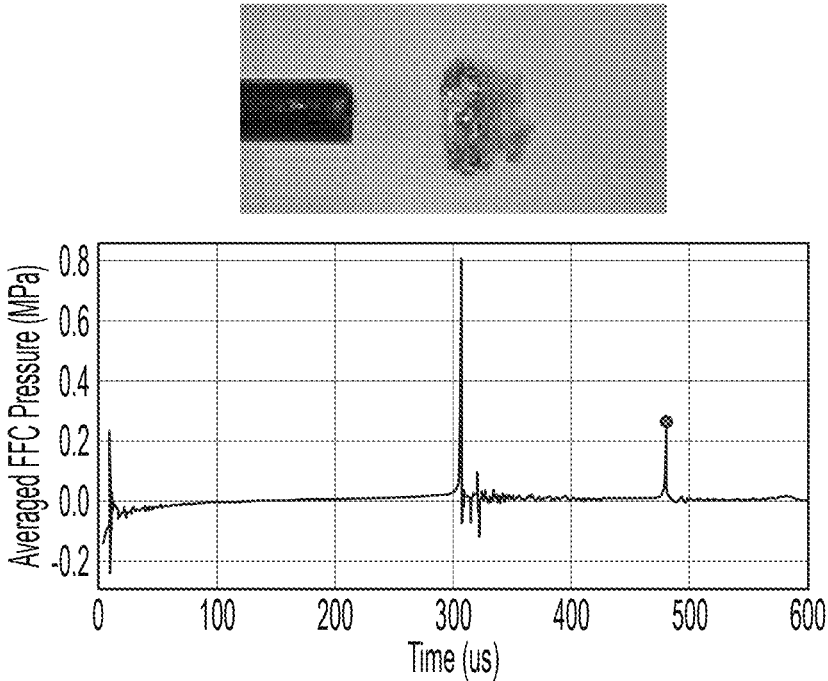
Figure 32H:
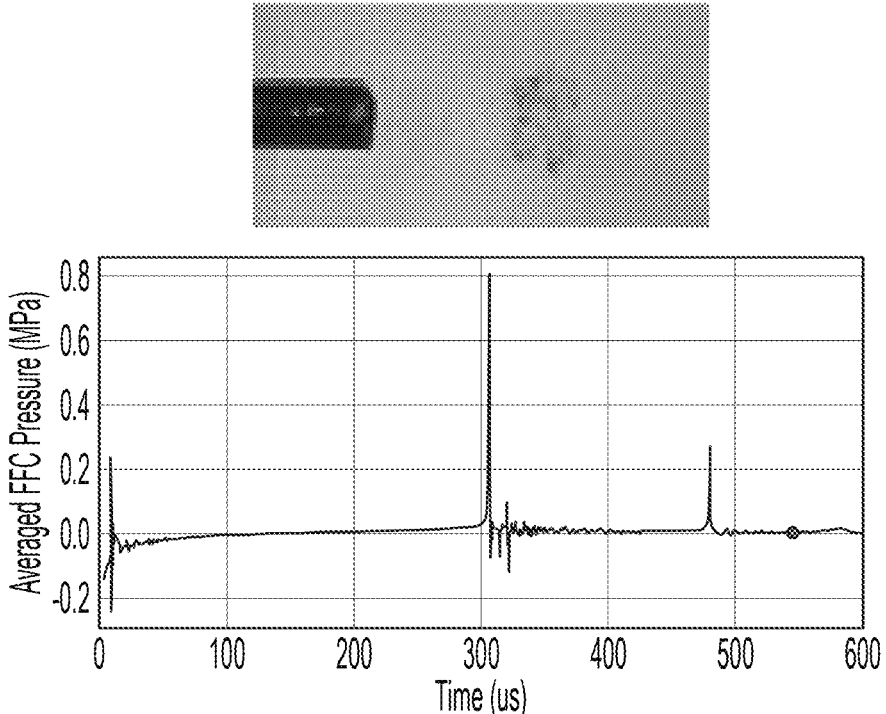

FIG. 32A shows the initial spark at the distal end of the electrode assembly; the pressure measured at this start point (close to zero microseconds) is about 0.25 MPa. FIG. 32B shows the moment immediately subsequent to the spark generation in FIG. 32A, with pressure dropped to just below about 0.0 MPa. FIG. 32C shows the formation of an initial bubble at beyond 100 μs after the spark generation; the pressure measured at this point remains close to about 0.0 MPa. FIG. 32D shows the beginning of the bubble breaking and collapse at about 300 μs; the pressure measured at this point peaks at just above about 0.8 MPa. FIG. 32E shows the continuation of the bubble collapse at about 325 μs; the pressure measured at this point drops down to about –0.1 MPa. FIG. 32F shows the dissipation of the initial bubble at about 440 μs; the pressure measured at this point is again about 0.0 MPa. FIG. 32G shows the formation of a secondary bubble driven by the fluid dynamic forces of the expansion and collapse of the initial bubble, occurring at about 480 μs; the pressure measured at this point is at a secondary peak of about 0.3 MPa. FIG. 32H shows the dissipation of the secondary bubble at about 550 μs after the spark generation; the pressure measured at this point is again about 0.0 MPa.

As understood from FIGS. 32A through 32H, the exemplary electrode assembly as described herein is fully capable of generating shock waves and cavitation bubbles that have a forward directionality. After a voltage pulse is applied a positive pressure spike is generated (e.g., as in FIG. 32D) and thereafter a negative pressure spike is generated (e.g., as in FIG. 32E). Moreover, the strength and pressure generated by these shock wave and bubbles is sufficient to implement IVL therapy and may have further application in ablative in vivo processes. The observed results of the exemplary electrode assembly track earlier understandings of IVL, where both an initial and a secondary bubble are generated with their respective pressures. In forward firing directional applications, both the initial and the secondary bubbles can be optimized to produce peak pressures that are both functional for delivering therapy to a tissue or other in vivo structure.

Although the electrode assemblies and catheter devices described herein have been discussed primarily in the context of treating coronary indications, such as lesions in vasculature, the electrode assemblies and catheters herein can be used for a variety of indications. For instance, similar designs could be used for treating soft tissues, such as cancer and tumors (i.e., non-thermal ablation methods), blood clots, fibroids, cysts, organs, scar and fibrotic tissue removal, or other tissue destruction and removal. Electrode assembly and catheter designs could also be used for neurostimulation treatments, targeted drug delivery, treatments of tumors in body lumens (e.g., tumors in blood vessels, the esophagus, intestines, stomach, or vagina), wound treatment, non-surgical removal and destruction of tissue, or used in place of thermal treatments or cauterization for venous insufficiency and fallopian ligation (i.e., for permanent female contraception). Further, the electrode assemblies and catheters described herein could also be used for tissue engineering methods, for instance, for mechanical tissue decellularization to create a bioactive scaffold in which new cells (e.g., exogenous or endogenous cells) can replace the old cells; introducing porosity to a site to improve cellular retention, cellular infiltration/migration, and diffusion of nutrients and signaling molecules to promote angiogenesis, cellular proliferation, and tissue regeneration similar to cell replacement therapy. Such tissue engineering methods may be useful for treating ischemic heart disease, fibrotic liver, fibrotic bowel, and traumatic spinal cord injury (SCI). For instance, for the treatment of spinal cord injury, the devices and assemblies described herein could facilitate the removal of scarred spinal cord tissue, which acts like a barrier for neuronal reconnection, before the injection of an anti-inflammatory hydrogel loaded with lentivirus to genetically engineer the spinal cord neurons to regenerate.

It should be noted that the elements and features of the example catheters illustrated throughout this specification and drawings may be rearranged, recombined, and modified without departing from the present invention. For instance, while this specification and drawings describe and illustrate several example electrode assemblies, the present disclosure is intended to include catheters having a variety of electrode configurations. Further, the number, placement, and spacing of the electrode pairs and assemblies can modified without departing from the subject invention.

It will be understood that the foregoing is only illustrative of the principles of the invention, and that various modifications, alterations and combinations can be made by those skilled in the art without departing from the scope and spirit of the invention. Any of the variations of the various catheters disclosed herein can include features described by any other catheters or combination of catheters herein. Furthermore, any of the methods can be used with any of the catheters disclosed. Accordingly, it is not intended that the invention be limited, except as by the appended claims.

The invention claimed is:

1. A catheter for treating an occlusion in a body lumen, the catheter comprising:

an elongated tube;

a cylindrical inner conductive sheath mounted within the elongated tube, the inner conductive sheath having an uninsulated distal side edge that extends circumferentially around a longitudinal axis of the cylindrical inner conductive sheath;

a cylindrical outer conductive sheath mounted circumferentially around the inner conductive sheath within the elongated tube, the outer conductive sheath having a distal side edge proximate to the distal side edge of the inner conductive sheath; and an insulation sheath mounted within the elongated tube between the outer conductive sheath and the inner conductive sheath, wherein when a voltage pulse is applied across the inner conductive sheath and the outer conductive sheath in a conductive fluid, current flows across an arcing region between the inner conductive sheath and the outer conductive sheath to generate cavitation bubbles and/or shock waves outside of the catheter to treat the occlusion.

2. The catheter of claim 1, wherein the elongated tube includes a fluid lumen for flowing conductive fluid along the catheter and through a fluid outflow port at a distal end of the catheter.

3. The catheter of claim 2, wherein the outer conductive sheath, the insulation sheath, and the inner conductive sheath are mounted within the fluid lumen such that fluid flowing through the fluid lumen flows through the inner conductive sheath.

4. The catheter of claim 1, wherein the elongated tube includes an aspiration lumen for removing debris from the body lumen.

5. The catheter of claim 1, wherein the elongated tube includes a guidewire lumen sized to receive a guidewire.

6. The catheter of claim 1, wherein the arcing region is located where the distal side edge of the outer conductive sheath is most proximate to the distal side edge of the inner conductive sheath.

7. The catheter of claim 6, wherein the distal side edge of the inner conductive sheath is configured to erode proximate to the arcing region, and wherein erosion of the inner conductive sheath causes current to flow across a secondary arcing region between the distal side edge of the inner conductive sheath and the distal side edge of the outer conductive sheath.

8. The catheter of claim 6, wherein the distal side edge of the outer conductive sheath is configured to erode proximate to the arcing region, and wherein erosion of the outer conductive sheath causes current to flow across a secondary arcing region between the distal side edge of the outer conductive sheath and the distal side edge of the inner conductive sheath.

9. The catheter of claim 1 wherein when said voltage pulse is applied a positive pressure spike is generated and thereafter a negative pressure spike is generated.

10. A catheter for treating an occlusion in a body lumen, the catheter comprising:

a fluid lumen configured to receive a conductive fluid and direct the conductive fluid out of a distal end of the catheter;

an electrode assembly including (i) a cylindrical inner conductive ring having an uninsulated distal side edge that extends circumferentially around a longitudinal axis of the cylindrical inner conductive ring, and (ii) a cylindrical outer conductive ring spaced apart from the inner conductive ring, the outer conductive ring having a distal side edge adjacent to the distal side edge of the inner conductive ring; and an insulator positioned between the outer conductive ring and the inner conductive ring, wherein the electrode assembly is positioned such that conductive fluid flows across the electrode assembly when conductive fluid is received in the fluid lumen, and wherein when conductive fluid flows across the electrode assembly and a voltage pulse is applied across the inner conductive ring and the outer conductive ring, current flows across an arcing region between the inner conductive ring and the outer conductive ring to generate at least one of cavitation bubbles and shock waves in the conductive fluid directed out the distal end of the catheter to treat the occlusion.

11. The catheter of claim 10, comprising an aspiration lumen for removing debris and the conductive fluid from the body lumen.

12. The catheter of claim 11, further comprising an outer body, wherein the aspiration lumen and the fluid lumen are defined in the outer body.

13. The catheter of claim 12, wherein the electrode assembly is mounted within the outer body adjacent to the distal end of the catheter.

14. The catheter of claim 10, wherein the outer conductive ring is mounted circumferentially around the inner conductive ring.

15. The catheter of claim 14, wherein the inner conductive ring is mounted such that fluid received in the fluid lumen flows through the inner conductive ring.

16. The catheter of claim 14, wherein the outer conductive ring, the insulator, and the inner conductive ring are mounted within the fluid lumen.

17. The catheter of claim 10, wherein the insulator includes a cylindrical sheath mounted between the outer conductive ring and the inner conductive ring.

18. A catheter for treating an occlusion in a body lumen, the catheter comprising:

a fluid lumen configured to receive a conductive fluid and direct the conductive fluid out of a distal end of the catheter;

an aspiration lumen configured to remove debris and the conductive fluid from the body lumen;

an electrode assembly including (i) an inner conductive cylinder having an uninsulated distal side edge that extends circumferentially around a longitudinal axis of the inner conductive cylinder, and (ii) an outer conductive cylinder spaced apart from the inner conductive cylinder, the outer conductive cylinder having a distal side edge proximate to the distal side edge of the inner conductive cylinder; and an insulator positioned between the outer conductive cylinder and the inner conductive cylinder, wherein the inner conductive cylinder, the outer conductive cylinder, and the insulator are positioned in the fluid lumen such that conductive fluid flows across a portion of the electrode assembly when conductive fluid is received in the fluid lumen, and wherein when conductive fluid flows across the electrode assembly and a voltage pulse is applied across the inner conductive cylinder and the outer conductive cylinder, current flows across an arcing region between the inner conductive cylinder and the outer conductive cylinder to generate at least one of cavitation bubbles and shock waves in the conductive fluid directed out the distal end of the catheter to treat the occlusion.

19. The catheter of claim 18, wherein insulator includes a cylinder mounted between the outer conductive cylinder and the inner conductive cylinder.

20. The catheter of claim 18, further comprising an outer body, wherein the aspiration lumen and the fluid lumen are positioned in the outer body and the electrode assembly and insulator are mounted within the outer body.

* * * * *